US012274497B2

(12) United States Patent
Cook et al.

(10) Patent No.: US 12,274,497 B2
(45) Date of Patent: Apr. 15, 2025

(54) MULTIPLEXER FOR LASER-DRIVEN INTRAVASCULAR LITHOTRIPSY DEVICE

(71) Applicant: Bolt Medical, Inc., Carlsbad, CA (US)

(72) Inventors: Christopher A. Cook, Laguna Niguel, CA (US); Gerald D. Bacher, Carlsbad, CA (US); Eric Schultheis, San Clemente, CA (US); Mina Mossayebi, Irvine, CA (US); Wenjie Xie, La Crescenta, CA (US); Yu Liu, Irvine, CA (US)

(73) Assignee: BOLT MEDICAL, INC., Carlsbad, CA (US)

( * ) Notice: Subject to any disclaimer, the term of this patent is extended or adjusted under 35 U.S.C. 154(b) by 816 days.

(21) Appl. No.: 17/118,427

(22) Filed: Dec. 10, 2020

(65) Prior Publication Data

US 2021/0186613 A1    Jun. 24, 2021

Related U.S. Application Data

(60) Provisional application No. 63/013,975, filed on Apr. 22, 2020, provisional application No. 62/950,014, filed on Dec. 18, 2019.

(51) Int. Cl.
*A61B 18/24* (2006.01)
*A61B 18/00* (2006.01)
(Continued)

(52) U.S. Cl.
CPC .......... *A61B 18/245* (2013.01); *G02B 6/4214* (2013.01); *G02B 27/283* (2013.01); *A61B 2018/0022* (2013.01)

(58) Field of Classification Search
CPC .................. A61B 18/245; A61B 18/26; A61B 2018/0022; A61B 2018/00386;
(Continued)

(56) References Cited

U.S. PATENT DOCUMENTS

| 4,649,924 A | 3/1987 | Taccardi |
| 4,699,147 A | 10/1987 | Chilson et al. |

(Continued)

FOREIGN PATENT DOCUMENTS

| AU | 2017205323 | 1/2022 |
| AU | 2019452180 | 1/2022 |

(Continued)

OTHER PUBLICATIONS

International Search Report and Written Opinion, issued by the European Patent Office for PCT/2021/XXX, dated Sep. 30, 2021.

(Continued)

*Primary Examiner* — Rex R Holmes
*Assistant Examiner* — Shreya Anjaria
(74) *Attorney, Agent, or Firm* — ROEDER & BRODER LLP; James P. Broder

(57) ABSTRACT

A catheter system for treating a vascular lesion within or adjacent to a vessel wall within a body of a patient includes a single light source that generates light energy, a first light guide and a second light guide, and a multiplexer. The first light guide and the second light guide are each configured to selectively receive light energy from the light source. The multiplexer receives the light energy from the light source in the form of a source beam and selectively directs the light energy from the light source in the form of individual guide beams to each of the first light guide and the second light guide.

13 Claims, 13 Drawing Sheets

(51) Int. Cl.
*G02B 6/42* (2006.01)
*G02B 27/28* (2006.01)

(58) Field of Classification Search
CPC ........... A61B 2018/00422; A61B 2018/20359;
A61B 2018/2211; A61B 2018/2261;
A61B 2018/2266; A61B 2018/2272;
A61B 2018/263; A61B 2018/266; G02B
6/3624; G02B 6/4206; G02B 6/4214;
G02B 27/283
See application file for complete search history.

(56) References Cited

U.S. PATENT DOCUMENTS

| | | |
|---|---|---|
| 4,799,479 A | 1/1989 | Spears |
| 4,850,351 A | 7/1989 | Herman |
| 4,913,142 A | 4/1990 | Kittrell et al. |
| 4,932,954 A | 6/1990 | Wondrazek et al. |
| 4,955,895 A | 9/1990 | Sugiyama |
| 4,960,108 A | 10/1990 | Reichel et al. |
| 4,994,059 A | 2/1991 | Kosa et al. |
| 4,998,930 A | 3/1991 | Lundahl |
| 5,034,010 A | 7/1991 | Kittrell et al. |
| 5,041,121 A | 8/1991 | Wondrazek et al. |
| 5,082,343 A | 1/1992 | Coult et al. |
| 5,093,877 A | 3/1992 | Aita et al. |
| 5,104,391 A | 4/1992 | Ingle |
| 5,104,392 A | 4/1992 | Kittrell et al. |
| 5,109,452 A | 4/1992 | Selvin et al. |
| 5,116,227 A | 5/1992 | Levy |
| 5,126,165 A | 6/1992 | Akihama et al. |
| 5,152,768 A | 10/1992 | Bhatta |
| 5,173,049 A | 12/1992 | Levy |
| 5,176,674 A | 1/1993 | Hofmann |
| 5,181,921 A | 1/1993 | Makita et al. |
| 5,200,838 A | 4/1993 | Nudelman |
| 5,290,277 A | 3/1994 | Vercimak et al. |
| 5,324,282 A | 6/1994 | Dodick |
| 5,328,472 A | 7/1994 | Steinke et al. |
| 5,336,184 A | 8/1994 | Teirstein |
| 5,372,138 A | 12/1994 | Crowley |
| 5,387,225 A | 2/1995 | Euteneur |
| 5,400,428 A | 3/1995 | Grace |
| 5,410,797 A | 5/1995 | Steinke et al. |
| 5,422,926 A | 6/1995 | Smith |
| 5,454,809 A | 10/1995 | Janssen |
| 5,456,680 A | 10/1995 | Taylor |
| 5,474,537 A | 12/1995 | Solar |
| 5,509,917 A | 4/1996 | Cecchetti |
| 5,540,679 A | 7/1996 | Fram |
| 5,562,657 A | 10/1996 | Griffin |
| 5,598,494 A | 1/1997 | Behrmann et al. |
| 5,609,606 A | 3/1997 | O'Boyle |
| 5,611,807 A | 3/1997 | O'Boyle |
| 5,661,829 A | 8/1997 | Zheng |
| 5,697,377 A | 12/1997 | Wittkamph |
| 5,718,241 A | 2/1998 | Ben-Haim et al. |
| 5,729,583 A | 3/1998 | Tang |
| 5,764,843 A | 6/1998 | Macken et al. |
| 5,772,609 A | 6/1998 | Nguyen et al. |
| 5,860,974 A | 1/1999 | Abele |
| 5,891,135 A | 4/1999 | Jackson et al. |
| 5,906,611 A | 5/1999 | Dodick et al. |
| 5,944,697 A | 8/1999 | Benett et al. |
| 6,015,404 A | 1/2000 | Altshuler |
| 6,080,119 A | 6/2000 | Schwarze et al. |
| 6,123,923 A | 9/2000 | Unger |
| 6,139,510 A | 10/2000 | Palermo |
| 6,186,963 B1 | 2/2001 | Schwarze et al. |
| 6,203,537 B1 | 3/2001 | Adrian |
| 6,210,404 B1 | 4/2001 | Shadduck |
| 6,339,470 B1 | 1/2002 | Papademetriou et al. |
| 6,356,575 B1 | 3/2002 | Fukumoto |
| 6,368,318 B1 | 4/2002 | Visuri et al. |
| 6,423,055 B1 | 7/2002 | Farr |
| 6,500,174 B1 | 12/2002 | Maguire et al. |
| 6,514,203 B2 | 2/2003 | Bukshpan |
| 6,514,249 B1 | 2/2003 | Maguire |
| 6,524,251 B2 | 3/2003 | Rabiner et al. |
| 6,538,739 B1 | 3/2003 | Visuri et al. |
| 6,548,010 B1 | 4/2003 | Stivland et al. |
| 6,560,387 B1 | 5/2003 | Hehlen et al. |
| 6,607,502 B1 | 8/2003 | Maguire et al. |
| 6,631,220 B1 | 10/2003 | Liang et al. |
| 6,652,547 B2 | 11/2003 | Rabiner et al. |
| 6,666,834 B2 | 12/2003 | Restle et al. |
| 6,702,781 B1 | 3/2004 | Reifart et al. |
| 6,773,447 B2 | 8/2004 | Laguna |
| 6,824,554 B1 | 11/2004 | Jang |
| 6,849,994 B1 | 2/2005 | White et al. |
| 6,890,317 B2 | 5/2005 | Gerdts et al. |
| 6,947,785 B1 | 9/2005 | Beatty et al. |
| 6,966,890 B2 | 11/2005 | Coyle et al. |
| 6,978,168 B2 | 12/2005 | Beatty et al. |
| 6,990,370 B1 | 1/2006 | Beatty et al. |
| 7,273,470 B2 | 9/2007 | Wantink |
| 7,309,324 B2 | 12/2007 | Hayes et al. |
| 7,367,967 B2 | 5/2008 | Eidenschink |
| 7,470,240 B2 | 12/2008 | Schultheiss et al. |
| 7,539,231 B1 | 5/2009 | Honea et al. |
| 7,569,032 B2 | 8/2009 | Naimark et al. |
| 7,599,588 B2 | 10/2009 | Eberle et al. |
| 7,641,646 B2 | 1/2010 | Kennedy, II |
| 7,713,260 B2 | 5/2010 | Lessard |
| 7,758,572 B2 | 7/2010 | Weber et al. |
| 7,762,984 B2 | 7/2010 | Kumoyama et al. |
| 7,810,395 B2 | 10/2010 | Zhou |
| 7,850,685 B2 | 12/2010 | Kunis et al. |
| 7,867,178 B2 | 1/2011 | Simnacher |
| 7,909,797 B2 | 3/2011 | Kennedy, II et al. |
| 7,967,781 B2 | 6/2011 | Simpson et al. |
| 7,972,299 B2 | 7/2011 | Carter |
| 7,985,189 B1 | 7/2011 | Ogden et al. |
| 8,021,328 B2 | 9/2011 | Lee |
| 8,029,473 B2 | 10/2011 | Carter |
| 8,043,256 B2 | 10/2011 | Hansen |
| 8,088,121 B2 | 1/2012 | Nishide |
| 8,162,859 B2 | 4/2012 | Schultheiss et al. |
| 8,166,825 B2 | 5/2012 | Zhou |
| 8,192,368 B2 | 6/2012 | Woodruff |
| 8,267,886 B2 | 9/2012 | Ewing |
| 8,292,913 B2 | 10/2012 | Warnack |
| 8,328,820 B2 | 12/2012 | Diamant |
| 8,364,235 B2 | 1/2013 | Kordis et al. |
| 8,382,738 B2 | 2/2013 | Simpson et al. |
| 8,414,527 B2 | 4/2013 | Mallaby |
| 8,419,613 B2 | 4/2013 | Saadat |
| 8,439,890 B2 | 5/2013 | Beyar |
| 8,556,813 B2 | 10/2013 | Cashman et al. |
| 8,574,247 B2 | 11/2013 | Adams et al. |
| 8,657,814 B2 | 2/2014 | Werneth |
| 8,709,075 B2 | 4/2014 | Adams et al. |
| 8,728,091 B2 | 5/2014 | Hakala et al. |
| 8,734,424 B2 | 5/2014 | Watanabe |
| 8,747,416 B2 | 6/2014 | Hakala et al. |
| 8,784,362 B2 | 7/2014 | Boutilette |
| 8,834,510 B2 | 9/2014 | Wilson et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 8,986,339 B2 | 3/2015 | Warnack |
| 8,992,817 B2 | 3/2015 | Stamberg |
| 9,005,216 B2 | 4/2015 | Hakala et al. |
| 9,011,462 B2 | 4/2015 | Adams et al. |
| 9,011,463 B2 | 4/2015 | Adams et al. |
| 9,011,511 B2 | 4/2015 | Gregorich |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,089,669 B2 | 7/2015 | Haslinger et al. |
| 9,131,949 B2 | 9/2015 | Coleman et al. |
| 9,138,249 B2 | 9/2015 | Adams et al. |
| 9,138,260 B2 | 9/2015 | Miller et al. |
| 9,180,280 B2 | 11/2015 | Hawkins et al. |

(56) References Cited

U.S. PATENT DOCUMENTS

| | | |
|---|---|---|
| 9,220,521 B2 | 12/2015 | Hawkins et al. |
| 9,237,984 B2 | 1/2016 | Hawkins et al. |
| 9,289,132 B2 | 3/2016 | Ghaffari et al. |
| 9,289,224 B2 | 3/2016 | Adams et al. |
| 9,320,530 B2 | 4/2016 | Grace |
| 9,333,000 B2 | 5/2016 | Hakala et al. |
| 9,339,632 B2 | 5/2016 | Eidenschink et al. |
| 9,364,645 B2 | 6/2016 | Erikawa |
| 9,375,223 B2 | 6/2016 | Wallace |
| 9,421,025 B2 | 8/2016 | Hawkins et al. |
| 9,433,428 B2 | 9/2016 | Hakala et al. |
| 9,433,745 B2 | 9/2016 | Cully |
| 9,504,809 B2 | 11/2016 | Bo |
| 9,510,887 B2 | 12/2016 | Burnett |
| 9,522,012 B2 | 12/2016 | Adams |
| 9,554,815 B2 | 1/2017 | Adams et al. |
| 9,555,267 B2 | 1/2017 | Ein-Gal |
| 9,566,209 B2 | 2/2017 | Katragadda et al. |
| 9,579,114 B2 | 2/2017 | Mantell et al. |
| 9,585,684 B2 | 3/2017 | Nita et al. |
| 9,592,328 B2 | 3/2017 | Jeevanandam |
| 9,629,567 B2 | 4/2017 | Porath et al. |
| 9,642,673 B2 | 5/2017 | Adams |
| 9,662,069 B2 | 5/2017 | De Graff et al. |
| 9,687,166 B2 | 6/2017 | Subramaniam |
| 9,730,715 B2 | 8/2017 | Adams |
| 9,737,361 B2 | 8/2017 | Magana |
| 9,764,142 B2 | 9/2017 | Imran |
| 9,782,570 B2 | 10/2017 | Hirszowicz |
| 9,814,476 B2 | 11/2017 | Adams et al. |
| 9,833,348 B2 | 12/2017 | Jordan et al. |
| 9,839,764 B2 | 12/2017 | Chouinard |
| 9,861,377 B2 | 1/2018 | Mantell et al. |
| 9,867,629 B2 | 1/2018 | Hawkins et al. |
| 9,878,135 B2 | 1/2018 | Holzapfel et al. |
| 9,894,756 B2 | 2/2018 | Weinkam et al. |
| 9,901,704 B2 | 2/2018 | Appling |
| 9,955,946 B2 | 5/2018 | Miller et al. |
| 9,974,963 B2 | 5/2018 | Imran |
| 9,974,970 B2 | 5/2018 | Nuta et al. |
| 9,993,292 B2 | 6/2018 | Adams et al. |
| 10,039,561 B2 | 8/2018 | Adams et al. |
| 10,086,175 B2 | 10/2018 | Torres et al. |
| 10,124,153 B2 | 11/2018 | Feig |
| 10,136,829 B2 | 11/2018 | Deno et al. |
| 10,149,690 B2 | 12/2018 | Hawkins et al. |
| 10,159,505 B2 | 12/2018 | Hakala et al. |
| 10,194,994 B2 | 2/2019 | Deno et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,245,410 B2 | 4/2019 | Aggerholm |
| 10,357,264 B2 | 7/2019 | Kat-Kuoy |
| 10,405,923 B2 | 9/2019 | Yu et al. |
| 10,406,031 B2 | 9/2019 | Thyzel |
| 10,406,318 B2 | 9/2019 | Williams |
| 10,420,569 B2 | 9/2019 | Adams |
| 10,439,791 B2 | 10/2019 | Kalhan |
| 10,441,300 B2 | 10/2019 | Hawkins |
| 10,449,339 B2 | 10/2019 | Wilson et al. |
| 10,463,430 B2 | 11/2019 | Dick |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,583,277 B2 | 3/2020 | Rundquist |
| 10,589,073 B2 | 3/2020 | Mallaby |
| 10,617,850 B2 | 4/2020 | Tal |
| 10,646,240 B2 | 5/2020 | Betelia et al. |
| 10,668,245 B2 | 6/2020 | Kanae |
| 10,682,178 B2 | 6/2020 | Adams et al. |
| 10,695,531 B2 | 6/2020 | Suzuki |
| 10,702,293 B2 | 7/2020 | Adams et al. |
| 10,709,462 B2 | 7/2020 | Nguyen et al. |
| 10,709,872 B2 | 7/2020 | Alvarez et al. |
| 10,758,255 B2 | 9/2020 | Adams |
| 10,797,684 B1 | 10/2020 | Benz et al. |
| 10,799,688 B2 | 10/2020 | Calhoun |
| 10,842,567 B2 | 11/2020 | Grace et al. |
| 10,850,075 B2 | 12/2020 | Tarunaga |
| 10,857,329 B2 | 12/2020 | Davies |
| 10,933,225 B2 | 3/2021 | Campbell |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 10,980,987 B2 | 4/2021 | Tarunaga |
| 11,000,299 B2 | 5/2021 | Hawkins et al. |
| 11,020,135 B1 | 6/2021 | Hawkins |
| 11,026,707 B2 | 6/2021 | Ku et al. |
| 11,058,492 B2 | 7/2021 | Grace et al. |
| 11,076,874 B2 | 8/2021 | Hakala et al. |
| 11,116,939 B2 | 9/2021 | Jamous et al. |
| 11,141,131 B2 | 10/2021 | Stigall |
| 11,207,493 B2 | 12/2021 | Suzuki et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 11,253,681 B2 | 2/2022 | Williams |
| 11,484,327 B2 | 11/2022 | Anderson et al. |
| 11,633,200 B2 | 4/2023 | Anderson et al. |
| 11,779,363 B2 | 10/2023 | Vo |
| 11,826,530 B2 | 11/2023 | Suzuki |
| 11,911,054 B2 | 2/2024 | Singla |
| 11,911,056 B2 | 2/2024 | Anderson et al. |
| 11,918,285 B2 | 3/2024 | Sun et al. |
| 11,944,331 B2 | 4/2024 | Anderson et al. |
| 2001/0016761 A1 | 8/2001 | Rudie |
| 2001/0049464 A1 | 12/2001 | Ganz |
| 2001/0051784 A1 | 12/2001 | Brisken |
| 2002/0045811 A1* | 4/2002 | Kittrell ............... G02B 6/4296 606/7 |
| 2002/0052621 A1 | 5/2002 | Fried et al. |
| 2002/0065512 A1 | 5/2002 | Fjield et al. |
| 2002/0082553 A1 | 6/2002 | Duchamp |
| 2002/0183620 A1 | 12/2002 | Tearney |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0125719 A1 | 7/2003 | Furnish |
| 2003/0144654 A1 | 7/2003 | Hilal |
| 2003/0176873 A1 | 9/2003 | Chernenko et al. |
| 2004/0002677 A1 | 1/2004 | Gentsler |
| 2004/0024349 A1 | 2/2004 | Flock et al. |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0210278 A1 | 10/2004 | Boll |
| 2004/0243119 A1 | 12/2004 | Lane et al. |
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0259319 A1 | 11/2005 | Brooker |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0098921 A1 | 5/2006 | Benaron et al. |
| 2006/0190022 A1 | 8/2006 | Beyar et al. |
| 2006/0200039 A1 | 9/2006 | Brockway et al. |
| 2006/0221528 A1 | 10/2006 | Li et al. |

(56) References Cited

U.S. PATENT DOCUMENTS

| | | |
|---|---|---|
| 2006/0241524 A1 | 10/2006 | Lee et al. |
| 2006/0241572 A1* | 10/2006 | Zhou .................... G10K 15/046 606/7 |
| 2006/0241733 A1 | 10/2006 | Zhang et al. |
| 2006/0270976 A1 | 11/2006 | Savage et al. |
| 2007/0027524 A1 | 2/2007 | Johnson |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-Gal |
| 2007/0142819 A1 | 6/2007 | El-Nounou et al. |
| 2007/0142821 A1 | 6/2007 | Hennessy et al. |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0280311 A1 | 12/2007 | Hofmann |
| 2007/0299392 A1 | 12/2007 | Beyar et al. |
| 2008/0033519 A1 | 2/2008 | Burwell |
| 2008/0081950 A1 | 4/2008 | Koenig et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0175539 A1 | 7/2008 | Brown |
| 2008/0195088 A1 | 8/2008 | Farr et al. |
| 2008/0214891 A1 | 9/2008 | Slenker et al. |
| 2008/0221550 A1 | 9/2008 | Lee |
| 2008/0281157 A1 | 11/2008 | Miyagi et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0131921 A1 | 5/2009 | Kurtz et al. |
| 2009/0192495 A1 | 7/2009 | Ostrovsky et al. |
| 2009/0240242 A1 | 9/2009 | Neuberger |
| 2009/0247945 A1 | 10/2009 | Levit |
| 2009/0281531 A1 | 11/2009 | Rizoiu |
| 2009/0292296 A1 | 11/2009 | Pansky |
| 2009/0296751 A1 | 12/2009 | Kewitsch et al. |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0063491 A1 | 3/2010 | Verhagen |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160838 A1 | 6/2010 | Krespi |
| 2010/0160903 A1 | 6/2010 | Krespi |
| 2010/0168572 A1 | 7/2010 | Sliwa |
| 2010/0168836 A1 | 7/2010 | Kassab |
| 2010/0168862 A1 | 7/2010 | Edie et al. |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2010/0265733 A1 | 10/2010 | O'Leary |
| 2010/0316333 A1 | 12/2010 | Luther |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2011/0306956 A1 | 12/2011 | Islam |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0089132 A1 | 4/2012 | Dick et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0143131 A1 | 6/2012 | Tun |
| 2012/0157892 A1 | 6/2012 | Reitmajer et al. |
| 2012/0197245 A1 | 8/2012 | Burnett |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0110003 A1 | 5/2013 | Surti |
| 2013/0116714 A1 | 5/2013 | Adams et al. |
| 2013/0165764 A1 | 6/2013 | Scheuermann |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0274726 A1 | 10/2013 | Takayama |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0309536 A1 | 10/2014 | Douk et al. |
| 2014/0336632 A1 | 11/2014 | Toth |
| 2014/0336637 A1 | 11/2014 | Agrawal |
| 2014/0357997 A1 | 12/2014 | Hartmann |
| 2015/0003900 A1 | 1/2015 | Ullrich et al. |
| 2015/0005576 A1 | 1/2015 | Diodone et al. |
| 2015/0039002 A1 | 2/2015 | Hawkins |
| 2015/0057648 A1 | 2/2015 | Swift et al. |
| 2015/0073430 A1 | 3/2015 | Hakala et al. |
| 2015/0080875 A1 | 3/2015 | Kasprzyk et al. |
| 2015/0105715 A1 | 4/2015 | Pikus et al. |

(56) References Cited

U.S. PATENT DOCUMENTS

| | | |
|---|---|---|
| 2015/0119870 A1 | 4/2015 | Rudie |
| 2015/0126990 A1 | 5/2015 | Sharma |
| 2015/0141764 A1 | 5/2015 | Harks et al. |
| 2015/0250542 A1 | 9/2015 | Islam |
| 2015/0276689 A1 | 10/2015 | Watanabe et al. |
| 2015/0313732 A1 | 11/2015 | Fulton, III |
| 2015/0320432 A1 | 11/2015 | Adams |
| 2015/0342678 A1 | 12/2015 | Deladurantaye et al. |
| 2015/0359432 A1 | 12/2015 | Ehrenreich |
| 2015/0359557 A1 | 12/2015 | Shimokawa |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0135891 A1 | 5/2016 | Feldman |
| 2016/0143522 A1 | 5/2016 | Ransbury |
| 2016/0151639 A1 | 6/2016 | Scharf et al. |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184526 A1 | 6/2016 | Beyar |
| 2016/0184570 A1 | 6/2016 | Grace et al. |
| 2016/0228187 A1 | 8/2016 | Gross |
| 2016/0262784 A1 | 9/2016 | Grace et al. |
| 2016/0270806 A1 | 9/2016 | Wallace |
| 2016/0302762 A1 | 10/2016 | Stigall et al. |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0056087 A1 | 3/2017 | Buckley |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0151421 A1 | 6/2017 | Asher |
| 2017/0192242 A1 | 7/2017 | Laycock |
| 2017/0209050 A1 | 7/2017 | Fengler et al. |
| 2017/0265942 A1* | 9/2017 | Grace ................ A61B 18/245 |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0045897 A1 | 2/2018 | Chia |
| 2018/0049877 A1 | 2/2018 | Venkatasubramanian |
| 2018/0085174 A1 | 3/2018 | Radtke et al. |
| 2018/0092763 A1 | 4/2018 | Dagan et al. |
| 2018/0095287 A1 | 4/2018 | Jeng et al. |
| 2018/0098779 A1 | 4/2018 | Betelia et al. |
| 2018/0152568 A1 | 6/2018 | Kat-kuoy |
| 2018/0214677 A1 | 8/2018 | Tarunaga |
| 2018/0238675 A1* | 8/2018 | Wan ................ G01B 9/02002 |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0323571 A1 | 11/2018 | Brown et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0072378 A1 | 3/2019 | Hane et al. |
| 2019/0097380 A1 | 3/2019 | Luft et al. |
| 2019/0099588 A1 | 4/2019 | Ramanath et al. |
| 2019/0104933 A1 | 4/2019 | Stern |
| 2019/0117242 A1 | 4/2019 | Lawinger |
| 2019/0150960 A1 | 5/2019 | Nguyen et al. |
| 2019/0150961 A1 | 5/2019 | Tozzi |
| 2019/0167349 A1 | 6/2019 | Shamay |
| 2019/0175111 A1 | 6/2019 | Genereux et al. |
| 2019/0175300 A1 | 6/2019 | Horn et al. |
| 2019/0175372 A1 | 6/2019 | Boydan et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1* | 8/2019 | Tayebati ................ H01S 3/23 |
| 2019/0282249 A1 | 9/2019 | Tran et al. |
| 2019/0282250 A1 | 9/2019 | Tran et al. |
| 2019/0321100 A1 | 10/2019 | Masotti et al. |
| 2019/0321101 A1 | 10/2019 | Massoti et al. |
| 2019/0328259 A1 | 10/2019 | Deno et al. |
| 2019/0365400 A1 | 12/2019 | Adams et al. |
| 2019/0380589 A1* | 12/2019 | Lloret Soler ........ A61B 5/0075 |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046429 A1 | 2/2020 | Tschida et al. |
| 2020/0046949 A1 | 2/2020 | Chisena et al. |
| 2020/0054352 A1 | 2/2020 | Brouillette et al. |
| 2020/0060814 A1 | 2/2020 | Murphy |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0101269 A1 | 4/2020 | Hayes |
| 2020/0107960 A1 | 4/2020 | Bacher |
| 2020/0108236 A1 | 4/2020 | Salazar et al. |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0397453 A1 | 12/2020 | McGowan |
| 2020/0398033 A1 | 12/2020 | McGowan et al. |
| 2020/0405333 A1 | 12/2020 | Massimini et al. |
| 2020/0405391 A1 | 12/2020 | Massimini |
| 2020/0406009 A1 | 12/2020 | Massimini |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0116302 A1 | 4/2021 | Jean-Ruel |
| 2021/0128241 A1 | 5/2021 | Schultheis |
| 2021/0137598 A1 | 5/2021 | Cook et al. |
| 2021/0153939 A1 | 5/2021 | Cook |
| 2021/0177442 A1 | 6/2021 | Girdhar et al. |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |

(56) References Cited

U.S. PATENT DOCUMENTS

| | | | |
|---|---|---|---|
| 2021/0290305 A1 | 9/2021 | Cook | |
| 2021/0298603 A1 | 9/2021 | Feldman | |
| 2021/0307828 A1 | 10/2021 | Schultheis | |
| 2021/0330384 A1 | 10/2021 | Cook | |
| 2021/0338258 A1 | 11/2021 | Hawkins et al. | |
| 2021/0353359 A1 | 11/2021 | Cook | |
| 2021/0369348 A1 | 12/2021 | Cook | |
| 2021/0378743 A1 | 12/2021 | Massimini et al. | |
| 2021/0378744 A1 | 12/2021 | Fanier et al. | |
| 2021/0386479 A1 | 12/2021 | Massimini et al. | |
| 2022/0000505 A1 | 1/2022 | Hauser | |
| 2022/0000506 A1 | 1/2022 | Hauser | |
| 2022/0000507 A1 | 1/2022 | Hauser | |
| 2022/0000508 A1 | 1/2022 | Schmitt et al. | |
| 2022/0000509 A1 | 1/2022 | Laser et al. | |
| 2022/0000551 A1 | 1/2022 | Govari et al. | |
| 2022/0008130 A1 | 1/2022 | Massimini et al. | |
| 2022/0008693 A1 | 1/2022 | Humbert et al. | |
| 2022/0015785 A1 | 1/2022 | Hakala et al. | |
| 2022/0021190 A1 | 1/2022 | Pecquois | |
| 2022/0022902 A1 | 1/2022 | Spano | |
| 2022/0022912 A1 | 1/2022 | Efremkin | |
| 2022/0023528 A1 | 1/2022 | Long et al. | |
| 2022/0071704 A1 | 3/2022 | Le | |
| 2022/0168594 A1 | 6/2022 | Mayer | |
| 2022/0183738 A1 | 6/2022 | Flores et al. | |
| 2022/0218402 A1 | 7/2022 | Schultheis | |
| 2022/0249165 A1 | 8/2022 | Cook | |
| 2022/0273324 A1 | 9/2022 | Schultheis | |
| 2022/0287732 A1 | 9/2022 | Anderson et al. | |
| 2022/0313293 A1 | 10/2022 | Singh | |
| 2022/0338890 A1 | 10/2022 | Anderson et al. | |
| 2022/0354578 A1 | 11/2022 | Cook | |
| 2022/0387106 A1 | 12/2022 | Cook | |
| 2023/0013920 A1 | 1/2023 | Massimini | |
| 2023/0248376 A1 | 8/2023 | Anderson et al. | |
| 2023/0310073 A1 | 10/2023 | Adams et al. | |
| 2023/0414234 A1 | 12/2023 | Anderson et al. | |
| 2024/0058060 A1 | 2/2024 | Cook | |
| 2024/0065712 A1 | 2/2024 | Schultheis | |
| 2024/0122648 A1 | 4/2024 | Cook | |
| 2024/0189543 A1 | 6/2024 | Salinas | |
| 2024/0216062 A1 | 7/2024 | Cook | |
| 2024/0277410 A1 | 8/2024 | Cook | |
| 2024/0285296 A1 | 8/2024 | Vo | |
| 2024/0382258 A1 | 11/2024 | Schultheis | |

FOREIGN PATENT DOCUMENTS

| | | |
|---|---|---|
| AU | 2022227829 | 9/2022 |
| CA | 2229806 | 3/1997 |
| CA | 2281519 | 8/1998 |
| CA | 2983655 | 10/2016 |
| CA | 3209797 | 9/2022 |
| CN | 102057422 | 5/2011 |
| CN | 109223100 | 1/2019 |
| CN | 110638501 | 1/2020 |
| CN | 110638501 A | 1/2020 |
| CN | 106794043 | 3/2020 |
| CN | 11399346 | 1/2022 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| CN | 114053552 | 2/2022 |
| CN | 115175625 | 10/2022 |
| DE | 3038445 A1 | 5/1982 |
| DE | 3836337 A | 4/1990 |
| DE | 3913027 A1 | 10/1990 |
| DE | 69431758 | 1/2003 |
| DE | 10230626 | 1/2004 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 1453566 | 9/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3266487 | 1/2018 |
| EP | 3318204 | 5/2018 |
| EP | 2879607 | 2/2019 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 3960099 | 3/2022 |
| EP | 4051154 | 9/2022 |
| EP | 4129213 | 2/2023 |
| EP | 4277537 | 11/2023 |
| EP | 4297669 | 1/2024 |
| EP | 3182931 | 6/2024 |
| EP | 3950036 | 8/2024 |
| GB | 1082397 | 9/1967 |
| JP | S62275446 A | 11/1987 |
| JP | 1996089511 | 4/1996 |
| JP | H09117407 | 5/1997 |
| JP | 2004519296 | 7/2004 |
| JP | 2008506447 | 3/2008 |
| JP | 2008083273 | 4/2008 |
| JP | 2009519777 | 5/2009 |
| JP | 2009213589 | 9/2009 |
| JP | 2011524203 | 9/2011 |
| JP | 4805208 | 11/2011 |
| JP | 4808620 | 11/2011 |
| JP | 2014123147 | 7/2014 |
| JP | 2015217215 | 12/2015 |
| JP | 2018538077 | 12/2018 |
| JP | 2024511710 | 3/2024 |
| KR | 20050098932 | 10/2005 |
| KR | 20080040111 | 5/2008 |
| KR | 20160090877 A | 8/2016 |
| KR | 20180054041 | 5/2018 |
| WO | WO9007904 A1 | 7/1990 |
| WO | WO9105332 A1 | 4/1991 |
| WO | WO9203095 A1 | 3/1992 |
| WO | 1992008515 A2 | 5/1992 |
| WO | WO9208515 | 5/1992 |
| WO | WO9524867 | 9/1995 |
| WO | 9902095 A1 | 1/1999 |
| WO | 9920189 A1 | 4/1999 |

(56) References Cited

FOREIGN PATENT DOCUMENTS

| | | |
|---|---|---|
| WO | WO200067648 | 11/2000 |
| WO | WO2000067648 A1 | 11/2000 |
| WO | 2001003599 A1 | 1/2001 |
| WO | WO0103599 | 1/2001 |
| WO | 2006006169 A2 | 1/2006 |
| WO | WO2006006169 | 1/2006 |
| WO | WO2009121017 | 10/2009 |
| WO | WO2009149321 A1 | 12/2009 |
| WO | WO2009152352 A2 | 12/2009 |
| WO | 2010042653 A1 | 4/2010 |
| WO | WO2011094379 | 8/2011 |
| WO | 2011126580 A2 | 10/2011 |
| WO | WO2011126580 A3 | 10/2011 |
| WO | WO2012025833 | 3/2012 |
| WO | WO2012042619 | 4/2012 |
| WO | WO20120052924 A1 | 4/2012 |
| WO | WO2012058156 | 5/2012 |
| WO | WO2012099974 A2 | 7/2012 |
| WO | WO20120120495 A2 | 9/2012 |
| WO | WO2013119662 | 8/2013 |
| WO | WO2013169807 | 11/2013 |
| WO | WO2013169807 A1 | 11/2013 |
| WO | WO2014022436 A1 | 2/2014 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 2015177790 A1 | 11/2015 |
| WO | WO2016014999 | 1/2016 |
| WO | WO2016089683 A1 | 6/2016 |
| WO | WO2016090175 | 6/2016 |
| WO | WO2016098670 | 6/2016 |
| WO | WO2016109739 | 7/2016 |
| WO | WO2016143556 | 9/2016 |
| WO | WO2016151595 A1 | 9/2016 |
| WO | WO2017004432 A1 | 1/2017 |
| WO | WO20170192869 A1 | 11/2017 |
| WO | WO2018022593 A1 | 2/2018 |
| WO | WO2018022641 A1 | 2/2018 |
| WO | WO2018083666 | 5/2018 |
| WO | WO2018175322 | 9/2018 |
| WO | WO-2018175322 A1 * | 9/2018 ............. A61B 18/22 |
| WO | WO2018191013 | 10/2018 |
| WO | WO2019200201 A1 | 10/2019 |
| WO | WO2019215869 A1 | 11/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020157648 | 8/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021061451 | 4/2021 |
| WO | WO2021067563 | 4/2021 |
| WO | 2021086571 A1 | 5/2021 |
| WO | 2021101766 A1 | 5/2021 |
| WO | WO2021096922 A1 | 5/2021 |
| WO | WO2021101766 | 5/2021 |
| WO | WO2021126762 A1 | 6/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021202248 A1 | 10/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022183075 | 9/2022 |
| WO | WO2022187058 | 9/2022 |
| WO | WO2022216488 | 10/2022 |
| WO | WO2022240674 | 11/2022 |
| WO | WO2022260932 | 12/2022 |
| WO | WO2023107334 | 6/2023 |

OTHER PUBLICATIONS

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.

Tagawa, Y., et al. "Structure of laser-induced shock wave in water", Japan Society for the Promotion of Science, 2016.

Shen, Y., et al. "Theoretical and experimental studies of directivity of sound field generated by pulsed laser induced breakdown in liquid water", SPIE, 2013, pp. 8796141-8796148, vol. 8796, SPIE.

Preisack, M., et al. "Ultrafast imaging of tissue ablation by a XeCl excimer laser in saline", Lasers in Surgery and Medicine, 1992, pp. 520-527, vol. 12, Wiley-Liss Inc.

Versluis, M., et al. "How Snapping Shrimp Snap: Through Cavitating Bubbles", Science Mag, 2000, pp. 2114-2117, vol. 289, American Association for the Advancement of Science, Washington DC, USA.

Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.

Zhang, Q., et al. "Improved Instruments and Methods for the Photographic Study of Spark-Induced Cavitation Bubbles", Water, 2018, pp. 1-12, vol. 10, No. 1683.

"Damage threshold of fiber facets", NKT Photonics, 2012, pp. 1-4, Denmark.

Smith, A., et al. "Bulk and surface laser damage of silica by picosecond and nanosecond pulses at 1064 nm", Applied Optics, 2008, pp. 4812-4832, vol. 47, No. 26, Optical Society of America.

Smith, A., et al. "Deterministic Nanosecond Laser-Induced Breakdown Thresholds in Pure and Yb3 Doped Fused Silica", SPIE, 2007, pp. 6453171-64531712, vol. 6453, SPIE.

Sun, X., et al. "Laser Induced Damage to Large Core Optical Fiber by High Peak Power Laser", Specialty Photonics Division, 2010.

Smith, A., et al. "Nanosecond laser-induced breakdown in pure and Yb3 doped fused silica", SPIE, 2007, vol. 6403, SPIE.

Smith, A., et al. "Optical Damage Limits to Pulse Energy From Fibers", IEEE Journal of Selected Topics in Quantum Electronics, 2009, pp. 153-158, vol. 15, No. 1, IEEE.

Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.

Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.

Reichel, E., et al. "Laser-induced Shock Wave Lithotripsy with a Regenerative Energy Converter", Lasers in Medical Science, 1992, pp. 423-425, vol. 7, Bailliere Tindall.

Hardy, L., et al. "Cavitation Bubble Dynamics during Thulium Fiber Laser Lithotripsy", SPIE BiOS, 2016, vol. 9689, SPIE.

(56) References Cited

OTHER PUBLICATIONS

Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, mailed Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, mailed Jan. 16, 2019.
European Search Report, for European Patent Application No. 18185152.8, mailed Dec. 20, 2018.
International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
International Search Report and Written Opinion dated Jan. 29, 2021 in PCT Application Serial No. PCT/US2020/059961.
International Search Report and Written Opinion dated Jan. 20, 2021 in PCT Application Serial No. PCT/US2020/054792.
Provisional International Search Report and Written Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery of Atrial Endocardial Potential Maps From Non-contact Electrode Data." Auckland Bioengineering Institute. (ID 1421).
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368).
Sacher et al., "Comparison of Manual Vs Automatic Annotation to Identify Abnormal Substrate for Scar Related VT Ablation." LIRYC Institute, Bordeaux University Hospital, France (ID 1336).
Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Aug. 20, 2021 in PCT Application Serial No. PCT/US2021/031130.
Davletshin, Yevgeniy R., "A Computational Analysis of Nanoparticle-Mediated Optical Breakdown", A dissertation presented to Ryerson

(56) References Cited

OTHER PUBLICATIONS

University in Partial Fulfillment of the requirements for the degree of Doctor of Philosophy in the Program of Physics, Toronto, Ontario, CA 2017.

Vogel, A., et al. "Acoustic transient generation by laser-produced cavitation bubbles near solid boundaries", Journal Acoustical Society of America, 1988, pp. 719-731, vol. 84.

Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.

Zheng, W., "Optic Lenses Manufactured on Fiber Ends", 2015, Splicer Engineering AFL, Duncan, SC USA.

Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.

Ali, Ziad A., et al. "Intravascular lithotripsy for treatment of stent underexpansion secondary to severe coronary calcification" 2018, European Society of Cardiology.

Ashok, Praveen C., et al. "Raman spectroscopy bio-sensor for tissue discrimination in surgical robotics—full article", Journal of Biophotonics, 2014, pp. 103-109, vol. 7, No. 1-2.

Ashok, Praveen C., et al. "Raman spectroscopy bio-sensor for tissue discrimination in surgical robotics—proof" Journal of Biophotonics 7, 2014, No. 1-2.

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.

Bian, D. C., et al. "Study on Breakdown Delay Characteristics Based on High-voltage Pulse Discharge in Water with Hydrostatic Pressure", Journal of Power Technologies 97(2), 2017, pp. 89-102.

Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.

Brodmann, Marianne et al. "Safety and Performance of Lithoplasty for Treatment of Calcified Peripheral Artery Lesions", JACC, 2017, vol. 70, No. 7.

Brouillette, M., "Shock Waves at Microscales", 2003, pp. 3-12, Springer-Verlag.

Mirshekari, G., et al. "Shock Waves in Microchannels", 2013, pp. 259-283, vol. 724, Cambridge University Press.

"Bubble Dynamics and Shock Waves", Springer, 2013, Springer-Verlag, Berlin Heildelberg.

Hardy, Luke A., et al. "Cavitation Bubble Dynamics During Thulium Fiber Laser Lithotripsy", SPIE, Feb. 29, 2016, vol. 9689, San Francisco, California, USA.

Claverie, A., et al. "Experimental characterization of plasma formation and shockwave propagation induced by high power pulsed underwater electrical discharge", Review of Scientific Instruments, 2014, American Institute of Physics.

Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.

Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.

Cook, Jason R., et al. "Tissue mimicking phantoms for photoacoustic and ultrasonic imaging", Biomedical Optics Express, 2011, vol. 2, No. 11, Optical Society of America.

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and on Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method for Fabricating Artificial Kidney Stones of Different Physical Properties", National Institute of Health Public Access Author Manuscript, Aug. 2010.

Sner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

(56) References Cited

OTHER PUBLICATIONS

Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, pp. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
International Search Report and Written Opinion, issued by the EP/ISA, in PCT/US2021/048819, dated Jan. 14, 2022.
International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
Medlight, "Cylindrical light diffuser Model RD-ML", Medlight S.A., Switzerland. 2015. (This reference was cited in a prior Information Disclosure Statement. However, the relevant date was missing. The date has now been added.).
Medlight, "Cylindircal light diffuser Model RD", Medlight S.A., Switzerland. 2015. (This reference was cited in a prior Information Disclosure Statement. However, the relevant date was missing. The date has now been added.).
Ohl, Siew-Wan, et al. "Bubbles with shock waves and ultrasound: a review", Interface Focus, pp. 1-15, vol. 5, The Royal Society Publishing. Oct. 2015. (This reference was cited in a prior Information Disclosure Statement. However, the relevant date was missing. The date has now been added.).
Schafter+Kirchhoff, Laser Beam Couplers series 60SMS for coupling into single-mode and polarization-maintaining fiber cables, Schafter+Kirchhoff, pp. 1-5, Germany. Dec. 2, 2021. (This reference was cited in a prior Information Disclosure Statement. However, the relevant date was missing. The date has now been added.).
Meng et al., "Accurate Recovery of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019. (This reference was cited in a prior Information Disclosure Statement. However, the relevant date was missing. The date has now been added.).
Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019. (This reference was cited in a prior Information Disclosure Statement. However, the relevant date was missing. The date has now been added.).
International Search Report and Written Opinion dated Nov. 8, 2022 in PCT Application Serial No. PCT US/2022/039678.
International Search Report and Written Opinion, PCT Application Serial No. PCT/US2022/047751 issued Feb. 10, 2023, by the European Patent Office.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
Mcateer, James A., et al. "Ultracal-30 Gypsum Artificial Stones for Research on the Mechinisms of Stone Breakage in Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 577-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PHD Thesis, 2009, Cranfield University.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies A Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.

(56) References Cited

OTHER PUBLICATIONS

Zheng, W., "Optical Lenses Manufactured on Fiber Ends", IEEE, 2015, Splicer Engineering, Duncan SC USA.

Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.

"The New Optiguide DCYL700 Fiber Optic Diffuser Series", Optiguide Fiber Optic Spec Sheet, Pinnacle Biologics, 2014, Pinnacle Biologics, Illinois, USA.

Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.

Oshita, D., et al. "Characteristic of Cavitation Bubbles and Shock Waves Generated by Pulsed Electric Discharges with Different Voltages", IEEE, 2012, pp. 102-105, Kumamoto, Japan.

Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.

Murray, A., et al. "Peripheral laser angioplasty with pulsed dye laser and ball tipped optical fibres", The Lancet, 1989, pp. 1471-1474, vol. 2, Issue 8678-8679.

Mohammadzadeh, M., et al. "Photoacoustic Shock Wave Emission and Cavitation from Structured Optical Fiber Tips", Applied Physics Letters, 2016, vol. 108, American Institute of Physics Publishing LLC.

Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.

Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.

Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.

Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.

Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.

Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.

Lee, Seung H., et al. "Radial-firing optical fiber tip containing conical-shaped air-pocket for biomedical applications", Optics Express, 2015, vol. 23, No. 16, Optical Society of America.

Hui, C., et al. "Research on sound fields generated by laser-induced liquid breakdown", Optica Applicata, 2010, pp. 898-907, vol. XL, No. 4, Xi'an, China.

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

Roberts, Randy M., et al. "The Energy Partition of Underwater Sparks", The Journal of the Acoustical Society of America, 1996, pp. 3465-3475, vol. 99, No. 6, Acoustical Society of America.

Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.

Scepanovic, Obrad R., et al. "Multimodal spectroscopy detects features of vulnerable atherosclerotic plaque", Journal of Biomedical Optics, 2011, pp. 1-10, vol. 16, No. 1, SPIE.

Serruys, p. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.

Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.

Vogel, A., et al. "Shock-Wave Energy and Acoustic Energy Dissipation After Laser-induced Breakdown", SPIE, 1998, pp. 180-189, vol. 3254, SPIE.

"Laser Beam Couplers series 60SMS—for coupling into single-mode and polarization-maintaining fiber cables". Product for sale by Schafter+Kirchhoff, https://www.sukhamburg.com/. Copyright 2020.

International Search Report and Written Opinion dated Apr. 4, 2022 in PCT Application Serial No. PCT/US2021/062170.

International Search Report and Written Opinion dated Apr. 4, 2022 in PCT Application Serial No. PCT/US2021/065073.

Partial Search Report and Provisional Opinion dated May 3, 2022 in PCT Application No. PCT/US2022/015577.

International Search Report and Written Opinion dated May 13, 2022 in PCT Application Serial No. PCT/US2022/017562.

International Search Report and Written Opinion dated Aug. 25, 2022 in PCT Application Serial No. PCT US/2022/028035.

International Search Report and Written Opinion dated Sep. 15, 2022 in PCT Application Serial No. PCT US/2022/032045.

International Search Report and Written Opinion dated Feb. 19, 2021 in PCT Application Serial No. PCT/US2020/059960.

AccuCoat, "Beamsplitter: Divide, combine & conquer"; 2023.

Lin et al., "Photoacoustic imaging", Science Direct; 2021.

Zhou et al., "Photoacoustic Imaging with fiber optic technology: A review", Science Direct; 2020.

International Search Report and Written Opinion issued by the European Patent Office, for Serial No. PCT/US2022/053775, dated Apr. 21, 2023.

International Search Report and Written Opinion issued by the European Patent Office, for Serial No. PCT/US2023/011497, dated Apr. 28, 2023.

International Search Report and Written Opinion issued by the European Patent Office, for Serial No. PCT/US2023/012599, dated May 19, 2023.

PathFinder Digital, "Free Space Optics vs. Fiber Optics", 2023.

International Search Report and Written Opinion, issued in Application Serial No. PCT/US2023/016152, dated Jul. 12, 2023.

Shen, Yajie et al. "High-peak-power and narrow-linewidth Q-switched Ho: YAG laser in-band pumped at 1931 nm." Applied Physics Express 13.5 (2020): 052006. (Year 2020).

"Custom Medical Skived Tubing", Duke Extrusion, 2025. https://www.dukeextrusion.com/tubing-options/skived-tubing.

* cited by examiner

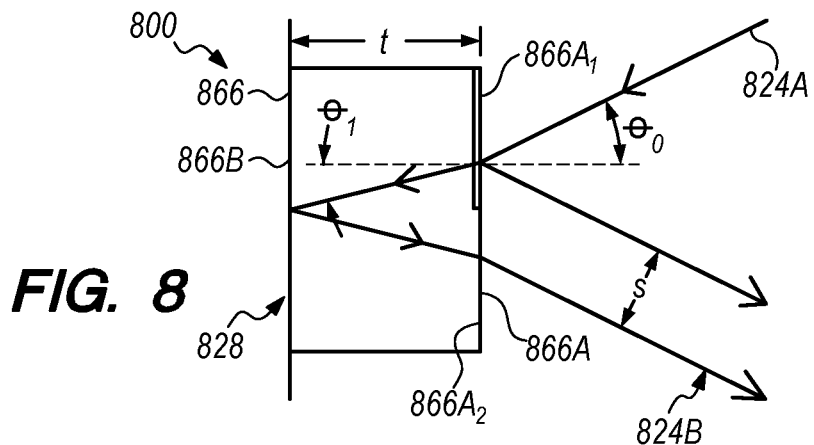
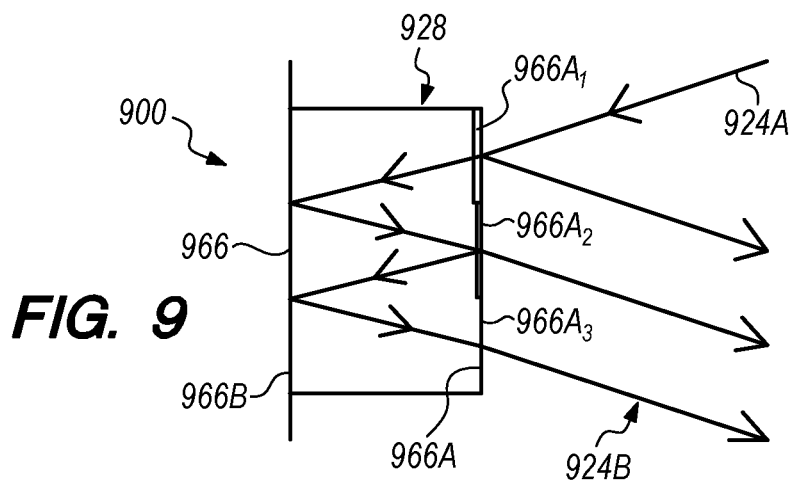
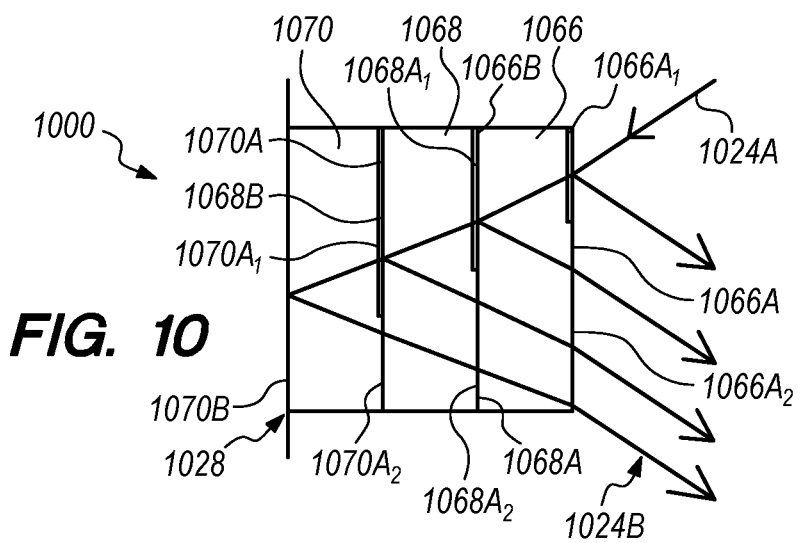

MULTIPLEXER FOR LASER-DRIVEN INTRAVASCULAR LITHOTRIPSY DEVICE

RELATED APPLICATIONS

This application claims priority on U.S. Provisional Application Ser. No. 62/950,014, filed on Dec. 18, 2019; and U.S. Provisional Application Ser. No. 63/013,975, filed on Apr. 22, 2020. As far as permitted, the contents of U.S. patent application Ser. No. 17/118,427 and U.S. Provisional Application Ser. Nos. 62/950,014 and 63/013,975 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions, such as severely calcified vascular lesions, can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

Intravascular lithotripsy is one method that has been recently used with some success for breaking up vascular lesions within vessels in the body. Intravascular lithotripsy utilizes a combination of pressure waves and bubble dynamics that are generated intravascularly in a fluid-filled balloon catheter. In particular, during an intravascular lithotripsy treatment, a high energy source is used to generate plasma and ultimately pressure waves as well as a rapid bubble expansion within a fluid-filled balloon to crack calcification at a treatment site within the vasculature that includes one or more vascular lesions. The associated rapid bubble formation from the plasma initiation and resulting localized fluid velocity within the balloon transfers mechanical energy through the incompressible fluid to impart a fracture force on the intravascular calcium, which is opposed to the balloon wall. The rapid change in fluid momentum upon hitting the balloon wall is known as hydraulic shock, or water hammer.

There is an ongoing desire to enhance vessel patency and optimization of therapy delivery parameters within an intravascular lithotripsy catheter system.

SUMMARY

The present invention is directed toward a catheter system for placement within a blood vessel having a vessel wall. The catheter system can be used for treating a vascular lesion within or adjacent to the vessel wall within a body of a patient. The catheter system includes a single light source that generates light energy. In various embodiments, the catheter system includes a first light guide and a second light guide, and a multiplexer. The first light guide and the second light guide are each configured to selectively receive light energy from the light source. The multiplexer receives the light energy from the light source in the form of a source beam and selectively directs the light energy from the light source in the form of individual guide beams to each of the first light guide and the second light guide.

In certain embodiments, the catheter system is configured such that the multiplexer receives the light energy from the light source and simultaneously directs the light energy from the light source in the form of individual guide beams to each of the first light guide and the second light guide. Alternatively, in other embodiments, the catheter system is configured such that the multiplexer receives the light energy from the light source and sequentially directs the light energy from the light source in the form of individual guide beams to each of the first light guide and the second light guide.

In some embodiments, the catheter system further includes a system controller including a processor that is configured to control operation of the light source to generate a single source beam in the form of pulses of light energy. Additionally, the system controller can be further configured to control operation of the multiplexer so that a first guide beam is directed to the first light guide and a second guide beam is directed to the second light guide.

In one embodiment, the light source includes a laser.

In certain embodiments, the catheter system further includes a catheter shaft and a balloon that is coupled to the catheter shaft, the balloon including a balloon wall that defines a balloon interior, the balloon being configured to retain a balloon fluid within the balloon interior. In such embodiments, the first light guide and the second light guide are positioned at least partially within the balloon interior. For example, each of the first light guide and the second light guide can include a guide distal end that is positioned within the balloon interior.

In some embodiments, the balloon is selectively inflatable with the balloon fluid to expand to an inflated state, wherein when the balloon is in the inflated state the balloon wall is configured to be positioned substantially adjacent to the vascular lesion. Additionally, in certain such embodiments, the first light guide and the second light guide receive the light energy from the light source and guide the light energy from the light source into the balloon interior to generate plasma in the balloon fluid within the balloon interior, the plasma generation causing rapid bubble formation and imparting pressure waves upon the balloon wall adjacent to the vascular lesion.

In certain embodiments, the multiplexer includes an optical element that splits the source beam into a first guide beam and a second guide beam. In some such embodiments, the multiplexer further includes coupling optics that are configured to focus the first guide beam onto the first light guide and the second guide beam onto the second light guide. Additionally, in such embodiments, the first guide beam and the second guide beam can be incident on the coupling optics with an angle between them.

In some embodiments, the optical element is provided in the form of a beamsplitter that splits the source beam into the first guide beam and the second guide beam. In such embodiments, the first guide beam is directed from the beamsplitter toward the coupling optics; and the second guide beam is directed from the beamsplitter toward a redirector that is positioned to redirect the second guide beam toward the coupling optics. Additionally, the coupling optics are configured to focus the first guide beam onto the first light guide and to focus the second guide beam onto the second light guide.

In other embodiments, the optical element includes an input surface that is partially reflective, a rear surface, and an exit surface that is anti-reflective. In such embodiments, the source beam impinging on the input surface splits the source beam into the first guide beam that is directed toward the coupling optics, and the second guide beam that is transmitted through the input surface toward the rear surface, reflects off of the rear surface and is directed through the exit surface and toward the coupling optics. In one such embodiment, the optical element is an imperfect parallelogram.

In still other embodiments, the optical element includes a polarizing beamsplitter that receives the source beam and splits the source beam into the first guide beam having a first polarization and the second guide beam having a second polarization that is different than the first polarization. In such embodiments, the multiplexer can further include a plurality of redirectors that redirect each of the first guide beam and the second guide beam before each of the first guide beam and the second guide beam are directed again toward the polarizing beamsplitter. In one such embodiment, the plurality of redirectors includes four ring mirrors. In another such embodiment, the plurality of redirectors includes two corner cubes. In still another such embodiment, the plurality of redirectors includes a first reflective surface and a second reflective surface; and the beamsplitter, the first reflective surface and the second reflective surface can all be integrated into a single optical element.

Additionally, in various such embodiments, the plurality of redirectors are positioned and aligned relative to one another such that the first guide beam and the second guide beam are one of (i) colinear and overlapping, such that the guide beams can be recombined and directed toward one of the first light guide and the second light guide; (ii) parallel and non-overlapping, such that the first guide beam is directed toward the first light guides and the second guide beam is directed toward the second light guide; and (iii) propagating at a small angle relative to one another, such that the first guide beam can be focused with coupling optics toward the first light guide, and the second guide beam can be focused with the coupling optics toward the second light guide.

The present invention is further directed toward a method for treating a vascular lesion within or adjacent to a vessel wall within a body of a patient, the method comprising the steps of generating light energy with a single light source; receiving the light energy from the light source in the form of a source beam with a multiplexer; and directing the light energy from the light source with the multiplexer in the form of individual guide beams to each of a first light guide and a second light guide.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 8 is a simplified schematic illustration of a portion of still another embodiment of the catheter system including still another embodiment of the multiplexer;

FIG. 9 is a simplified schematic illustration of a portion of another embodiment of the catheter system including another embodiment of the multiplexer;

FIG. 10 is a simplified schematic illustration of a portion of yet another embodiment of the catheter system including yet another embodiment of the multiplexer;

Figure 1:
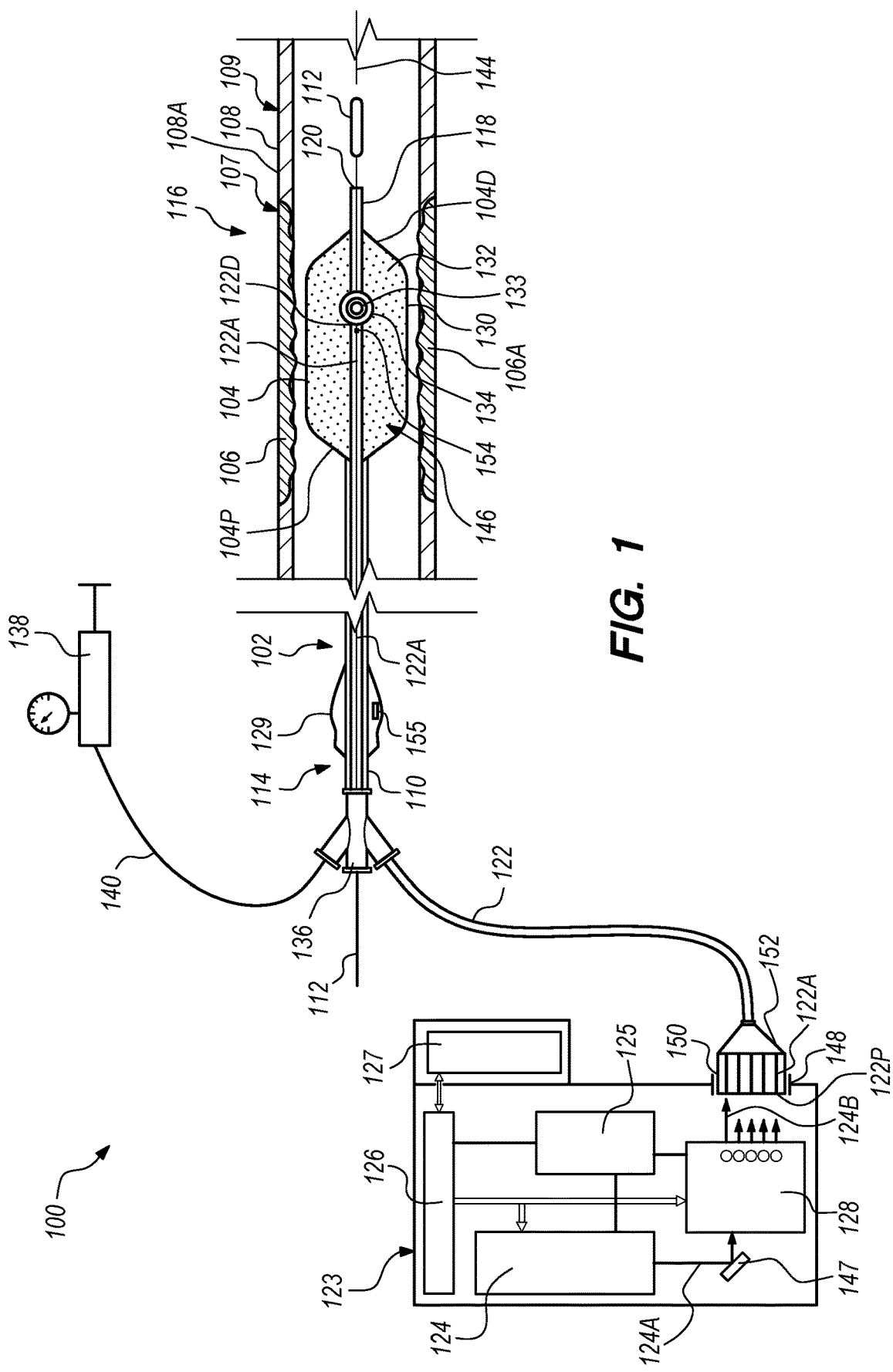
FIG. 1 is a schematic cross-sectional view of an embodiment of a catheter system in accordance with various embodiments herein, the catheter system including a plurality of light guides and a multiplexer.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

For the treatment of vascular lesions, such as calcium deposits in arteries, it is generally beneficial to be able to treat multiple closely spaced areas with a single insertion and positioning of a catheter balloon. To allow this to occur within an optical excitation system, such as within a laser-driven intravascular lithotripsy device, it is usually desirable to have a number of output channels, e.g., optical fibers and targets, for the treatment process, which can be distributed within the balloon. Since a high-power laser source is often the largest and most expensive component in the system, having a dedicated laser source for each optical fiber is unlikely to be feasible for a number of reasons including packaging requirements, power consumption, thermal considerations, and economics. For such reasons, it can be advantageous to multiplex a single laser simultaneously and/or sequentially into a number of different optical fibers for treatment purposes. This allows the possibility for using all or a particular portion of the laser power from the single laser with each fiber.

Thus, the catheter systems and related methods are configured to provide a means to power multiple fiber optic channels in a laser-driven pressure wave-generating device that is designed to impart pressure onto and induce fractures in vascular lesions, such as calcified vascular lesions and/or fibrous vascular lesions, using a single light source. More particularly, the present invention includes a multiplexer that multiplexes a single light source, e.g., a single laser source, into one or more of multiple light guides, e.g., fiber optic channels, in a single-use device.

One of the problems of using optical fibers to transfer high-energy optical pulses is that there can be significant limitations on the amount of energy that can be carried by the optical fiber due to both physical damage concerns and nonlinear processes such as Stimulated Brillouin Scattering (SBS). For this reason, it may be advantageous to have the option of accessing multiple fibers, i.e. light guides, simultaneously in order to increase the amount of energy that can be delivered at one time without directing excessive energy through any single fiber. The present invention further allows a single, stable light source to be channeled sequentially through a plurality of light guides with a variable number.

In various embodiments, the catheter systems and related methods disclosed herein can include a catheter configured to advance to vascular lesions, such as calcified vascular lesions or a fibrous vascular lesions, located at a treatment site within or adjacent a blood vessel within a body of a patient. The catheter includes a catheter shaft, and an inflatable balloon that is coupled and/or secured to the catheter shaft. The balloon can include a balloon wall that defines a balloon interior. The balloon can be configured to receive a balloon fluid within the balloon interior to expand from a deflated state suitable for advancing the catheter through a patient's vasculature, to an inflated state suitable for anchoring the catheter in position relative to the treatment site.

The catheter systems also include the plurality of light guides disposed along the catheter shaft and within the balloon interior of the balloon. Each light guide can be configured for generating pressure waves within the balloon for disrupting the vascular lesions. In particular, the catheter systems utilize light energy from the light source to create a localized plasma in the balloon fluid within the balloon interior of the balloon at or near a guide distal end of the light guide disposed in the balloon located at the treatment site. As such, the light guide can sometimes be referred to as, or can be said to incorporate a "plasma generator" at or near the guide distal end of the light guide that is positioned within the balloon interior of the balloon located at the treatment site. The creation of the localized plasma can initiate a pressure wave and can initiate the rapid formation of one or more high energy bubbles that can rapidly expand to a maximum size and then dissipate through a cavitation event that can launch a pressure wave upon collapse. The rapid expansion of the plasma-induced bubbles can generate one or more pressure waves within the balloon fluid retained within the balloon interior of the balloon and thereby impart pressure waves onto and induce fractures in the vascular lesions at the treatment site within or adjacent to the blood vessel wall within the body of the patient. It is appreciated that the guide distal end of each of the plurality of light guides can be positioned in any suitable locations relative to a length of the balloon to more effectively and precisely impart pressure waves for purposes of disrupting the vascular lesions at the treatment site.

In some embodiments, the light source can be configured to provide sub-millisecond pulses of light energy to initiate the plasma formation in the balloon fluid within the balloon to cause rapid bubble formation and to impart pressure waves upon the balloon wall at the treatment site. Thus, the pressure waves can transfer mechanical energy through an incompressible balloon fluid to the treatment site to impart a fracture force on the vascular lesions. Without wishing to be bound by any particular theory, it is believed that the rapid change in balloon fluid momentum upon the balloon wall that is in contact with the intravascular lesion is transferred to the intravascular lesion to induce fractures to the lesion.

Importantly, as noted above, the catheter systems and related methods include the multiplexer that multiplexes a single light source into one or more of the light guides in a single-use device to enable the treatment of multiple closely spaced areas with a single insertion and positioning of a catheter balloon.

As used herein, the terms "intravascular lesion" and "vascular lesion" are used interchangeably unless otherwise noted. As such, the intravascular lesions and/or the vascular lesions are sometimes referred to herein simply as "lesions".

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same or similar nomenclature and/or reference indicators will be used throughout the drawings and the following detailed description to refer to the same or like parts.

In the interest of clarity, not all of the routine features of the implementations described herein are shown and described. It is appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

The catheter systems disclosed herein can include many different forms. Referring now to FIG. 1, a schematic cross-sectional view is shown of a catheter system 100 in accordance with various embodiments. The catheter system 100 is suitable for imparting pressure waves to induce fractures in one or more vascular lesions within or adjacent a vessel wall of a blood vessel within a body of a patient. In the embodiment illustrated in FIG. 1, the catheter system 100 can include one or more of a catheter 102, a light guide bundle 122 including one or more (and preferably a plurality of) light guides 122A, a source manifold 136, a fluid pump 138, a system console 123 including one or more of a light source 124, a power source 125, a system controller 126, a graphic user interface 127 (a "GUI"), and a multiplexer 128, and a handle assembly 129. Alternatively, the catheter system 100 can include more components or fewer components than those specifically illustrated and described in relation to FIG. 1.

The catheter 102 is configured to move to a treatment site 106 within or adjacent to a vessel wall 108A of a blood vessel 108 within a body 107 of a patient 109. The treatment site 106 can include one or more vascular lesions 106A such as calcified vascular lesions, for example. Additionally, or in the alternative, the treatment site 106 can include vascular lesions 106A such as fibrous vascular lesions.

The catheter 102 can include an inflatable balloon 104 (sometimes referred to herein simply as a "balloon"), a catheter shaft 110 and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118 which is configured to move over the guidewire 112. As utilized herein, the guidewire lumen 118 defines a conduit through which the guidewire 112 extends. The catheter shaft 110 can further include an inflation lumen (not shown) and/or various other lumens for various other purposes. In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The balloon 104 includes a balloon wall 130 that defines a balloon interior 146. The balloon 104 can be selectively inflated with a balloon fluid 132 to expand from a deflated state suitable for advancing the catheter 102 through a patient's vasculature, to an inflated state (as shown in FIG. 1) suitable for anchoring the catheter 102 in position relative to the treatment site 106. Stated in another manner, when the balloon 104 is in the inflated state, the balloon wall 130 of the balloon 104 is configured to be positioned substantially adjacent to the treatment site 106, i.e. to the vascular lesion(s) 106A at the treatment site 106. It is appreciated that although FIG. 1 illustrates the balloon wall 130 of the balloon 104 being shown spaced apart from the treatment site 106 of the blood vessel 108 when in the inflated state, this is done merely for ease of illustration. It is recognized that the balloon wall 130 of the balloon 104 will typically be substantially directly adjacent to and/or abutting the treatment site 106 when the balloon 104 is in the inflated state.

The balloon 104 suitable for use in the catheter system 100 includes those that can be passed through the vasculature of a patient 109 when in the deflated state. In some embodiments, the balloon 104 is made from silicone. In other embodiments, the balloon 104 can be made from polydimethylsiloxane (PDMS), polyurethane, polymers such as PEBAX™ material, nylon, or any other suitable material.

The balloon 104 can have any suitable diameter (in the inflated state). In various embodiments, the balloon 104 can have a diameter (in the inflated state) ranging from less than one millimeter (mm) up to 25 mm. In some embodiments, the balloon 104 can have a diameter (in the inflated state) ranging from at least 1.5 mm up to 14 mm. In some embodiments, the balloons 104 can have a diameter (in the inflated state) ranging from at least two mm up to five mm.

In some embodiments, the balloon 104 can have a length ranging from at least three mm to 300 mm. More particularly, in some embodiments, the balloon 104 can have a length ranging from at least eight mm to 200 mm. It is appreciated that a balloon 104 having a relatively longer length can be positioned adjacent to larger treatment sites 106, and, thus, may be usable for imparting pressure waves onto and inducing fractures in larger vascular lesions 106A or multiple vascular lesions 106A at precise locations within the treatment site 106. It is further appreciated that a longer balloon 104 can also be positioned adjacent to multiple treatment sites 106 at any one given time.

The balloon 104 can be inflated to inflation pressures of between approximately one atmosphere (atm) and 70 atm. In some embodiments, the balloon 104 can be inflated to inflation pressures of from at least 20 atm to 60 atm. In other embodiments, the balloon 104 can be inflated to inflation pressures of from at least six atm to 20 atm. In still other embodiments, the balloon 104 can be inflated to inflation pressures of from at least three atm to 20 atm. In yet other embodiments, the balloon 104 can be inflated to inflation pressures of from at least two atm to ten atm.

The balloon 104 can have various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloon 104 can include a drug eluting coating or a drug eluting stent structure. The drug eluting coating or drug eluting stent can include one or more therapeutic agents including anti-inflammatory agents, anti-neoplastic agents, anti-angiogenic agents, and the like.

The balloon fluid 132 can be a liquid or a gas. Some examples of the balloon fluid 132 suitable for use can include, but are not limited to one or more of water, saline, contrast medium, fluorocarbons, perfluorocarbons, gases, such as carbon dioxide, or any other suitable balloon fluid 132. In some embodiments, the balloon fluid 132 can be used as a base inflation fluid. In some embodiments, the balloon fluid 132 can include a mixture of saline to contrast medium in a volume ratio of approximately 50:50. In other embodiments, the balloon fluid 132 can include a mixture of saline to contrast medium in a volume ratio of approximately 25:75. In still other embodiments, the balloon fluid 132 can include a mixture of saline to contrast medium in a volume ratio of approximately 75:25. However, it is understood that any suitable ratio of saline to contrast medium can be used. The balloon fluid 132 can be tailored on the basis of composition, viscosity, and the like so that the rate of travel of the pressure waves are appropriately manipulated. In certain embodiments, the balloon fluid 132 suitable for use herein is biocompatible. A volume of balloon fluid 132 can be tailored by the chosen light source 124 and the type of balloon fluid 132 used.

In some embodiments, the contrast agents used in the contrast media can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as perfluorocarbon dodecafluoropentane (DDFP, C5F12).

The balloon fluids 132 can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 µm) of the electromagnetic spectrum. Suitable absorptive agents can include those with absorption maxima along the spectrum from at least ten nm to 2.5 µm. Alternatively, the balloon fluid 132 can include absorptive agents that can selectively absorb light in the mid-infrared region (e.g., at least 2.5 µm to 15 µm), or the far-infrared region (e.g., at least 15 µm to one mm) of the electromagnetic spectrum. In various embodiments, the absorptive agent can be those that have an absorption maximum matched with the emission maximum of the laser used in the catheter system 100. By way of non-limiting examples, various lasers described herein can include neodymium:yttrium-aluminum-garnet (Nd:YAG–emission maximum=1064 nm) lasers, holmium: YAG (Ho:YAG–emission maximum=2.1 µm) lasers, or erbium:YAG (Er:YAG–emission maximum=2.94 µm) lasers. In some embodiments, the absorptive agents can be water soluble. In other embodiments, the absorptive agents are not water soluble. In some embodiments, the absorptive agents used in the balloon fluids 132 can be tailored to match the peak emission of the light source 124. Various light sources 124 having emission wavelengths of at least ten nanometers to one millimeter are discussed elsewhere herein.

The catheter shaft 110 of the catheter 102 can be coupled to the one or more light guides 122A of the light guide bundle 122 that are in optical communication with the light source 124. The light guide(s) 122A can be disposed along the catheter shaft 110 and within the balloon 104. Each of the light guides 122A can have a guide distal end 122D that is at any suitable longitudinal position relative to a length of the balloon 104. In some embodiments, each light guide 122A can be an optical fiber and the light source 124 can be a laser. The light source 124 can be in optical communication with the light guides 122A at the proximal portion 114 of the catheter system 100. More particularly, as described in detail herein, the light source 124 can selectively, simultaneously, sequentially and/or alternatively be in optical communication with each of the light guides 122A in any desired combination, order and/or pattern due to the presence and operation of the multiplexer 128.

In some embodiments, the catheter shaft 110 can be coupled to multiple light guides 122A such as a first light guide, a second light guide, a third light guide, etc., which can be disposed at any suitable positions about the guidewire lumen 118 and/or the catheter shaft 110. For example, in certain non-exclusive embodiments, two light guides 122A can be spaced apart by approximately 180 degrees about the circumference of the guidewire lumen 118 and/or the catheter shaft 110; three light guides 122A can be spaced apart by approximately 120 degrees about the circumference of the guidewire lumen 118 and/or the catheter shaft 110; or four light guides 122A can be spaced apart by approximately 90 degrees about the circumference of the guidewire lumen 118 and/or the catheter shaft 110. Still alternatively, multiple light guides 122A need not be uniformly spaced apart from one another about the circumference of the guidewire lumen 118 and/or the catheter shaft 110. More particularly, the light guides 122A can be disposed either uniformly or non-uniformly about the guidewire lumen 118 and/or the catheter shaft 110 to achieve the desired effect in the desired locations.

The catheter system 100 and/or the light guide bundle 122 can include any number of light guides 122A in optical communication with the light source 124 at the proximal portion 114, and with the balloon fluid 132 within the balloon interior 146 of the balloon 104 at the distal portion 116. For example, in some embodiments, the catheter system 100 and/or the light guide bundle 122 can include from one light guide 122A to five light guides 122A. In other embodiments, the catheter system 100 and/or the light guide bundle 122 can include from five light guides 122A to fifteen light guides 122A. In yet other embodiments, the catheter system 100 and/or the light guide bundle 122 can include from ten light guides 122A to thirty light guides 122A. Alternatively, in still other embodiments, the catheter system 100 and/or the light guide bundle 122 can include greater than 30 light guides 122A.

The light guides 122A can have any suitable design for purposes of generating plasma and/or pressure waves in the balloon fluid 132 within the balloon interior 146. In certain embodiments, the light guides 122A can include an optical fiber or flexible light pipe. The light guides 122A can be thin and flexible and can allow light signals to be sent with very little loss of strength. The light guides 122A can include a core surrounded by a cladding about its circumference. In some embodiments, the core can be a cylindrical core or a partially cylindrical core. The core and cladding of the light guides 122A can be formed from one or more materials, including but not limited to one or more types of glass, silica, or one or more polymers. The light guides 122A may also include a protective coating, such as a polymer. It is appreciated that the index of refraction of the core will be greater than the index of refraction of the cladding.

Each light guide 122A can guide light energy along its length from a guide proximal end 122P to the guide distal end 122D having at least one optical window (not shown) that is positioned within the balloon interior 146.

The light guides 122A can assume many configurations about and/or relative to the catheter shaft 110 of the catheter 102. In some embodiments, the light guides 122A can run parallel to the longitudinal axis 144 of the catheter shaft 110. In some embodiments, the light guides 122A can be physically coupled to the catheter shaft 110. In other embodiments, the light guides 122A can be disposed along a length of an outer diameter of the catheter shaft 110. In yet other embodiments, the light guides 122A can be disposed within one or more light guide lumens within the catheter shaft 110.

The light guides 122A can also be disposed at any suitable positions about the circumference of the guidewire lumen 118 and/or the catheter shaft 110, and the guide distal end 122D of each of the light guides 122A can be disposed at any suitable longitudinal position relative to the length of the balloon 104 and/or relative to the length of the guidewire lumen 118 to more effectively and precisely impart pressure waves for purposes of disrupting the vascular lesions 106A at the treatment site 106.

In certain embodiments, the light guides 122A can include one or more photoacoustic transducers 154, where each photoacoustic transducer 154 can be in optical communication with the light guide 122A within which it is disposed. In some embodiments, the photoacoustic transducers 154 can be in optical communication with the guide distal end 122D of the light guide 122A. Additionally, in such embodiments, the photoacoustic transducers 154 can have a shape that corresponds with and/or conforms to the guide distal end 122D of the light guide 122A.

The photoacoustic transducer 154 is configured to convert light energy into an acoustic wave at or near the guide distal end 122D of the light guide 122A. The direction of the acoustic wave can be tailored by changing an angle of the guide distal end 122D of the light guide 122A.

In certain embodiments, the photoacoustic transducers 154 disposed at the guide distal end 122D of the light guide 122A can assume the same shape as the guide distal end 122D of the light guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. The light guide 122A can further include additional photoacoustic transducers 154 disposed along one or more side surfaces of the length of the light guide 122A.

In some embodiments, the light guides 122A can further include one or more diverting features or "diverters" (not shown in FIG. 1) within the light guide 122A that are configured to direct light to exit the light guide 122A toward a side surface which can be located at or near the guide distal end 122D of the light guide 122A, and toward the balloon wall 130. A diverting feature can include any feature of the system that diverts light energy from the light guide 122A away from its axial path toward a side surface of the light guide 122A. Additionally, the light guides 122A can each include one or more light windows disposed along the longitudinal or circumferential surfaces of each light guide 122A and in optical communication with a diverting feature. Stated in another manner, the diverting features can be configured to direct light energy in the light guide 122A toward a side surface that is at or near the guide distal end 122D, where the side surface is in optical communication with a light window. The light windows can include a portion of the light guide 122A that allows light energy to exit the light guide 122A from within the light guide 122A, such as a portion of the light guide 122A lacking a cladding material on or about the light guide 122A.

Examples of the diverting features suitable for use include a reflecting element, a refracting element, and a fiber diffuser. The diverting features suitable for focusing light energy away from the tip of the light guides 122A can include, but are not to be limited to, those having a convex surface, a gradient-index (GRIN) lens, and a mirror focus lens. Upon contact with the diverting feature, the light energy is diverted within the light guide 122A to one or more of a plasma generator 133 and the photoacoustic transducer 154 that is in optical communication with a side surface of the light guide 122A. As noted, the photoacoustic transducer 154 then converts light energy into an acoustic wave that extends away from the side surface of the light guide 122A.

The source manifold 136 can be positioned at or near the proximal portion 114 of the catheter system 100. The source manifold 136 can include one or more proximal end openings that can receive the one or more light guides 122A of the light guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132, i.e. via the inflation conduit 140, as needed.

As noted above, in the embodiment illustrated in FIG. 1, the system console 123 includes one or more of the light source 124, the power source 125, the system controller 126, the GUI 127, and the multiplexer 128. Alternatively, the system console 123 can include more components or fewer components than those specifically illustrated in FIG. 1. For example, in certain non-exclusive alternative embodiments, the system console 123 can be designed without the GUI 127. Still alternatively, one or more of the light source 124, the power source 125, the system controller 126, the GUI 127 and the multiplexer 128 can be provided within the catheter system 100 without the specific need for the system console 123.

As shown, the system console 123, and the components included therewith, is operatively coupled to the catheter 102, the light guide bundle 122, and the remainder of the catheter system 100. For example, in some embodiments, as illustrated in FIG. 1, the system console 123 can include a console connection aperture 148 (also sometimes referred to generally as a "socket") by which the light guide bundle 122 is mechanically coupled to the system console 123. In such embodiments, the light guide bundle 122 can include a guide coupling housing 150 (also sometimes referred to generally as a "ferrule") that houses a portion, e.g., the guide proximal end 122P, of each of the light guides 122A. The guide coupling housing 150 is configured to fit and be selectively retained within the console connection aperture 148 to provide the mechanical coupling between the light guide bundle 122 and the system console 123.

The light guide bundle 122 can also include a guide bundler 152 (or "shell") that brings each of the individual light guides 122A closer together so that the light guides 122A and/or the light guide bundle 122 can be in a more compact form as it extends with the catheter 102 into the blood vessel 108 during use of the catheter system 100.

The light source 124 can be selectively and/or alternatively coupled in optical communication with each of the light guides 122A, i.e. to the guide proximal end 122P of each of the light guides 122A, in the light guide bundle 122. In particular, the light source 124 is configured to generate light energy in the form of a source beam 124A, such as a pulsed source beam, that can be selectively and/or alternatively directed to and received by each of the light guides 122A in the light guide bundle 122 in any desired combination, order, sequence and/or pattern. More specifically, as described in greater detail herein below, the source beam 124A from the light source 124 is directed through the multiplexer 128 such that individual guide beams 124B (or "multiplexed beams") can be selectively and/or alternatively directed into and received by each of the light guides 122A in the light guide bundle 122. In particular, each pulse of the light source 124, i.e. each pulse of the source beam 124A, can be directed through the multiplexer 128 to generate one or more separate guide beams 124B (only one is shown in FIG. 1) that are selectively and/or alternatively directed to one or more of the light guides 122A in the light guide bundle 122.

The light source 124 can have any suitable design. In certain embodiments, the light source 124 can be configured to provide sub-millisecond pulses of light energy from the light source 124 that are focused onto a small spot in order to couple it into the guide proximal end 122P of the light guide 122A. Such pulses of light energy are then directed and/or guided along the light guides 122A to a location within the balloon interior 146 of the balloon 104, thereby inducing plasma formation in the balloon fluid 132 within the balloon interior 146 of the balloon 104, e.g., via the plasma generator 133 that can be located at the guide distal end 122D of the light guide 122A. In particular, the light emitted at the guide distal end 122D of the light guide 122A energizes the plasma generator 133 to form the plasma within the balloon fluid 132 within the balloon interior 146. The plasma formation causes rapid bubble formation, and imparts pressure waves upon the treatment site 106. An exemplary plasma-induced bubble 134 is illustrated in FIG. 1.

In various non-exclusive alternative embodiments, the sub-millisecond pulses of light energy from the light source 124 can be delivered to the treatment site 106 at a frequency of between approximately one hertz (Hz) and 5000 Hz, between approximately 30 Hz and 1000 Hz, between approximately ten Hz and 100 Hz, or between approximately one Hz and 30 Hz. Alternatively, the sub-millisecond pulses of light energy can be delivered to the treatment site 106 at a frequency that can be greater than 5000 Hz or less than one Hz, or any other suitable range of frequencies.

It is appreciated that although the light source 124 is typically utilized to provide pulses of light energy, the light source 124 can still be described as providing a single source beam 124A, i.e. a single pulsed source beam.

The light sources 124 suitable for use herein can include various types of light sources including lasers and lamps. Suitable lasers can include short pulse lasers on the sub-millisecond timescale. In some embodiments, the light source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid 132 of the catheter 102. In various non-exclusive alternative embodiments, the pulse widths can include those falling within a range including from at least ten ns to 3000 ns, at least 20 ns to 100 ns, or at least one ns to 500 ns. Alternatively, any other suitable pulse width range can be used.

Exemplary nanosecond lasers can include those within the UV to IR spectrum, spanning wavelengths of about ten nanometers (nm) to one millimeter (mm). In some embodiments, the light sources 124 suitable for use in the catheter system 100 can include those capable of producing light at wavelengths of from at least 750 nm to 2000 nm. In other embodiments, the light sources 124 can include those capable of producing light at wavelengths of from at least 700 nm to 3000 nm. In still other embodiments, the light sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter system 100 can generate pressure waves having maximum pressures in the range of at least one megapascal (MPa) to 100 MPa. The maximum pressure generated by a particular catheter system 100 will depend on the light source 124, the absorbing material, the bubble expansion, the propagation medium, the balloon material, and other factors. In various non-exclusive alternative embodiments, the catheter system 100 can generate pressure waves having maximum pressures in the range of at least approximately two MPa to 50 MPa, at least approximately two MPa to 30 MPa, or at least approximately 15 MPa to 25 MPa.

The pressure waves can be imparted upon the treatment site 106 from a distance within a range from at least approximately 0.1 millimeters (mm) to greater than approximately 25 mm extending radially from the energy guides 122A when the catheter 102 is placed at the treatment site 106. In various non-exclusive alternative embodiments, the pressure waves can be imparted upon the treatment site 106 from a distance within a range from at least approximately ten mm to 20 mm, at least approximately one mm to ten mm, at least approximately 1.5 mm to four mm, or at least approximately 0.1 mm to ten mm extending radially from the energy guides 122A when the catheter 102 is placed at the treatment site 106. In other embodiments, the pressure waves can be imparted upon the treatment site 106 from another suitable distance that is different than the foregoing ranges. In some embodiments, the pressure waves can be imparted upon the treatment site 106 within a range of at least approximately two MPa to 30 MPa at a distance from at least approximately 0.1 mm to ten mm. In some embodiments, the pressure waves can be imparted upon the treatment site 106 from a range of at least approximately two MPa to 25 MPa at a distance from at least approximately 0.1 mm to ten mm. Still alternatively, other suitable pressure ranges and distances can be used.

The power source 125 is electrically coupled to and is configured to provide necessary power to each of the light source 124, the system controller 126, the GUI 127, the multiplexer 128, and the handle assembly 129. The power source 125 can have any suitable design for such purposes.

The system controller 126 is electrically coupled to and receives power from the power source 125. Additionally, the system controller 126 is coupled to and is configured to control operation of each of the light source 124, the GUI 127 and the multiplexer 128. The system controller 126 can include one or more processors or circuits for purposes of controlling the operation of at least the light source 124, the GUI 127 and the multiplexer 128. For example, the system controller 126 can control the light source 124 for generating pulses of light energy as desired and/or at any desired firing rate. Subsequently, the system controller 126 can then control the multiplexer 128 so that the light energy from the light source 124, i.e. the source beam 124A, can be effectively and accurately multiplexed so as to be selectively and/or alternatively directed to each of the light guides 122A in the form of individual guide beams 124B in a desired manner.

The system controller 126 can further be configured to control operation of other components of the catheter system 100 such as the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 129.

The GUI 127 is accessible by the user or operator of the catheter system 100. Additionally, the GUI 127 is electrically connected to the system controller 126. With such design, the GUI 127 can be used by the user or operator to ensure that the catheter system 100 is effectively utilized to impart pressure onto and induce fractures into the vascular lesions 106A at the treatment site 106. The GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time during use of the catheter system 100. In various embodiments, the GUI 127 can include one or more colors, different sizes, varying brightness, etc., that may act as alerts to the user or operator. Additionally, or in the alternative, the GUI 127 can provide audio data or information to the user or operator. The specifics of the GUI 127 can vary depending upon the design requirements of the catheter system 100, or the specific needs, specifications and/or desires of the user or operator.

As provided herein, the multiplexer 128 is configured to selectively and/or alternatively direct light energy from the light source 124 to each of the light guides 122A in the light guide bundle 122. More particularly, the multiplexer 128 is configured to receive light energy from a single light source 124, such as a single source beam 124A from a single laser source, and selectively and/or alternatively direct such light energy in the form of individual guide beams 124B to each of the light guides 122A in the light guide bundle 122 in any desired combination (i.e. simultaneously direct light energy through multiple light guides 122A), sequence, order and/or pattern. As such, the multiplexer 128 enables a single light source 124 to be channeled simultaneously and/or sequentially through a plurality of light guides 122A such that the catheter system 100 is able to impart pressure onto and induce fractures in vascular lesions at the treatment site 106 within or adjacent to the vessel wall 108A of the blood vessel 108 in a desired manner. Additionally, as shown, the catheter system 100 can include one or more optical elements 147 for purposes of directing the light energy in the form of the source beam 124A from the light source 124 to the multiplexer 128.

The multiplexer 128 can have any suitable design for purposes of selectively and/or alternatively directing the light energy from the light source 124 to each of the light guides 122A of the light guide bundle 122. Various non-exclusive alternative embodiments of the multiplexer 128 are described in detail herein below in relation to FIGS. 2-23.

As shown in FIG. 1, the handle assembly 129 can be positioned at or near the proximal portion 114 of the catheter system 100, and/or near the source manifold 136. In this embodiment, the handle assembly 129 is coupled to the balloon 104 and is positioned spaced apart from the balloon 104. Alternatively, the handle assembly 129 can be positioned at another suitable location.

The handle assembly 129 is handled and used by the user or operator to operate, position and control the catheter 102. The design and specific features of the handle assembly 129 can vary to suit the design requirements of the catheter system 100. In the embodiment illustrated in FIG. 1, the handle assembly 129 is separate from, but in electrical and/or fluid communication with one or more of the system controller 126, the light source 124, the fluid pump 138, the GUI 127, and the multiplexer 128. In some embodiments, the handle assembly 129 can integrate and/or include at least a portion of the system controller 126 within an interior of the handle assembly 129. For example, as shown, in certain such embodiments, the handle assembly 129 can include circuitry 155 that can form at least a portion of the system controller 126. In one embodiment, the circuitry 155 can include a printed circuit board having one or more integrated circuits, or any other suitable circuitry. In an alternative embodiment, the circuitry 155 can be omitted, or can be included within the system controller 126, which in various embodiments can be positioned outside of the handle assembly 129, e.g., within the system console 123. It is understood that the handle assembly 129 can include fewer or additional components than those specifically illustrated and described herein.

Figure 2:
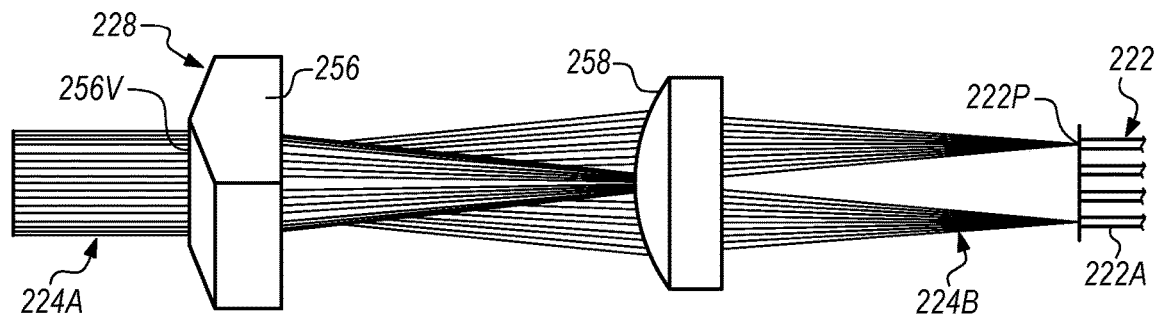
FIG. 2 is a simplified schematic illustration of a portion of an embodiment of the catheter system including an embodiment of the multiplexer.

FIG. 2 is a simplified schematic illustration of a portion of an embodiment of the catheter system 200 including an embodiment of the multiplexer 228. In particular, FIG. 2 illustrates a light guide bundle 222 including a plurality of light guides 222A; and the multiplexer 228 that receives light energy in the form of a source beam 224A, a pulsed source beam 224A in various embodiments, from the light source 124 (illustrated in FIG. 1) and simultaneously and/or sequentially directs the light energy in the form of individual guide beams 224B to at least two of the plurality of the light guides 222A. More specifically, the multiplexer 228 is configured to direct the light energy in the form of individual guide beams 224B onto a guide proximal end 222P of at least two of the plurality of light guides 222A. As such, as shown in FIG. 2, the multiplexer 228 is operatively and/or optically coupled in optical communication to the light guide bundle 222 and/or to the plurality of light guides 222A.

It is appreciated that the light guide bundle 222 can include any suitable number of light guides 222A, which can be positioned and/or oriented relative to one another in any suitable manner to best align the plurality of light guides 222A relative to the multiplexer 228. For example, in the embodiment illustrated in FIG. 2, the light guide bundle 222 includes four light guides 222A that are aligned in a linear arrangement relative to one another. The light guide bundle 222 and/or the light guides 222A are substantially similar in design and function as described in detail herein above. Accordingly, such components will not be described in detail in relation to the embodiment illustrated in FIG. 2.

The design of the multiplexer 228 can be varied depending on the requirements of the catheter system 200, the relative positioning of the light guides 222A, and/or to suit the desires of the user or operator of the catheter system 200. In the embodiment illustrated in FIG. 2, the multiplexer 228 includes one or more of a multi-faceted prism 256, and coupling optics 258. Alternatively, the multiplexer 228 can include more components or fewer components than those specifically illustrated in FIG. 2.

The multi-faceted prism 256 consists of a glass plate that is polished with multiple facets at a certain angle. The multi-faceted prism 256 can split the source beam 224A into a plurality of individual guide beams 224B that can each be coupled into one of the plurality of light guides 222A in the light guide bundle 222. More specifically, if the multi-faceted prism is positioned relative to the source beam 224A such that the source beam 224A is centered on a vertex 256V of the multi-faceted prism 256, then the multi-faceted prism 256 can equally split a parallel source beam 224A into the plurality of individual guide beams 224B. With such design, when the parallel source beam 224A passes through the multi-faceted prism 256, the multi-faceted prism 256 will split the source beam 224A into multiple guide beams 224B, of substantially equal energy, with different angles around the axis of the propagation direction. This allows light energy from a single light source 124 to be coupled into an array of parallel light guides 222A with guide proximal ends 222P located in the same plane.

It is appreciated that the source beam 224A will be split into two or more individual guide beams 224B depending on the number of facets included within the multi-faceted prism 256. For example, in the embodiment shown in FIG. 2, the multi-faceted prism 256 includes two facets so that the source beam 224A will be split into two individual guide beams 224B. In particular, in this embodiment, the source beam 224A is split in half into two "half-circle" guide beams 224B which cross at an angle defined by the refraction on the prism surfaces. Alternatively, the multi-faceted prism 256 can include more than two facets so that the source beam 224A will be split into more than two guide beams 224B.

Subsequently, the individual guide beams 224B are directed toward the coupling optics 258. The coupling optics 258 can have any suitable design for purposes of focusing the individual guide beams 224B to at least two of the light guides 222A. In one embodiment, the coupling optics 258 include a single focusing lens that is specifically configured to focus the individual guide beams 224B as desired. If two co-planar non-parallel guide beams 224B are incident on a single lens, the result at the focus of the coupling optics 258 in the form of the single lens, will be two focal spots with an offset related to the angle between the guide beams 224B and the focal length of the lens. More specifically, when the individual guide beams 224B pass through the single focusing lens of the coupling optics 258, the coupling optics 258 will focus the guide beams into multiple spots in a circle at the focal plane. Thus, the light will couple into multiple light guides 222A when the light guides 222A are aligned with the focal spots at the focal plane. Accordingly, it is appreciated that the angle and lens can be chosen to allow the two guide beams 224B to be effectively coupled into any pair of parallel light guides 222A. Alternatively, the coupling optics 258 can have another suitable design.

The advantage of this method is that the tolerances for partitioning the source beam 224A are primarily controlled by the optical fabrication of the multi-faceted prism 256 and the coupling optics 258. However, the main exception is the need to accurately position the multi-faceted prism 256 relative to the source beam 224A to ensure equal partitioning of the light energy of the source beam 224A.

Figure 3:
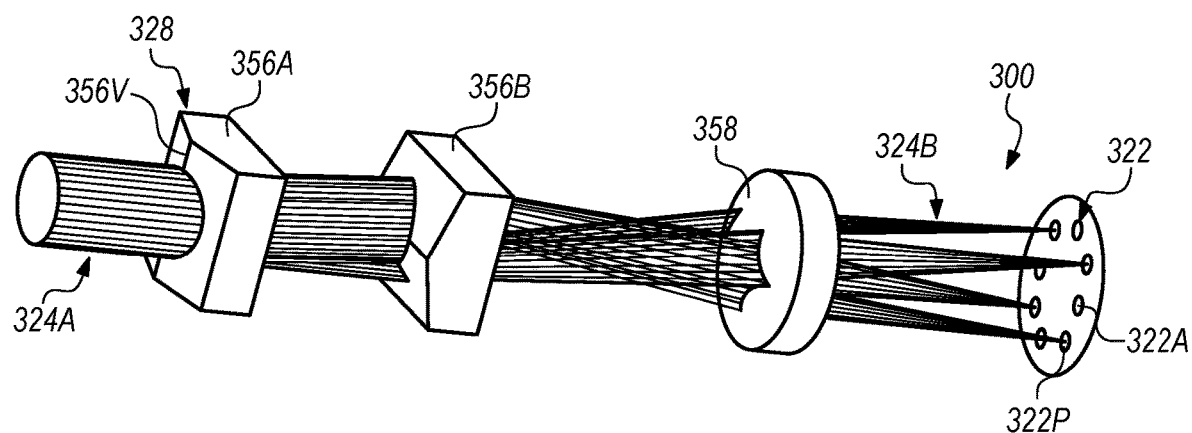
FIG. 3 is a simplified schematic illustration of a portion of another embodiment of the catheter system including another embodiment of the multiplexer.

FIG. 3 is a simplified schematic illustration of a portion of another embodiment of the catheter system 300 including another embodiment of the multiplexer 328. In particular, FIG. 3 illustrates a light guide bundle 322 including a plurality of light guides 322A; and the multiplexer 328 that receives light energy in the form of a source beam 324A, a pulsed source beam 324A in various embodiments, from the light source 124 (illustrated in FIG. 1) and simultaneously and/or sequentially directs the light energy in the form of individual guide beams 324B onto a guide proximal end 322P of at least two of the plurality of the light guides 322A. As such, as shown in FIG. 3, the multiplexer 328 is operatively and/or optically coupled in optical communication to the light guide bundle 322 and/or to the plurality of light guides 322A.

It is appreciated that the light guide bundle 322 can include any suitable number of light guides 322A, which can be positioned and/or oriented relative to one another in any suitable manner to best align the plurality of light guides 322A relative to the multiplexer 328. For example, in the embodiment illustrated in FIG. 3, the light guide bundle 322 includes eight light guides 322A that are aligned in a generally circular arrangement relative to one another. The light guide bundle 322 and/or the light guides 322A are substantially similar in design and function as described in detail herein above. Accordingly, such components will not be described in detail in relation to the embodiment illustrated in FIG. 3.

In this embodiment, the multiplexer 328 is somewhat similar to the embodiment illustrated and described in relation to FIG. 2. In particular, the multiplexer 328 again includes a first multi-faceted prism 356A, and coupling optics 358. However, in this embodiment, the multiplexer 328 further includes a second multi-faceted prism 356B, which is positioned in the beam path between the first multi-faceted prism 356A and the coupling optics 358.

As with the previous embodiment, the first multi-faceted prism 356A can be a two-faceted prism that splits the source beam 324A into two equal individual beams when the source beam 324A is centered on a vertex 356V of the first multi-faceted prism 356A. Subsequently, the two individual beams are directed through the second multi-faceted prism 356B. In this embodiment, the second multi-faceted prism 356B is also a two-faceted prism such that the two individual beams from the first multi-faceted prism 356A are each split such that the source beam 324A has now been split twice so as to provide four individual guide beams 324B. In one embodiment, the second multi-faceted prism 356B can be rotated relative to the first multi-faceted prism 356A, such as by approximately ninety degrees, such that the four individual guide beams 324B, when focused by the coupling optics 358, are arranged in a generally square pattern relative to one another. With such design, the four individual guide beams 324B can be effectively directed onto the guide proximal end 322P of four of the eight light guides 322A that are included within the light guide bundle 322. Alternatively, it is appreciated that the second multi-faceted prism 356B can be rotated by a different amount relative to the first multi-faceted prism 356A, i.e. more than or less than approximately ninety degrees, in order to have the individual guide beams 324B directed toward a different opposing pair of light guides within the light guide bundle 322. Still alternatively, each of the first multi-faceted prism 356A and the second multi-faceted prism 356B can have more than two facets such that the source beam 324A can be split into more than four individual guide beams 324B.

As with the previous embodiment, the coupling optics 358 can have any suitable design for purposes of focusing the four individual guide beams 324B onto four of the light guides 322A. In one embodiment, the coupling optics 358 can again include a single focusing lens that is specifically configured to focus the individual guide beams 324B as desired. Alternatively, the coupling optics 358 can have another suitable design.

Figure 4:
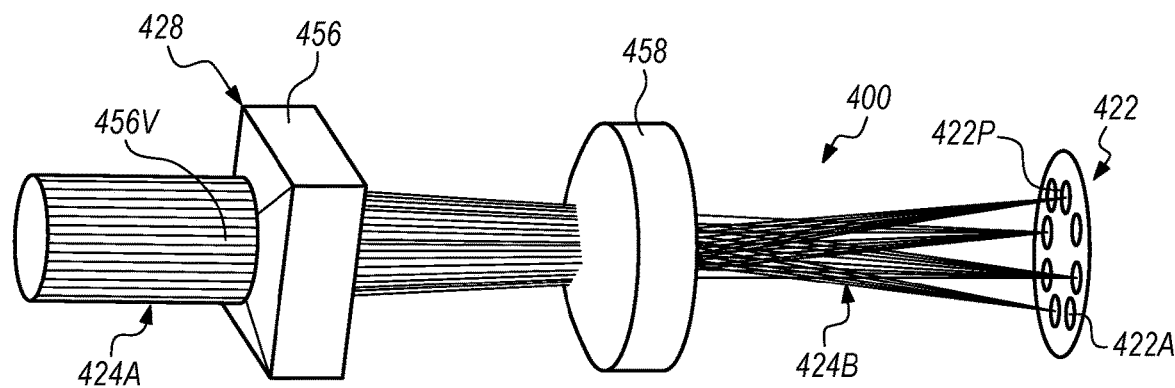
FIG. 4 is a simplified schematic illustration of a portion of still another embodiment of the catheter system including still another embodiment of the multiplexer.

FIG. 4 is a simplified schematic illustration of a portion of still another embodiment of the catheter system 400 including still another embodiment of the multiplexer 428. In particular, FIG. 4 illustrates a light guide bundle 422 including a plurality of light guides 422A; and the multiplexer 428 that receives light energy in the form of a source beam 424A, a pulsed source beam 424A in various embodiments, from the light source 124 (illustrated in FIG. 1) and simultaneously and/or sequentially directs the light energy in the form of individual guide beams 424B onto a guide proximal end 422P of at least two of the plurality of the light guides 422A. As such, as shown in FIG. 4, the multiplexer 428 is operatively and/or optically coupled in optical communication to the light guide bundle 422 and/or to the plurality of light guides 422A.

It is appreciated that the light guide bundle 422 can include any suitable number of light guides 422A, which can be positioned and/or oriented relative to one another in any suitable manner to best align the plurality of light guides 422A relative to the multiplexer 428. For example, in the embodiment illustrated in FIG. 4, the light guide bundle 422 again includes eight light guides 422A that are aligned in a generally circular arrangement relative to one another. The light guide bundle 422 and/or the light guides 422A are substantially similar in design and function as described in detail herein above. Accordingly, such components will not be described in detail in relation to the embodiment illustrated in FIG. 4.

In this embodiment, the multiplexer 428 is somewhat similar to the embodiment illustrated and described in relation to FIG. 2. In particular, the multiplexer 428 again includes a multi-faceted prism 456, and coupling optics 458. However, in this embodiment, the multi-faceted prism 456 is a four-faceted prism. As such, when the source beam 424A is centered on a vertex 456V of the multi-faceted prism 456, the multi-faceted prism 456 can equally split a parallel source beam 424A into four individual guide beams 424B with different angles around the axis of propagation.

Subsequently, the four individual guide beams 424B are directed toward the coupling optics 458. As with the previous embodiments, the coupling optics 458 can again include a single focusing lens that is configured to focus the individual guide beams 424B to be arranged in a generally square pattern relative to one another. With such design, the four individual guide beams 424B can be effectively directed onto the guide proximal end 422P of four of the eight light guides 422A that are included within the light guide bundle 422.

Figure 5:
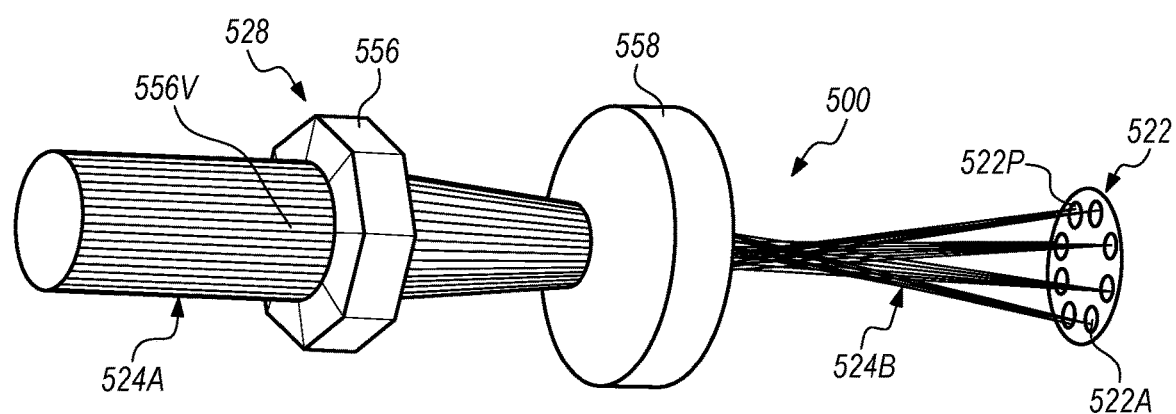
FIG. 5 is a simplified schematic illustration of a portion of another embodiment of the catheter system including another embodiment of the multiplexer.

FIG. 5 is a simplified schematic illustration of a portion of another embodiment of the catheter system 500 including another embodiment of the multiplexer 528. In particular, FIG. 5 illustrates a light guide bundle 522 including a plurality of light guides 522A; and the multiplexer 528 that receives light energy in the form of a source beam 524A, a pulsed source beam 524A in various embodiments, from the light source 124 (illustrated in FIG. 1) and simultaneously and/or sequentially directs the light energy in the form of individual guide beams 524B onto a guide proximal end 522P of at least two of the plurality of the light guides 522A. As such, as shown in FIG. 5, the multiplexer 528 is operatively and/or optically coupled in optical communication to the light guide bundle 522 and/or to the plurality of light guides 522A.

It is appreciated that the light guide bundle 522 can include any suitable number of light guides 522A, which can be positioned and/or oriented relative to one another in any suitable manner to best align the plurality of light guides 522A relative to the multiplexer 528. For example, in the embodiment illustrated in FIG. 5, the light guide bundle 522 again includes eight light guides 522A that are aligned in a generally circular arrangement relative to one another. The light guide bundle 522 and/or the light guides 522A are substantially similar in design and function as described in detail herein above. Accordingly, such components will not be described in detail in relation to the embodiment illustrated in FIG. 5.

In this embodiment, the multiplexer 528 is again somewhat similar to the previous embodiments illustrated and described above. In particular, the multiplexer 528 again includes a multi-faceted prism 556, and coupling optics 558. However, in this embodiment, the multi-faceted prism 556 is an eight-faceted prism. As such, when the source beam 524A is centered on a vertex 556V of the multi-faceted prism 556, the multi-faceted prism 556 can equally split a parallel source beam 524A into eight individual guide beams 524B with different angles around the axis of propagation.

Subsequently, the eight individual guide beams 524B are directed toward the coupling optics 558. As with the previous embodiments, the coupling optics 558 can again include a single focusing lens that is configured to focus the individual guide beams 524B to be arranged in a generally circular pattern relative to one another. With such design, the eight individual guide beams 524B can be effectively directed onto the guide proximal end 522P of each of the eight light guides 522A that are included within the light guide bundle 522.

It is appreciated that with the increased number of facets in the multi-faceted prism 556, the difficulty in fabrication is also generally increased, with the required alignment tolerances being tightened relative to a multi-faceted prism with fewer facets.

Figure 6:
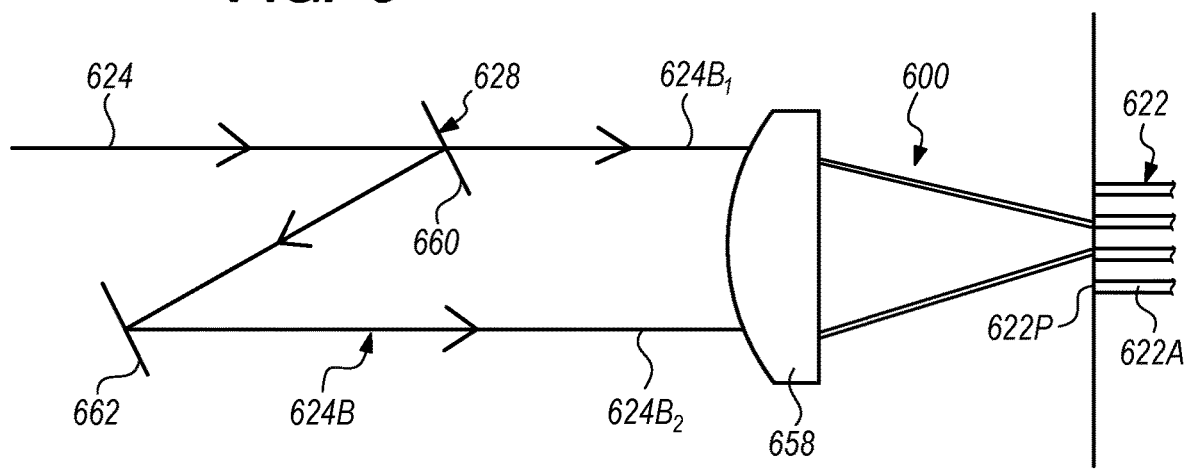
FIG. 6 is a simplified schematic illustration of a portion of yet another embodiment of the catheter system including yet another embodiment of the multiplexer.

FIG. 6 is a simplified schematic illustration of a portion of yet another embodiment of the catheter system 600 including yet another embodiment of the multiplexer 628. In particular, FIG. 6 illustrates a light guide bundle 622 including a plurality of light guides 622A; and the multiplexer 628 that receives light energy in the form of a source beam 624A, a pulsed source beam 624A in various embodiments, from the light source 124 (illustrated in FIG. 1) and simultaneously and/or sequentially directs the light energy in the form of individual guide beams 624B onto a guide proximal end 622P of two of the plurality of the light guides 622A.

It is appreciated that the light guide bundle 622 can include any suitable number of light guides 622A, which can be positioned and/or oriented relative to one another in any suitable manner to best align the plurality of light guides 622A relative to the multiplexer 628. For example, in the embodiment illustrated in FIG. 6, the light guide bundle 622 includes four light guides 622A that are aligned in a linear arrangement relative to one another. The light guide bundle 622 and/or the light guides 622A are substantially similar in design and function as described in detail herein above. Accordingly, such components will not be described in detail in relation to the embodiment illustrated in FIG. 6.

However, as shown in FIG. 6, the multiplexer 628 has a different design than in the previous embodiments. More specifically, as illustrated in this embodiment, the multiplexer 628 includes an optical element provided in the form of and/or functioning as a beamsplitter 660 (thus sometimes also referred to simply as an "optical element"), a redirector 662, and coupling optics 658. Alternatively, the multiplexer 628 can include more components or fewer components than those specifically illustrated in FIG. 6.

Initially, as shown, the source beam 624A is incident on the beamsplitter 660, which can take the form of a partially reflective mirror (e.g., 50% in order to provide guide beams 624B of equal intensity) or other suitable optical element, which splits the source beam 624A into a first guide beam $624B_1$ and a second guide beam $624B_2$. In particular, the first guide beam $624B_1$ is directed through the beamsplitter 660 and toward the coupling optics 658, while the second guide beam $624B_2$ is reflected off of the beamsplitter 660. As shown, the second guide beam $624B_2$ reflects off of the beamsplitter 660 and is redirected toward the redirector 662, which can be a mirror in one embodiment. The second guide beam $624B_2$ then is redirected by and/or reflects off of the redirector 662 and is also directed toward the coupling optics 658.

As with the previous embodiments, as shown, the coupling optics 658 can include a single focusing lens that is configured to focus each of the first guide beam $624B_1$ and the second guide beam $624B_2$ onto the guide proximal end 622P of different light guides 622A in the light guide bundle 622.

It is appreciated that if the two guide beams $624B_1$, $624B_2$ are propagating parallel to one another when introduced into the coupling optics 658, i.e. the focusing lens, then both guide beams $624B_1$, $624B_2$ will focus at the same point, with an angle between them that is determined by the initial separation between them and the focal length of the coupling optics 658. However, if the guide beams $624B_1$, $624B_2$ are incident on the coupling optics 658 with an angle between them (such that the guide beams $624B_1$, $624B_2$ are not precisely parallel to one another), the focal points of each of the guide beams $624B_1$, $624B_2$ will occur in the focal plane with a separation distance between them that is proportional to the initial angular difference. For example, in one non-exclusive alternative embodiment, with 3 mm diameter guide beams $624B_1$, $624B_2$, and with coupling optics 658 having a focal point of 100 mm and a diameter of 25.4 mm, if the initial angle between the guide beams $624B_1$, $624B_2$ is 0.14 degrees, then the separation between the guide beams $624B_1$, $624B_2$ at the focal plane will be 0.251 mm, which can correspond to two separate light guides 622A.

By controlling the initial angle between the guide beams $624B_1$, $624B_2$, the separation between the focal points can be controlled and adjusted to allow multiple light guides 622A to be addressed in any desired manner. More particularly, controlling the angle of the redirector 662 enables the multiplexer 628 to effectively access different light guides 622A with the second guide beam $624B_2$ as desired.

Figure 7:
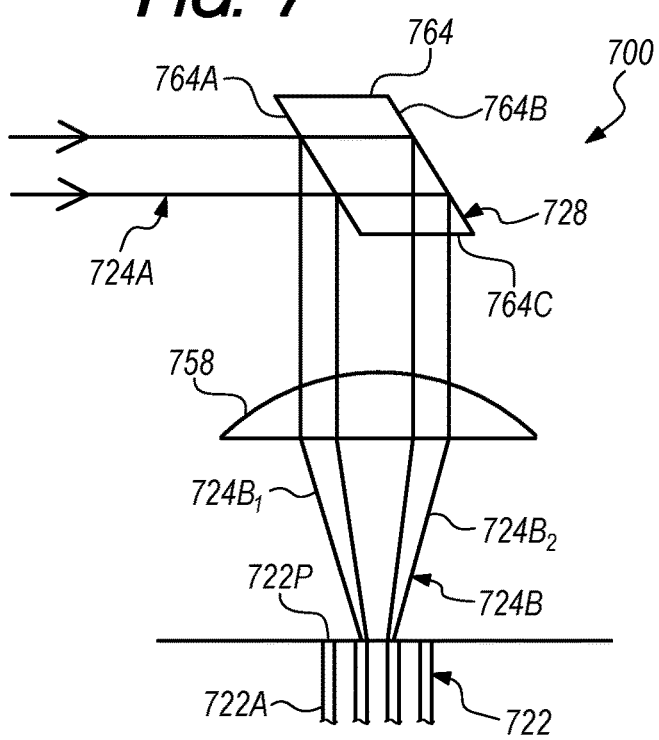
FIG. 7 is a simplified schematic illustration of a portion of another embodiment of the catheter system including another embodiment of the multiplexer.

FIG. 7 is a simplified schematic illustration of a portion of another embodiment of the catheter system 700 including another embodiment of the multiplexer 728. In particular, FIG. 7 illustrates a light guide bundle 722 including a plurality of light guides 722A; and the multiplexer 728 that receives light energy in the form of a source beam 724A, a pulsed source beam 724A in various embodiments, from the light source 124 (illustrated in FIG. 1) and simultaneously and/or sequentially directs the light energy in the form of individual guide beams 724B onto a guide proximal end 722P of two of the plurality of the light guides 722A.

It is appreciated that the light guide bundle 722 can include any suitable number of light guides 722A, which can be positioned and/or oriented relative to one another in any suitable manner to best align the plurality of light guides 722A relative to the multiplexer 728. For example, in the embodiment illustrated in FIG. 7, the light guide bundle 722 includes four light guides 722A that are aligned in a linear arrangement relative to one another. The light guide bundle 722 and/or the light guides 722A are substantially similar in design and function as described in detail herein above. Accordingly, such components will not be described in detail in relation to the embodiment illustrated in FIG. 7.

As illustrated in FIG. 7, the multiplexer 728 is somewhat similar in general design and function to the multiplexer 628 illustrated and described in relation to FIG. 6. However, in this embodiment, the multiplexer 728 includes only a uniquely configured single optical element 764 (instead of the beamsplitter 660 and the redirector 662 illustrated in FIG. 6), in addition to the coupling optics 758. As shown in FIG. 7, the optical element 764 is substantially parallelogram-shaped, and includes an input surface 764A, a rear surface 764B, and an exit surface 764C. In one representative embodiment, the optical element 764 includes a 50% reflective coating on the input surface 764A, a 100% reflective coating on the rear surface 764B, and an anti-reflective coating on the exit surface 764C. With such design, the source beam 724A impinging on the input surface 764A splits the source beam 724A into a first guide beam $724B_1$ that is redirected toward the coupling optics 758; and a second guide beam $724B_2$ that is transmitted through the input surface 764A, impinges on and is redirected by the rear surface 764B toward the exit surface 764C before being directed toward the coupling optics 758.

In this embodiment, the angle between the guide beams $724B_1$, $724B_2$ is controlled by forming the optical element 764 such that it is not a perfect parallelogram, (i.e. an imperfect parallelogram), but rather includes small imperfections or other slight modifications in either the rear surface 764B, the exit surface 764C, or both. In such embodiment, the overall system alignment can be simplified, and space requirements and part count can be reduced at the cost of additional complexities in the optical fabrication.

As noted, after the first guide beam $724B_1$ is reflected off of the input surface 764A, and after the second guide beam $724B_2$ exits the optical element 764 through the exit surface 764C, the guide beams $724B_1$, $724B_2$ are directed toward the coupling optics 758, which can be provided in the form of a single focusing lens, before each of the guide beams $724B_1$, $724B_2$ is focused onto the guide proximal end 722P of a different light guide 722A within the light guide bundle 722. Similar to the previous embodiment, by controlling the angle between the guide beams $724B_1$, $724B_2$ as they are directed toward the coupling optics 758, the separation between the focal points can be controlled and adjusted to allow multiple light guides 722A to be addressed in any desired manner.

FIG. 8 is a simplified schematic illustration of a portion of still another embodiment of the catheter system 800 including still another embodiment of the multiplexer 828. In particular, FIG. 8 illustrates an embodiment of the multiplexer 828 that receives a source beam 824A, a pulsed source beam 824A in various embodiments, from the light source 124 (illustrated in FIG. 1) and splits the source beam 824A to generate two spaced apart, parallel, individual guide beams 824B that can be directed toward and focused substantially simultaneously onto two individual light guides 122A (illustrated in FIG. 1) of the light guide bundle 122 (illustrated in FIG. 1).

As shown in FIG. 8, the design of the multiplexer 828 is different than in the previous embodiments. More specifically, in this embodiment, the multiplexer 828 includes an etalon 866 that is positioned in the beam path of the source beam 824A. An etalon is a common optical element which is fabricated by making a piece of glass with two extremely flat and parallel surfaces. Stated in another manner, such an etalon 866 is configured to include a first etalon surface 866A and a parallel, spaced apart, second etalon surface 866B. As shown, the etalon 866 allows a single collimated source beam 824A to be split into two or more parallel guide beams 824B with a precise distance between the guide beams 824B.

As illustrated in FIG. 8, during use of the multiplexer 828, the source beam 824A is directed at the multiplexer 828, i.e. the etalon 866, at an incident angle, $\Theta_0$. To generate two equal intensity guide beams 824B, a first region 866A$_1$, e.g., a first half, of the first etalon surface 866A can be coated with a fifty percent (50%) reflector at an appropriate wavelength and angle, while a second region 866A$_2$, e.g., a second half, of the first etalon surface 866A can have an anti-reflection (AR) coating. Additionally, the second etalon surface 866B can have a high-reflection coating. In such embodiment, during use of the multiplexer 828, the source beam 824A impinging on the first region 866A$_1$ of the first etalon surface 866A produces a first guide beam 824B, which has been reflected by the first etalon surface 866A, and which has approximately fifty percent of the intensity of the original source beam 824A. The remaining fifty percent of the intensity of the original source beam 824A can then travel through the etalon 866 and be reflected off of the highly-reflective coating on the second etalon surface 866B. The remaining fifty percent of the intensity of the original source beam 824A is then transmitted through the second region 866A$_2$ of the first etalon surface 866A to produce a second guide beam 824B that has approximately fifty percent of the intensity of the original source beam 824A.

Thus, by selectively coating the first etalon surface 866A and the second etalon surface 866B as described, the etalon 866 can be used to generate two parallel guide beams 824B with a separation, s, between them that is set by the incident angle, $\Theta_0$, and a thickness, t, of the etalon 866. In practice, it is appreciated that it is necessary to ensure that the offset or separation, s, between the guide beams 824B is greater than the beam diameter so that the individual guide beams 824B do not overlap spatially. It is further appreciated that if it is desired to generate guide beams 824B of unequal intensity, i.e. with a ratio of beam intensity of other than 1:1, the reflectivity of the first half of the first etalon surface 866A can be altered as desired.

In such embodiments, the separation, s, between the guide beams 824B produced by the multiplexer 828 can be determined as follows:

$$\Theta_i = \sin^{-1}(\sin \Theta_0/n);$$

$$\Delta = 2t \sin \Theta_i;$$

$$s = \Delta \cos \Theta_0;$$

$$s = 2t \sin \Theta_i \cos \Theta_0, \text{ where}$$

n=refractive index of the etalon
t=thickness of the etalon
Δ=[What does Δ represent in these equations?]
$\Theta_0$=incident angle of the source beam onto the etalon
$\Theta_i$=angle of beam within etalon Additionally, or in the alternative, it is appreciated that the multiplexer 828 in the form of the etalon 866 as illustrated in FIG. 8 can also be used in conjunction with a linear scanning mirror (not shown) to address an array of targets, such as an array of light guides 122A, two at a time. If the light guides 122A are arranged in a one-dimensional array, then by orienting the etalon 866 in the correct plane, any pair of light guides 122A with the appropriate offset or separation could be accessed simultaneously by correctly positioning the linear mirror. Alternatively, the etalon 866 can be oriented to allow the linear mirror to address a parallel pair of linear arrays of light guides 122A.

It is further appreciated that the use of an etalon as the multiplexer can be modified from the embodiment shown in FIG. 8 to produce three or more individual guide beams by utilizing a more complicated pattern of coatings on the first etalon surface to allow multiple bounces for the light path within the etalon. More specifically, the etalon can be used to produce three or more individual guide beams by carefully partitioning the coating on the first etalon surface into successively more regions to allow the generation of additional bounces within the etalon. For example, FIG. 9 is a simplified schematic illustration of a portion of another embodiment of the catheter system 900 including another embodiment of the multiplexer 928. In particular, FIG. 9 illustrates an embodiment of the multiplexer 928 that receives a source beam 924A, a pulsed source beam 924A in various embodiments, from the light source 124 (illustrated in FIG. 1) and splits the source beam 924A to generate three spaced apart, parallel, individual guide beams 924B that can be directed toward and focused substantially simultaneously onto three individual light guides 122A (illustrated in FIG. 1) of the light guide bundle 122 (illustrated in FIG. 1).

As shown in the embodiment illustrated in FIG. 9, the multiplexer 928 can again include an etalon 966 including a first etalon surface 966A and a spaced apart, parallel second etalon surface 966B. However, in this embodiment, the first etalon surface 966A can include a first region 966A$_1$ that includes an approximately thirty-three percent (33%) reflective coating, a second region 966A$_2$ that includes a fifty percent (50%) reflective coating, and a third region 966A$_3$ that includes an anti-reflective coating. With such design, the portion of the source beam 924A that reflects off of the first region 966A$_1$ can produce a first guide beam 924B that has approximately thirty-three percent of the intensity of the original source beam 924A. The remaining approximately sixty-seven percent of the intensity of the original source beam 924A can then travel through the etalon 966 and be reflected off of the highly-reflective coating on the second etalon surface 966B. The remaining approximately sixty-seven percent of the intensity of the original source beam 924A then impinges on the second region 966A$_2$ of the first etalon surface 966A such that half travels through the second region 966A$_2$ of the first etalon surface 966A to produce a second guide beam 924B that has approximately thirty-three percent of the intensity of the original source beam 924A, while the remaining approximately thirty-three percent of the intensity of the original source beam 924A is again directed toward the second etalon surface 966B. The remaining approximately thirty-three percent of the intensity of the original source beam 924A will be reflected again off of the second etalon surface 966B before being transmitted through the third region 966A$_3$ of the first etalon surface 966A to produce a third guide beam 924B that has approximately thirty-three percent of the intensity of the original source beam 924A. Thus, the etalon 966 is able to generate three parallel, equal intensity guide beams 924B with a fixed separation distance between them.

FIG. 10 is a simplified schematic illustration of a portion of yet another embodiment of the catheter system 1000 including yet another embodiment of the multiplexer 1028. In particular, FIG. 10 illustrates an embodiment of the multiplexer 1028 that receives a source beam 1024A, a pulsed source beam 1024A in various embodiments, from the light source 124 (illustrated in FIG. 1) and splits the source beam 1024A to generate four spaced apart, parallel, individual guide beams 1024B that can be directed toward and focused substantially simultaneously onto four individual light guides 122A (illustrated in FIG. 1) of the light guide bundle 122 (illustrated in FIG. 1).

As illustrated in FIG. 10, the multiplexer 1028 provides an alternative method for producing multiple guide beams 1024B using etalons. More specifically, in the embodiment illustrated in FIG. 10, the multiplexer 1028 includes a first etalon 1066 having a first, first etalon surface 1066A and a spaced apart second, first etalon surface 1066B; a second etalon 1068 having a first, second etalon surface 1068A and a spaced apart second, second etalon surface 1068B; and a third etalon 1070 having a first, third etalon surface 1070A and a spaced apart second, third etalon surface 1070B, with the three etalons 1066, 1068, 1070 being stacked adjacent to one another with appropriate coatings between them.

Using multiple etalons 1066, 1068, 1070 bounded together that are partly covered with reflective coatings and partly covered with anti-reflection coatings, the source beam 1024A can be split into multiple guide beams 1024B. The intensity of the guide beams 1024B is dependent on the reflectance of the surfaces of each etalon 1066, 1068, 1070, and the intensity of the source beam 1024A. Additionally, the separation of the guide beams 1024B is dependent on the thickness of the etalons 1066, 1068, 1070, the incident angle of the source beam 1024A, and the reflective indexes of the etalons 1066, 1068, 1070.

In one non-exclusive embodiment, when it is desired that each of the guide beams 1024B has a substantially equal intensity, (i) a first region 1066A$_1$ of the first, first etalon surface 1066A can have a twenty-five percent (25%) reflective coating, and a second region 1066A$_2$ of the first, first etalon surface 1066A can have an anti-reflective coating; (ii) a first region 1068A$_1$ of the first, second etalon surface 1068A (or of the second, first etalon surface 1066B) can have an approximately thirty-three percent (33%) reflective coating, and a second region 1068A$_2$ of the first, second etalon surface 1068A (or of the second, first etalon surface 1066B) can have an anti-reflective coating; (iii) a first region 1070A$_1$ of the first, third etalon surface 1070A (or of the second, second etalon surface 1068B) can have a fifty percent (50%) reflective coating, and a second region 1070A$_2$ of first, third etalon surface 1070A (or of the second, second etalon surface 1068B) can have an anti-reflective coating; and (iv) the second, third etalon surface 1070B can have a highly reflective coating.

With such design, the portion of the source beam 1024A that reflects off of the first region 1066A$_1$ of the first, first etalon surface 1066A can produce a first guide beam 1024B that has approximately twenty-five percent of the intensity of the original source beam 1024A. The remaining seventy-five percent of the intensity of the original source beam 1024A can then travel through the first etalon 1066, and the portion of the source beam 1024A that reflects off of the first region 1068A$_1$ of the first, second etalon surface 1068A can then travel through the second region 1066A$_2$ of the first, first etalon surface 1066 to produce a second guide beam 1024B that has approximately twenty-five percent of the intensity of the original source beam 1024A. The remaining fifty percent of the intensity of the original source beam 1024A can then travel through the second etalon 1068, and the portion of the source beam 1024A that reflects off of the first region 1070A$_1$ of the first, third etalon surface 1070A can then travel through the second region 1068A$_2$ of the first, second etalon surface 1068 and through the second region 1066A$_2$ of the first, first etalon surface 1066 to produce a third guide beam 1024B that has approximately twenty-five percent of the intensity of the original source beam 1024A. The remaining twenty-five percent of the intensity of the original source beam 1024A can then travel through the third etalon 1070 and reflect off of the second, third etalon surface 1070B and then travel through the second region 1070A$_2$ of the first, third etalon surface 1070, through the second region 1068A$_2$ of the first, second etalon surface 1068, and through the second region 1066A$_2$ of the first, first etalon surface 1066 to produce a fourth guide beam 1024B that has approximately twenty-five percent of the intensity of the original source beam 1024A. Thus, the etalons 1066, 1068, 1070 used in conjunction with one another are able to generate four parallel, equal intensity guide beams 1024B with a fixed separation distance between them.

In this embodiment, it is important to make sure that the separation distance between the guide beams 1024B is greater than the diameter of the guide beams 1024B.

Additionally, it is appreciated that this concept can be expanded to create any desired number of guide beams, as well as creating uneven beam separations and intensities by adding extra etalons and changing the beam angle, thickness of each etalon and the reflectivity of the surfaces.

Figure 11:
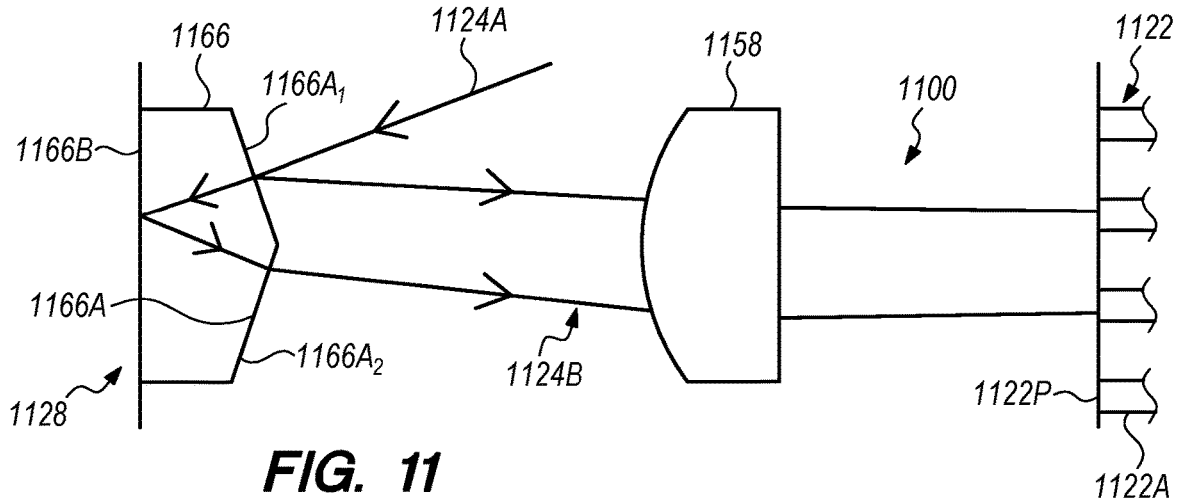
FIG. 11 is a simplified schematic illustration of a portion of another embodiment of the catheter system including another embodiment of the multiplexer.

FIG. 11 is a simplified schematic illustration of a portion of another embodiment of the catheter system 1100 including another embodiment of the multiplexer 1128. In particular, FIG. 11 illustrates a light guide bundle 1122 including a plurality of light guides 1122A; and the multiplexer 1128 that receives light energy in the form of a source beam 1124A, a pulsed source beam 1124A in various embodiments, from the light source 124 (illustrated in FIG. 1) and simultaneously and/or sequentially directs the light energy in the form of individual guide beams 1124B onto a guide proximal end 1122P of two of the plurality of the light guides 1122A.

It is appreciated that the light guide bundle 1122 can include any suitable number of light guides 1122A, which can be positioned and/or oriented relative to one another in any suitable manner to best align the plurality of light guides 1122A relative to the multiplexer 1128. For example, in the embodiment illustrated in FIG. 11, the light guide bundle 1122 includes four light guides 1122A that are aligned in a linear arrangement relative to one another. The light guide bundle 1122 and/or the light guides 1122A are substantially similar in design and function as described in detail herein above. Accordingly, such components will not be described in detail in relation to the embodiment illustrated in FIG. 11.

As illustrated in FIG. 11, the multiplexer 1128 is somewhat similar in general design and function to the multiplexer 828 illustrated and described in relation to FIG. 8. However, in this embodiment, the multiplexer 1128 includes a wedge-shaped etalon 1166 that is positioned in the beam path of the source beam 1124A. Additionally, the etalon 1166 can include a first etalon surface 1066A having a first region $1166A_1$ and a second region $1166A_2$, and a second etalon surface 1066B. In one non-exclusive embodiment, the first region $1166A_1$ of the first etalon surface 1166A can be coated with a fifty percent (50%) reflector at an appropriate wavelength and angle, while the second region $1166A_2$ of the first etalon surface 1166A can have an anti-reflection (AR) coating. Additionally, the second etalon surface 1166B can have a high-reflection coating. In such embodiment, during use of the multiplexer 1128, the source beam 1124A impinging on the first region $1166A_1$ of the first etalon surface 1166A produces a first guide beam 1124B, which has been reflected from the first region $1166A_1$ of the first etalon surface 1166A, and which has approximately fifty percent of the intensity of the original source beam 1124A. The remaining fifty percent of the intensity of the original source beam 1124A can then travel through the etalon 1166 and be reflected off of the highly-reflective coating on the second etalon surface 1166B. The remaining fifty percent of the intensity of the original source beam 1124A is then transmitted through the second region $1166A_2$ of the first etalon surface 1166A to produce a second guide beam 1124B that has approximately fifty percent of the intensity of the original source beam 1124A.

Thus, the multiplexer 1128 is able to split the source beam 1124A into two guide beams 1124B of equal intensity. However, in this embodiment, because the etalon 1166 is wedge-shaped, the two guide beams 1124B emerge with a relative angle between them. Subsequently, the two guide beams 1124B can be focused by coupling optics 1158, such as a single focusing lens in one embodiment, onto two spaced apart light guides 1122A with a distance between them that is set by the relative angle between the two guide beams 1124B before they are focused by the coupling optics 1158.

Figure 12:
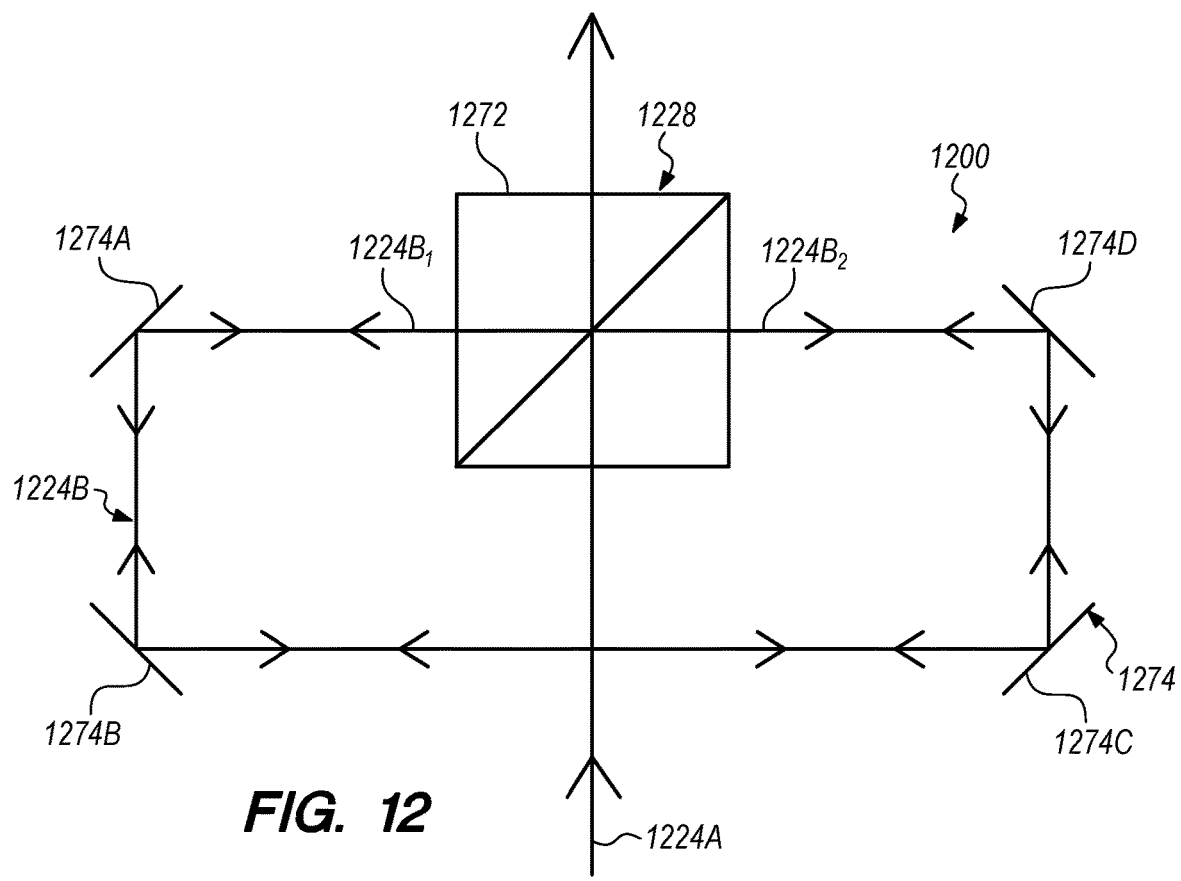
FIG. 12 is a simplified schematic illustration of a portion of still another embodiment of the catheter system including still another embodiment of the multiplexer.

FIG. 12 is a simplified schematic illustration of a portion of still another embodiment of the catheter system 1200 including still another embodiment of the multiplexer 1228. In particular, FIG. 12 illustrates an embodiment of the multiplexer 1228 that receives a source beam 1224A, a pulsed source beam 1224A in various embodiments, from the light source 124 (illustrated in FIG. 1) and splits the source beam 1224A to generate two individual guide beams 1224B that can be directed toward and focused substantially simultaneously onto one or more individual light guides 122A (illustrated in FIG. 1) of the light guide bundle 122 (illustrated in FIG. 1).

As shown in FIG. 12, the design of the multiplexer 1228 is different than in the previous embodiments. More specifically, in this embodiment, the multiplexer 1228 includes an optical element provided in the form of and/or functioning as a polarizing beamsplitter 1272 (thus sometimes also referred to simply as an "optical element"), and a plurality of redirectors 1274. In certain embodiments, the plurality of redirectors 1274 can be provided in the form of ring mirrors. In particular, in this embodiment, the multiplexer 1228 includes four redirectors 1274, i.e. a first redirector 1274A, a second redirector 1274B, a third redirector 1274C and a fourth redirector 1274D, that are positioned about the polarizing beamsplitter 1272. Alternatively, the multiplexer 1228 can have a different design and/or can include a different number of redirectors 1274.

As illustrated, the source beam 1224A is initially directed toward the polarizing beamsplitter 1272 where the source beam 1224A is split into a pair of guide beams 1224B, i.e. a first guide beam $1224B_1$ and a second guide beam $1224B_2$, each with a different polarization. Subsequently, the first guide beam $1224B_1$ with a first polarization is redirected from the polarizing beamsplitter 1272 to the first redirector 1274A, then the second redirector 1274B, then the third redirector 1274C, and then the fourth redirector 1274D, before being directed back toward the polarizing beamsplitter 1272. At the same time, the second guide beam $1224B_2$ with a second polarization is redirected from the polarizing beamsplitter 1272 to the fourth redirector 1274D, then the third redirector 1274C, then the second redirector 1274B, and then the first redirector 1274A, before being directed back toward the polarizing beamsplitter 1272.

In alternative embodiments, by altering the alignment and/or the positioning of the redirectors 1274A-1274D, the guide beams $1224B_1$, $1224B_2$ can be aligned to be one of (i) colinear and overlapping, such that the guide beams $1224B_1$, $1224B_2$ can be recombined and directed toward a single light guide 122A; (ii) parallel and non-overlapping, such that the guide beams $1224B_1$, $1224B_2$ can be directed to two spaced apart, individual light guides 122A; and (iii) propagating at a small angle relative to one another, such that the guide beams $1224B_1$, $1224B_2$ can be focused with coupling optics such as a focusing lens, onto two spaced apart, individual light guides 122A.

Thus, it is appreciated that the polarizing beamsplitter 1272 can be used to generate two guide beams $1224B_1$, $1224B_2$ from the original source beam 1224A to access two spaced apart light guides 122A. Additionally, by proper choice of the input polarization (perhaps set by a half-wave plate), the ratio of intensities between the two guide beams $1224B_1$, $1224B_2$ can be controlled. Also, in certain implementations, due to the polarized nature of the light involved, the guide beams $1224B_1$, $1224B_2$ can be split and recombined without significant power loss.

Figure 13:
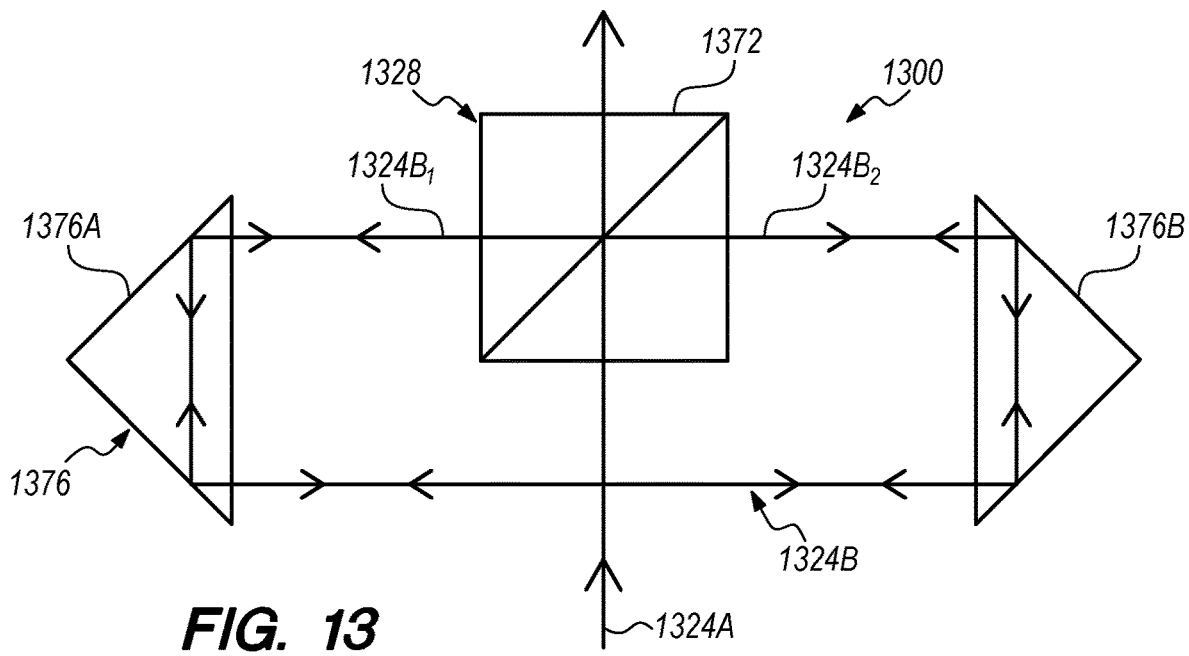
FIG. 13 is a simplified schematic illustration of a portion of another embodiment of the catheter system including another embodiment of the multiplexer.

FIG. 13 is a simplified schematic illustration of a portion of another embodiment of the catheter system 1300 including another embodiment of the multiplexer 1328. In particular, FIG. 13 illustrates an embodiment of the multiplexer 1328 that receives a source beam 1324A, a pulsed source beam 1324A in various embodiments, from the light source 124 (illustrated in FIG. 1) and splits the source beam 1324A to generate two individual guide beams 1324B that can be directed toward and focused substantially simultaneously onto one or more individual light guides 122A (illustrated in FIG. 1) of the light guide bundle 122 (illustrated in FIG. 1).

As shown in FIG. 13, the design of the multiplexer 1328 is somewhat similar to the embodiment illustrated and described in relation to FIG. 12. More specifically, in this embodiment, the multiplexer 1328 includes an optical element provided in the form of and/or functioning as a polarizing beamsplitter 1372 (thus sometimes also referred to simply as an "optical element"), and a plurality of redirectors 1376. However, in this embodiment, the multiplexer 1328 includes two redirectors 1376, i.e. a first redirector 1376A, and a second redirector 1376B, in the form of corner cubes that are positioned about the polarizing beamsplitter 1272.

As illustrated, the source beam 1324A is initially directed toward the polarizing beamsplitter 1372 where the source beam 1324A is split into a pair of guide beams 1324B, i.e. a first guide beam 1324B$_1$ and a second guide beam 1324B$_2$, each with a different polarization. Subsequently, the first guide beam 1324B$_1$ with a first polarization is redirected from the polarizing beamsplitter 1372 to the first redirector 1376A, and then the second redirector 1374B, before being directed back toward the polarizing beamsplitter 1372. At the same time, the second guide beam 1324B$_2$ with a second polarization is redirected from the polarizing beamsplitter 1372 to the second redirector 1376B, and then the first redirector 1376A, before being directed back toward the polarizing beamsplitter 1372.

As with the embodiments illustrated in FIG. 12, by altering the alignment and/or the positioning of the redirectors 1376A, 1376B, the guide beams 1324B$_1$, 1324B$_2$ can be aligned to be one of (i) colinear and overlapping, such that the guide beams 1324B$_1$, 1324B$_2$ can be recombined and directed toward a single light guide 122A; (ii) parallel and non-overlapping, such that the guide beams 1324B$_1$, 1324B$_2$ can be directed to two spaced apart, individual light guides 122A; and (iii) propagating at a small angle relative to one another, such that the guide beams 1324B$_1$, 1324B$_2$ can be focused with coupling optics such as a focusing lens, onto two spaced apart, individual light guides 122A.

With such design, where pairs of mirrors have been replaced by corner cubes, the overall fabrication and alignment of the multiplexer 1328 can be simplified, while still allowing for the three alternative scenarios noted above. Additionally, it is further appreciated that the redirectors 1376A, 1376B, i.e. the corner cubes, can be rotated by approximately ninety degrees so that the guide beam loop is in a different plane that the source beam 1324A. This may improve packaging or may improve the performance of the reflective coatings on the redirectors 1376A, 13376B.

Figure 14:
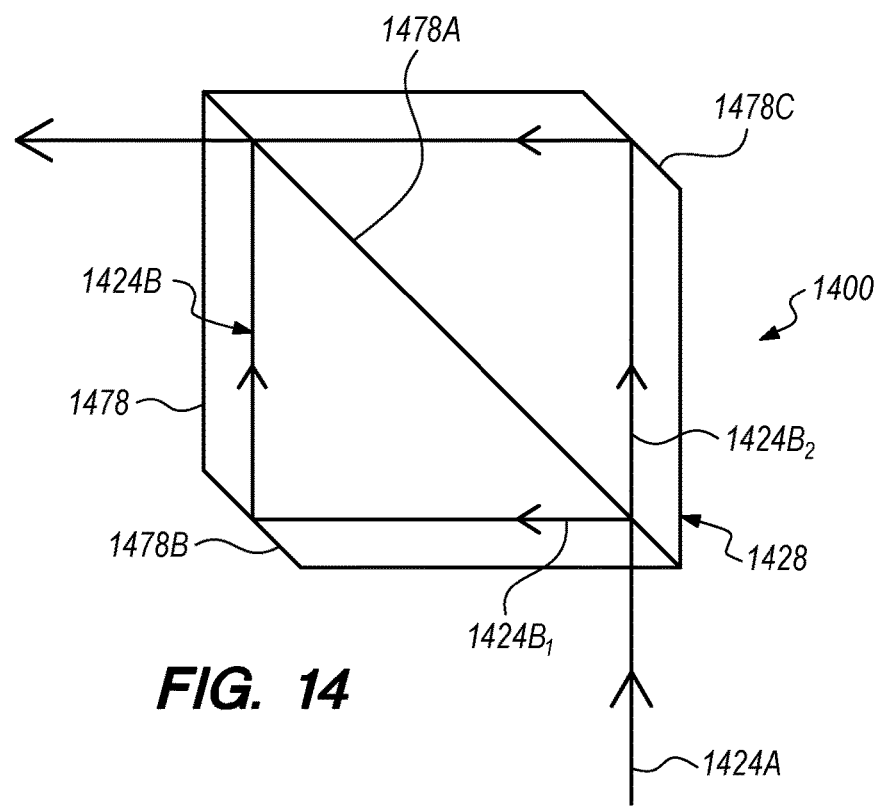
FIG. 14 is a simplified schematic illustration of a portion of yet another embodiment of the catheter system including yet another embodiment of the multiplexer.

FIG. 14 is a simplified schematic illustration of a portion of yet another embodiment of the catheter system 1400 including yet another embodiment of the multiplexer 1428. In particular, FIG. 14 illustrates an embodiment of the multiplexer 1428 that receives a source beam 1424A, a pulsed source beam 1424A in various embodiments, from the light source 124 (illustrated in FIG. 1) and splits the source beam 1424A to generate two individual guide beams 1424B that can be directed toward and focused substantially simultaneously onto one or more individual light guides 122A (illustrated in FIG. 1) of the light guide bundle 122 (illustrated in FIG. 1).

As shown in FIG. 14, the design of the multiplexer 1428 is somewhat similar to the embodiments illustrated and described in relation to FIGS. 12 and 13. However, in this embodiment, the polarizing beamsplitter and the redirectors have been replaced by a single optical element 1478, in the form of a polarizing beamsplitter, reflective cube.

As illustrated, the source beam 1424A is initially directed toward the polarizing beamsplitter portion 1478A of the optical element 1478 where the source beam 1424A is split into a pair of guide beams 1424B, i.e. a first guide beam 1424B$_1$ and a second guide beam 1424B$_2$, each with a different polarization. Subsequently, the first guide beam 1424B$_1$ with a first polarization is redirected from the polarizing beamsplitter portion 1478A of the optical element 1478 to a first reflective surface 1478B of the optical element 1478, before being directed back toward the polarizing beamsplitter portion 1478A of the optical element 1478. At the same time, the second guide beam 1424B$_2$ with a second polarization is redirected from (or transmitted through) the polarizing beamsplitter portion 1478A of the optical element 1478 to a second reflective surface 1478C of the optical element 1478, before being directed back toward the polarizing beamsplitter portion 1478A of the optical element 1478.

As with the embodiments illustrated in FIGS. 12 and 13, by altering the alignment and/or the positioning of the reflective surfaces 1478B, 1478C of the optical element 1478, the guide beams 1424B$_1$, 1424B$_2$ can be aligned to be one of (i) colinear and overlapping, such that the guide beams 1424B$_1$, 1424B$_2$ can be recombined and directed toward a single light guide 122A; (ii) parallel and non-overlapping, such that the guide beams 1424B$_1$, 1424B$_2$ can be directed to two spaced apart, individual light guides 122A; and (iii) propagating at a small angle relative to one another, such that the guide beams 1424B$_1$, 1424B$_2$ can be focused with coupling optics such as a focusing lens, onto two spaced apart, individual light guides 122A.

It is appreciated that with this embodiment, the overall alignment of the multiplexer 1428 can be simplified since all of the tolerances and relative beam positions on exit are controlled by the fabrication of the optical element 1478.

It is further appreciated that an additional requirement for the utility of catheter systems is the need to selectively and specifically access one or more of multiple light guides to allow for the controlled application of therapeutic optical radiation to the correct area(s) at the treatment site inside the catheter system. In principal, this can be done by either moving the guide beam(s) in order to specifically access the desired light guide(s) or moving the light guides themselves. The embodiments illustrated at least in FIGS. 15A-17B provide alternative methods for accomplishing such a task.

Figure 15A:
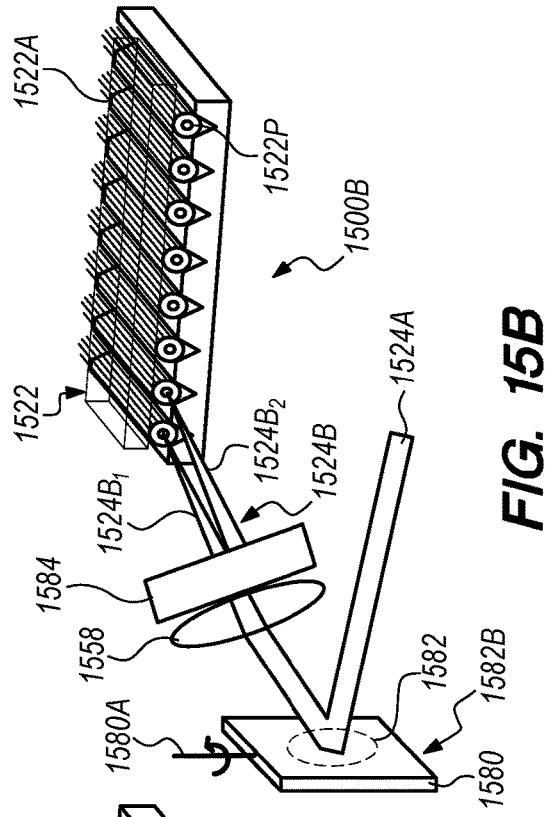
FIG. 15A is a simplified schematic illustration of a portion of another embodiment of the catheter system including another embodiment of the multiplexer.

FIG. 15A is a simplified schematic illustration of a portion of another embodiment of the catheter system 1500A including another embodiment of the multiplexer 1528A. In particular, FIG. 15A illustrates a light guide bundle 1522 including a plurality of light guides 1522A; and the multiplexer 1528A that receives light energy in the form of a source beam 1524A, a pulsed source beam 1524A in various embodiments, from the light source 124 (illustrated in FIG. 1) and directs the light energy in the form of individual guide beams 1524B onto a guide proximal end 1522P of one or more of the plurality of the light guides 1522A. In some such embodiments, the multiplexer 1528A is configured to sequentially direct the light energy in the form of individual guide beams 1524B onto the guide proximal end 1522P of one or more of the plurality of the light guides 1522A.

It is appreciated that the light guide bundle 1522 can include any suitable number of light guides 1522A, which can be positioned and/or oriented relative to one another in any suitable manner to best align the plurality of light guides 1522A relative to the multiplexer 1528A. For example, in the embodiment illustrated in FIG. 15A, the light guide bundle 1522 includes eight light guides 1522A that are aligned in a linear arrangement relative to one another. The light guide bundle 1522 and/or the light guides 1522A are substantially similar in design and function as described in detail herein above. Accordingly, such components will not be described in detail in relation to the embodiment illustrated in FIG. 15A.

In the embodiment illustrated in FIG. 15A, the multiplexer 1528A is specifically configured to selectively and sequentially couple the guide beam(s) 1524B to one or more of the light guides 1522A. More specifically, as shown, the multiplexer 1528A includes a redirector 1580 and coupling optics 1558. In one embodiment, as illustrated, the redirector 1580 is provided in the form of a galvanometer, such as a galvanometer mirror scanner, that includes a mirror (or other reflective surface) that is rotated about an axis 1580A using a mover 1582. The mover 1582 is utilized to rotate the mirror of the redirector 1580 in order to steer the guide beam 1524B into the coupling optics 1558 at a desired incident angle, so that the guide beam 1524B can be selectively focused by the coupling optics 1558 onto any of the light guides 1522A within the light guide bundle 1522. In particular, as the redirector 1580 is rotated, the redirector 1580 steers the guide beam 1524B into the coupling optics 1558 at different angles. This results in scanning of the guide beam 1524B in a linear manner, translating the focal point into different light guides 1522A mounted within a fixed light guide bundle 1522. Thus, by changing the angle of the redirector 1580, the guide beam 1524B can be selectively steered onto the guide proximal end 1522P of any of the light guides 1522A in the light guide bundle 1522.

In comparison to a comparable system that instead moves the light guide bundle 1522 relative to a fixed guide beam 1524B, the advantage of this method is the speed and extreme precision and repeatability of the redirector 1580 compared to a stage that moves the light guide bundle 1522.

Figure 15B:
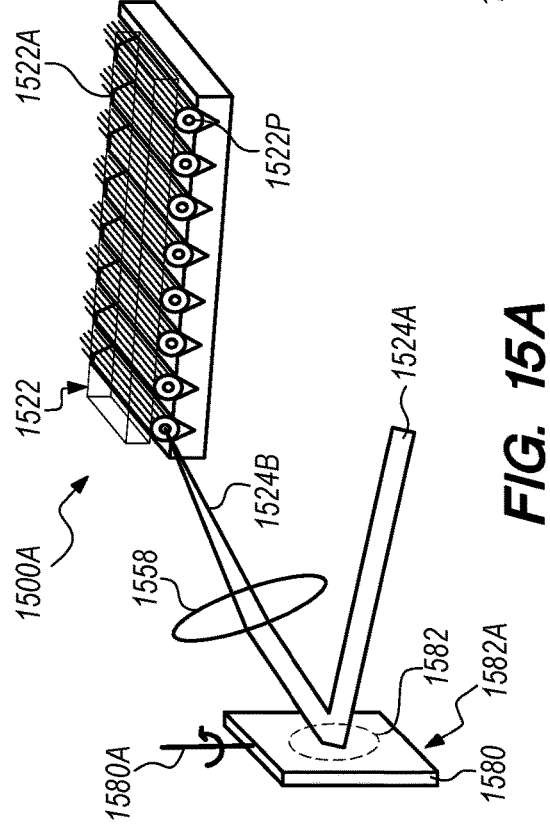
FIG. 15B is a simplified schematic illustration of a portion of still another embodiment of the catheter system including still another embodiment of the multiplexer.

FIG. 15B is a simplified schematic illustration of a portion of still another embodiment of the catheter system 1500B including still another embodiment of the multiplexer 1528B. As shown, the catheter system 1500B and the multiplexer 1528B are substantially similar to the catheter system 1500A and the multiplexer 1528A illustrated and described in relation to FIG. 15A. For example, the catheter system 1500B again includes the light guide bundle 1522 including the plurality of light guides 1522A; and the multiplexer 1528B that receives light energy in the form of a source beam 1524A, a pulsed source beam 1524A in various embodiments, from the light source 124 (illustrated in FIG. 1) and directs the light energy in the form of individual guide beams 1524B onto a guide proximal end 1522P of one or more of the plurality of the light guides 1522A. Additionally, the multiplexer 1528B again includes the redirector 1580 that is moved about the axis 1580A by the mover 1582 to direct the guide beam(s) 1524B at a desired incident angle through the coupling optics 1558 in order to scan the guide beam(s) 1524B in a linear manner relative to the light guide bundle 1522.

However, in this embodiment, the multiplexer 1528B further includes a beam multiplier 1584 that can be used to split the guide beam 1524B and/or the source beam 1524A into a plurality of guide beams 1524B, e.g., a first guide beam 1524B$_1$ and a second guide beam 1524B$_2$ as shown in FIG. 15B. The beam multiplier 1584 can have any suitable design. For example, in certain embodiments, the beam multiplier 1584 can have a design such as illustrated and described herein above for the multiplexer in any of FIGS. 2-14.

With such design, the guide beams 1524B$_1$, 1524B$_2$ can be coupled onto multiple light guides 1522A simultaneously in any desired manner.

Figure 16A:
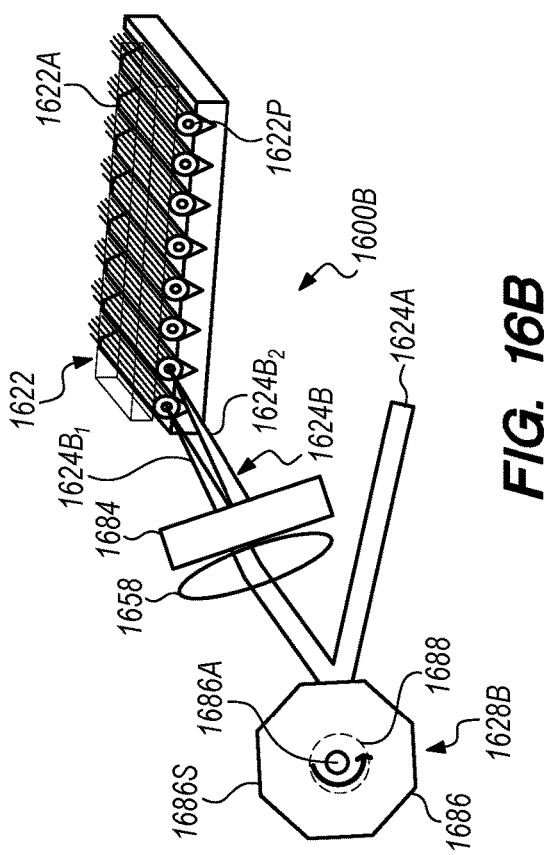
FIG. 16A is a simplified schematic illustration of a portion of another embodiment of the catheter system including another embodiment of the multiplexer.

FIG. 16A is a simplified schematic illustration of a portion of another embodiment of the catheter system 1600A including another embodiment of the multiplexer 1628A. In particular, FIG. 16A illustrates a light guide bundle 1622 including a plurality of light guides 1622A; and the multiplexer 1628A that receives light energy in the form of a source beam 1624A, a pulsed source beam 1624A in various embodiments, from the light source 124 (illustrated in FIG. 1) and directs the light energy in the form of individual guide beams 1624B onto a guide proximal end 1622P of one or more of the plurality of the light guides 1622A. In some such embodiments, the multiplexer 1628A is configured to sequentially direct the light energy in the form of individual guide beams 1624B onto the guide proximal end 1622P of one or more of the plurality of the light guides 1622A.

It is appreciated that the light guide bundle 1622 can include any suitable number of light guides 1622A, which can be positioned and/or oriented relative to one another in any suitable manner to best align the plurality of light guides 1622A relative to the multiplexer 1628A. For example, in the embodiment illustrated in FIG. 16A, the light guide bundle 1622 includes eight light guides 1622A that are aligned in a linear arrangement relative to one another. The light guide bundle 1622 and/or the light guides 1622A are substantially similar in design and function as described in detail herein above. Accordingly, such components will not be described in detail in relation to the embodiment illustrated in FIG. 16A.

In the embodiment illustrated in FIG. 16A, the multiplexer 1628A is again specifically configured to selectively and sequentially couple the guide beam(s) 1624B to one or more of the light guides 1622A. More specifically, as shown, the multiplexer 1628A includes a redirector 1686 and coupling optics 1658. However, in this embodiment, the redirector 1686 has a different design than in the preceding embodiments. In particular, as shown, the redirector 1686 is provided in the form of a rotating multi-sided mirror that is rotated about an axis 1686A with a mover 1688. In some embodiments, the redirector 1686 can be an eight-sided rotating mirror. Alternatively, the redirector 1686 can have a different number of sides.

The mover 1688 is utilized to rotate the multi-sided mirror of the redirector 1686 so that the source beam 1624A reflects off of a side 1686S of the redirector 1686 to provide a guide beam 1624B that is steered into the coupling optics 1658 at a desired incident angle, so that the guide beam 1624B can be selectively focused by the coupling optics 1658 onto any of the light guides 1622A within the light guide bundle 1622. As the redirector 1686 is rotated continuously, the sides 1686S of the redirector 1686 steer the guide beam 1624B into the coupling optics 1658 at different angles. This results in scanning of the guide beam 1624B in a linear manner, translating the focal point into different light guides 1622A mounted within a fixed light guide bundle 1622. Thus, by changing the angle of the redirector 1686, the guide beam 1624B can be selectively steered onto the guide proximal end 1622P of any of the light guides 1622A in the light guide bundle 1622.

It is appreciated that with the design of the redirector 1686 illustrated in FIG. 16A, the redirector 1686 automatically resets itself as each of the sides 1686S of the redirector 1686 is moved into the beam path of the source beam 1624A. This allows the redirector 1686 to move at a constant rate (in contrast to repeated accelerations as required of the redirector 1580 described above). Additionally, a desired rate can be chosen in conjunction with the pulse repetition rate of the light source 124 such that the light source 124 only fires when the redirector 1686 is aligned to place the light energy from the guide beam 1624B onto the guide proximal end 1622P of the appropriate light guide 1622A. It is further appreciated that the speed of rotation of the redirector 1686 should be selected to be in synch with the distance between the light guides 1622A within the light guide bundle 1622.

Figure 16B:
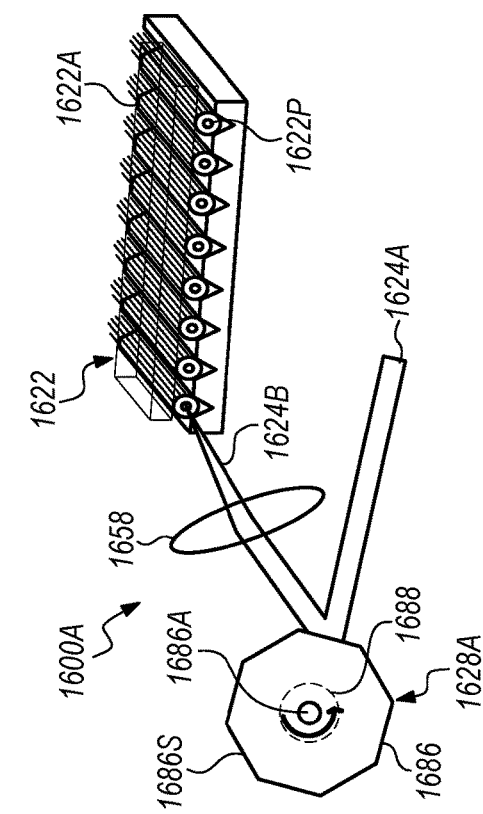
FIG. 16B is a simplified schematic illustration of a portion of yet another embodiment of the catheter system including yet another embodiment of the multiplexer.

FIG. 16B is a simplified schematic illustration of a portion of yet another embodiment of the catheter system 1600B including yet another embodiment of the multiplexer 1628B. As shown, the catheter system 1600B and the multiplexer 1628B are substantially similar to the catheter system 1600A and the multiplexer 1628A illustrated and described in relation to FIG. 16A. For example, the catheter system 1600B again includes the light guide bundle 1622 including the plurality of light guides 1622A; and the multiplexer 1628B that receives light energy in the form of a source beam 1624A, a pulsed source beam 1624A in various embodiments, from the light source 124 (illustrated in FIG. 1) and directs the light energy in the form of individual guide beams 1624B onto a guide proximal end 1622P of one or more of the plurality of the light guides 1622A. Additionally, the multiplexer 1628B again includes the redirector 1686 that is moved about the axis 1686A by the mover 1688 so that the sides 1686S of the redirector 1686 direct the guide beam(s) 1624B at a desired incident angle through the coupling optics 1658 in order to scan the guide beam(s) 1624B in a linear manner relative to the light guide bundle 1622.

However, in this embodiment, the multiplexer 1628B further includes a beam multiplier 1684 that can be used to split the guide beam 1624B and/or the source beam 1624A into a plurality of guide beams 1624B, e.g., a first guide beam $1624B_1$ and a second guide beam $1624B_2$ such as shown in FIG. 16B. The beam multiplier 1684 can have any suitable design. For example, in certain embodiments, the beam multiplier 1684 can have a design such as illustrated and described herein above for the multiplexer in any of FIGS. 2-14.

With such design, the guide beams $1624B_1$, $1624B_2$ can be coupled onto multiple light guides 1622A simultaneously in any desired manner.

Figure 17A:
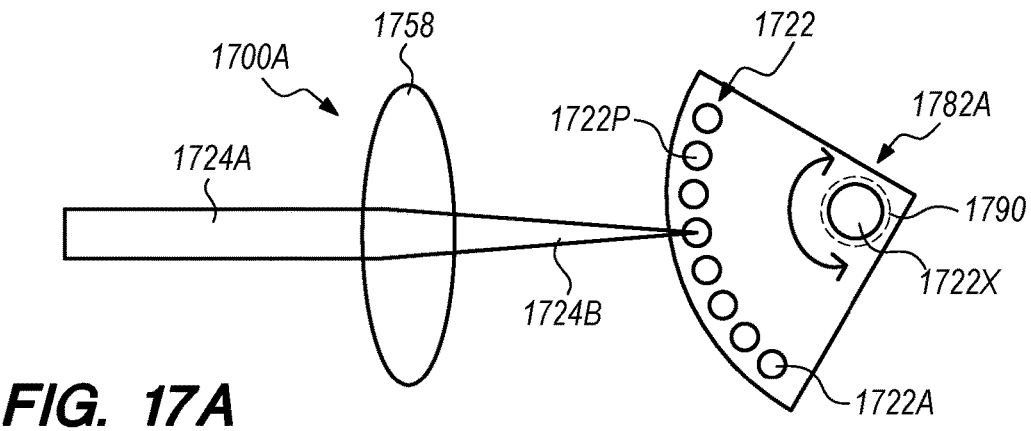
FIG. 17A is a simplified schematic illustration of a portion of another embodiment of the catheter system including another embodiment of the multiplexer.

FIG. 17A is a simplified schematic illustration of a portion of another embodiment of the catheter system 1700A including another embodiment of the multiplexer 1728A. In particular, FIG. 17A illustrates a light guide bundle 1722 including a plurality of light guides 1722A; and the multiplexer 1728A that receives light energy in the form of a source beam 1724A, a pulsed source beam 1724A in various embodiments, from the light source 124 (illustrated in FIG. 1) and directs the light energy in the form of individual guide beams 1724B onto a guide proximal end 1722P of one or more of the plurality of the light guides 1722A. In some such embodiments, the multiplexer 1728A is configured to sequentially direct the light energy in the form of individual guide beams 1724B onto the guide proximal end 1722P of one or more of the plurality of the light guides 1722A.

It is appreciated that the light guide bundle 1722 can include any suitable number of light guides 1722A, which can be positioned and/or oriented relative to one another in any suitable manner to best align the plurality of light guides 1722A relative to the multiplexer 1728A. For example, in the embodiment illustrated in FIG. 17A, the light guide bundle 1722 includes eight light guides 1722A that are aligned in an arc-shaped arrangement relative to one another. The light guide bundle 1722 and/or the light guides 1722A are substantially similar in design and function as described in detail herein above. Accordingly, such components will not be described in detail in relation to the embodiment illustrated in FIG. 17A.

In the embodiment illustrated in FIG. 17A, the multiplexer 1728A includes coupling optics 1758 that focus the guide beam 1724B toward the light guides 1722A, while the light guide bundle 1722 is rotated about a bundle axis 1722X with a bundle mover 1790. During use of the catheter system 1700A, the bundle mover 1790 is configured to rotate the light guide bundle 1722 about the bundle axis 1722X so that the desired light guide 1722A is positioned in the beam path of the guide beam 1724B as the coupling optics 1758 focus the guide beam 1724B toward the light guide bundle 1722.

It is appreciated that in such embodiment, the light guide bundle 1722 needs to oscillate back and forth to select the desired light guide 1722A, since only rotating in one direction would 'wind up' the light guides and eventually break them. However, it is further appreciated that such advantage does provide advantages in compactness and speed of switching between the light guides 1722A is comparison to a linear array of light guides that is mounted on a moving stage.

Figure 17B:
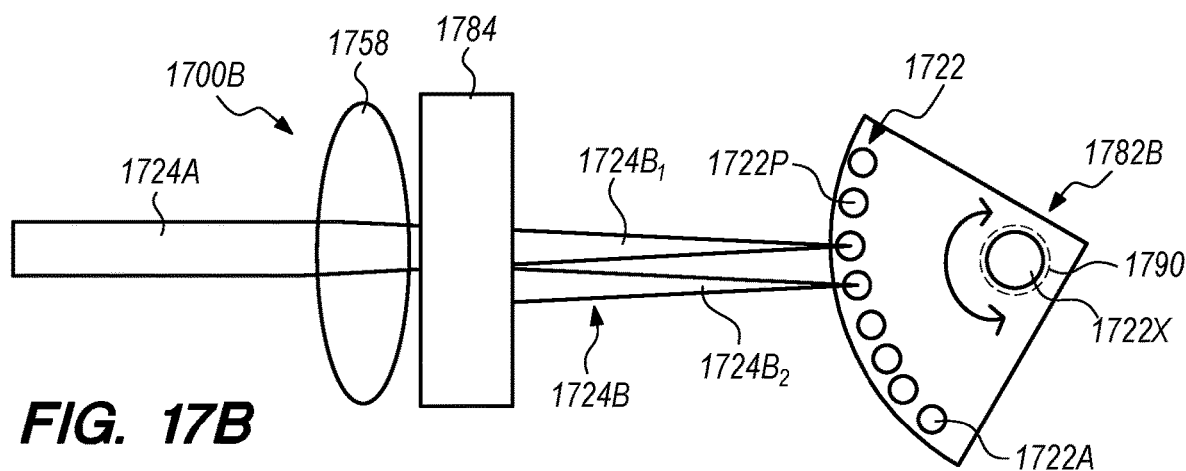
FIG. 17B is a simplified schematic illustration of a portion of still another embodiment of the catheter system including still another embodiment of the multiplexer.

FIG. 17B is a simplified schematic illustration of a portion of still another embodiment of the catheter system 1700B including still yet another embodiment of the multiplexer 1728B. As shown, the catheter system 1700B and the multiplexer 1728B are substantially similar to the catheter system 1700A and the multiplexer 1728A illustrated and described in relation to FIG. 17A. For example, the catheter system 1700B again includes the light guide bundle 1722 including the plurality of light guides 1722A; and the multiplexer 1728B that receives light energy in the form of a source beam 1724A, a pulsed source beam 1724A in various embodiments, from the light source 124 (illustrated in FIG. 1) and directs the light energy in the form of individual guide beams 1724B onto a guide proximal end 1722P of one or more of the plurality of the light guides 1722A. Additionally, the multiplexer 1728B again includes the coupling optics 1758 that focus the guide beam(s) onto the desired light guides 1722A as the light guide bundle 1722 is rotated about the bundle axis 1722X by the bundle mover 1790.

However, in this embodiment, the multiplexer 1728B further includes a beam multiplier 1784 that can be used to split the guide beam 1724B and/or the source beam 1724A into a plurality of guide beams 1724B, e.g., a first guide beam $1724B_1$ and a second guide beam $1724B_2$ such as is shown in FIG. 17B. The beam multiplier 1784 can have any suitable design. For example, in certain embodiments, the beam multiplier 1784 can have a design such as illustrated and described herein above for the multiplexer in any of FIGS. 2-14.

With such design, the guide beams $1724B_1$, $1724B_2$ can be coupled onto multiple light guides 1722A simultaneously in any desired manner.

Figure 18A:
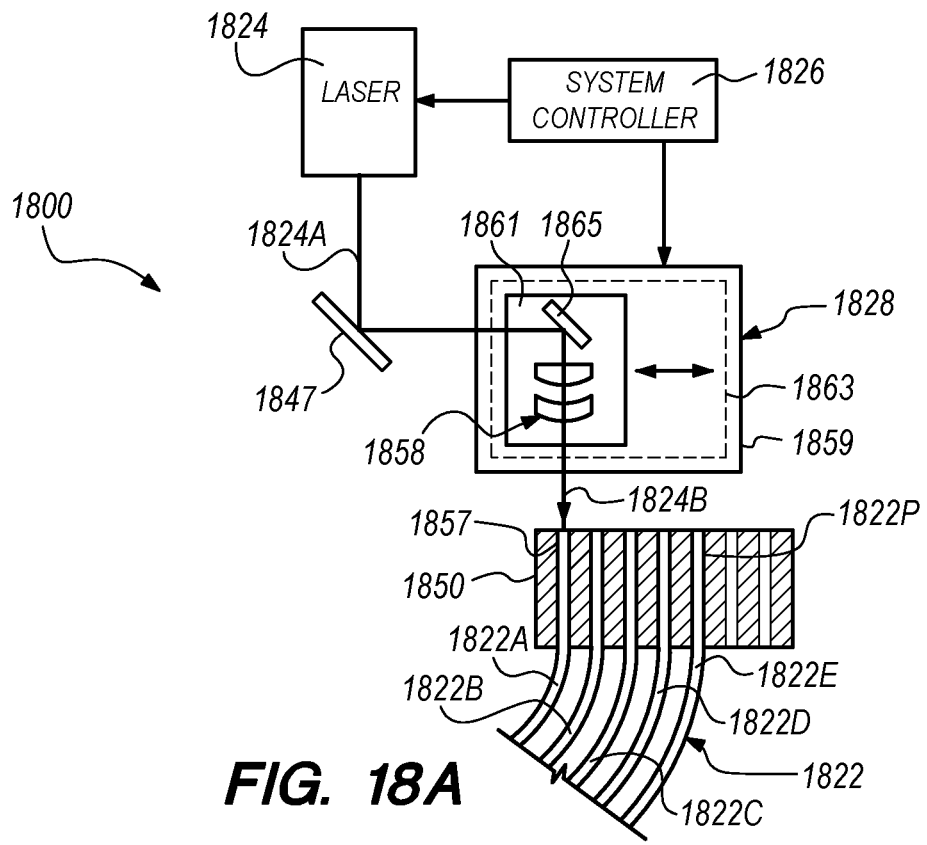
FIG. 18A is a simplified schematic top view illustration of a portion of another embodiment of the catheter system including another embodiment of the multiplexer.

FIG. 18A is a simplified schematic top view illustration of a portion of another embodiment of the catheter system 1800 including another embodiment of the multiplexer 1828. More particularly, FIG. 18A illustrates a light guide bundle 1822 including a plurality of light guides, such as a first light guide 1822A, a second light guide 1822B, a third light guide 1822C, a fourth light guide 1822D and a fifth light guide 1822E; a light source 1824; a system controller 1826; and another embodiment of the multiplexer 1828 that receives light energy in the form of a source beam 1824A, a pulsed source beam 1824A in various embodiments, from the light source 1824 and selectively and/or alternatively directs the light energy in the form of individual guide beams 1824B to each of the light guides 1822A-1822E. The light guide bundle 1822, the light guides 1822A-1822E, the light source 1824 and the system controller 1826 are substantially similar in design and function as described in detail herein above. Accordingly, such components will not be described in detail in relation to the embodiment illustrated in FIG. 18A. It is further appreciated that certain components of the system console 123 illustrated and described above in relation to FIG. 1, such as the power source 125 and the GUI 127, are not illustrated in FIG. 18A for purposes of simplicity and ease of illustration, but would typically be included in many embodiments.

It is appreciated that the light guide bundle 1822 can include any suitable number of light guides, which can be positioned and/or oriented relative to one another in any suitable manner to best align the plurality of light guides relative to the multiplexer 1828. For example, in the embodiment illustrated in FIG. 18A, the light guide bundle 1822 includes the first light guide 1822A, the second light guide 1822B, the third light guide 1822C, the fourth light guide 1822D and the fifth light guide 1822E that are aligned in a linear arrangement relative to one another. Alternatively, the light guide bundle 1822 can include greater than five or less than five light guides.

The multiplexer 1828 is again configured to receive light energy in the form of the source beam 1824A from the light source 1824 and selectively and/or alternatively direct the light energy in the form of individual guide beams 1824B to each of the light guides 1822A-1822E. As such, as shown in FIG. 18A, the multiplexer 1828 is operatively and/or optically coupled in optical communication to the light guide bundle 1822 and/or to the plurality of light guides 1822A-1822E.

As illustrated, a guide proximal end 1822P of each of the plurality of light guides 1822A-1822E is retained within a guide coupling housing 1850, i.e. within guide coupling slots 1857 that are formed into the guide coupling housing 1850. In various embodiments, the guide coupling housing 1850 is configured to be selectively coupled to the system console 123 (illustrated in FIG. 1) so that the guide coupling slots 1857, and thus the light guides 1822A-1822E, are maintained in a desired fixed position relative to the multiplexer 1828 during use of the catheter system 1800. In some embodiments, the guide coupling slots 1857 are provided in the form of V-grooves, such as in a V-groove ferrule block commonly used in multichannel fiber optics communication systems. Alternatively, the guide coupling slots 1857 can have another suitable design.

It is appreciated that the guide coupling housing 1850 can have any suitable number of guide coupling slots 1857, which can be positioned and/or oriented relative to one another in any suitable manner to best align the guide coupling slots 1857 and thus the light guides 1822A-1822E relative to the multiplexer 1828. In the embodiment illustrated in FIG. 18A, the guide coupling housing 1850 includes seven guide coupling slots 1857 that are spaced apart in a linear arrangement relative to one another, with precise interval spacing between adjacent guide coupling slots 1857. Thus, in such embodiment, the guide coupling housing 1850 is capable of retaining the guide proximal end 1822P of up to seven light guides (although only five light guides 1822A-1822E are specifically shown in FIG. 18A). Alternatively, the guide coupling housing 1850 can have greater than seven or less than seven guide coupling slots 1857, and/or the guide coupling slots 1857 can be arranged in a different manner relative to one another.

The design of the multiplexer 1828 can be varied depending on the requirements of the catheter system 1800, the relative positioning of the light guides 1822A-1822E, and/or to suit the desires of the user or operator of the catheter system 1800. In the embodiment illustrated in FIG. 18A, the multiplexer 1828 includes one or more of a multiplexer base 1859, a multiplexer stage 1861, a stage mover 1863 (illustrated in phantom), a redirector 1865, and coupling optics 1858. Alternatively, the multiplexer 1828 can include more components or fewer components than those specifically illustrated in FIG. 18A.

During use of the catheter system 1800, the multiplexer base 1859 is fixed in position relative to the light source 1824 and the light guides 1822A-1822E. Additionally, in this embodiment, the multiplexer stage 1861 is movably supported on the multiplexer base 1859. More particularly, the stage mover 1863 is configured to move the multiplexer stage 1861 relative to the multiplexer base 1859. As shown in FIG. 18A, the redirector 1865 and the coupling optics 1858 are mounted on and/or retained by the multiplexer stage 1861. Thus, movement of the multiplexer stage 1861 relative to the multiplexer base 1859 results in corresponding movement of the redirector 1865 and the coupling optics 1858 relative to the fixed multiplexer base 1859. With the light guides 1822A-1822E being fixed in position relative to the multiplexer base 1859, movement of the multiplexer stage 1861 results in corresponding movement of the redirector 1865 and the coupling optics 1858 relative to the light guides 1822A-1822E.

In various embodiments, the multiplexer 1828 is configured to precisely align the coupling optics 1858 with each of the light guides 1822A-1822E such that the source beam 1824A generated by the light source 1824 can be precisely directed and focused by the multiplexer 1828 as a corresponding guide beam 1824B to each of the light guides 1822A-1822E. In its simplest form, as shown in FIG. 18A, the multiplexer 1828 uses a precision mechanism such as the stage mover 1863 to translate the coupling optics 1858 along a linear path. This approach requires a single degree of freedom. In certain embodiments, the linear translation mechanism in the form of the stage mover 1863, and/or the multiplexer stage 1861 can be equipped with mechanical stops so that the coupling optics 1858 can be precisely aligned with the position of each of the light guides 1822A-1822E. Alternatively, the stage mover 1863 can be electronically controlled to line the beam path of the guide beam 1824B sequentially with each individual light guide 1822A-1822E that is retained, in part, within the guide coupling housing 1850.

The multiplexer stage 1862 is configured to carry the necessary optics, such as the redirector 1865 and the coupling optics 1858, to direct and focus the light energy generated by the light source 1824 to each light guide 1822A-1822E for optimal coupling. With such design, the low divergence of the guide beam 1824A over the short distance of motion of the translated multiplexer stage 1861 has minimum impact on coupling efficiency to the light guide 1822A-1822E.

During operation, the stage mover 1863 drives the multiplexer stage 1861 to align the beam path of the guide beam 1824B with a selected light guide 1822A-1822E and then the system controller 1826 fires the light source 1824 in pulsed or semi-CW mode. The stage mover 1863 then steps the multiplexer stage 1861 to the next stop, i.e. to the next light guide 1822A-1822E, and the system controller 1826 again fires the light source 1824. This process is repeated as desired so that light energy in the form of the guide beams 1824B is directed to each of the light guides 1822A-1822E in a desired pattern. It is appreciated that the stage mover 1863 can move the multiplexer stage 1861 so that it is aligned with any of the light guides 1822A-1822E, then the system controller 1826 fires the light source 1824. In this manner, the multiplexer 1828 can achieve sequence firing through light guides 1822A-1822E or fire in any desired pattern relative to the light guides 1822A-1822E.

In this embodiment, the stage mover 1863 can have any suitable design for purposes of moving the multiplexer stage 1861 in a linear manner relative to the multiplexer base 1859. More particularly, the stage mover 1863 can be any suitable type of linear translation mechanism.

As shown in FIG. 18A, the catheter system 1800 can further include an optical element 1847, e.g., a reflecting or redirecting element such as a mirror, that reflects the source beam 1824A from the light source 1824 so that the source beam 1824A is directed toward the multiplexer 1828. In one embodiment, as shown, the optical element 1847 can be positioned along the beam path to redirect the source beam 1824A by approximately 90 degrees so that the source beam 1824A is directed toward the multiplexer 1828. Alternatively, the optical element 1847 can redirect the source beam 1824A by more than 90 degrees or less than 90 degrees. Still alternatively, the catheter system 1800 can be designed without the optical element 1847, and the light source 1824 can direct the source beam 1824A directly toward the multiplexer 1828.

Additionally, in this embodiment, the source beam 1824A being directed toward the multiplexer 1828 initially impinges on the redirector 1865, which is configured to redirect the source beam 1824A toward the coupling optics 1858. In some embodiments, the redirector 1865 redirects the source beam 1824A by approximately 90 degrees toward the coupling optics 1858. Alternatively, the redirector 1865 can redirect the source beam 1824A by more than 90 degrees or less than 90 degrees toward the coupling optics 1858. Thus, the redirector 1865 that is mounted on the multiplexer stage 1861 is configured to direct the source beam 1824A through the coupling optics 1858 so that individual guide beams 1824B are focused into the individual light guides 1822A-1822E in the guide coupling housing 1850.

The coupling optics 1858 can have any suitable design for purposes of focusing the individual guide beams 1824B to each of the light guides 1822A-1822E. In one embodiment, the coupling optics 1858 includes two lenses that are specifically configured to focus the individual guide beams 1824B as desired. Alternatively, the coupling optics 1858 can have another suitable design.

In certain non-exclusive alternative embodiments, the steering of the source beam 1824A so that it is properly directed and focused to each of the light guides 1822A-1822E can be accomplished using mirrors that are attached to optomechanical scanners, X-Y galvanometers or other multi-axis beam steering devices.

Still alternatively, although FIG. 18A illustrates that the light guides 1822A-1822E are fixed in position relative to the multiplexer base 1859, in some embodiments, it is appreciated that the light guides 1822A-1822E can be configured to move relative to coupling optics 1858 that are fixed in position. In such embodiments, the guide coupling housing 1850 itself would move, e.g., the guide coupling housing 1850 can be carried by a linear translation stage, and the system controller 1826 can control the linear translation stage to move in a stepped manner so that the light guides 1822A-1822E are each aligned, in a desired pattern, with the coupling optics 1858 and the guide beams 1824B. While such an embodiment can be effective, it is further appreciated that additional protection and controls would be required to make it safe and reliable as the guide coupling housing 1850 moves relative to the coupling optics 1858 of the multiplexer 1828 during use.

Figure 18B:
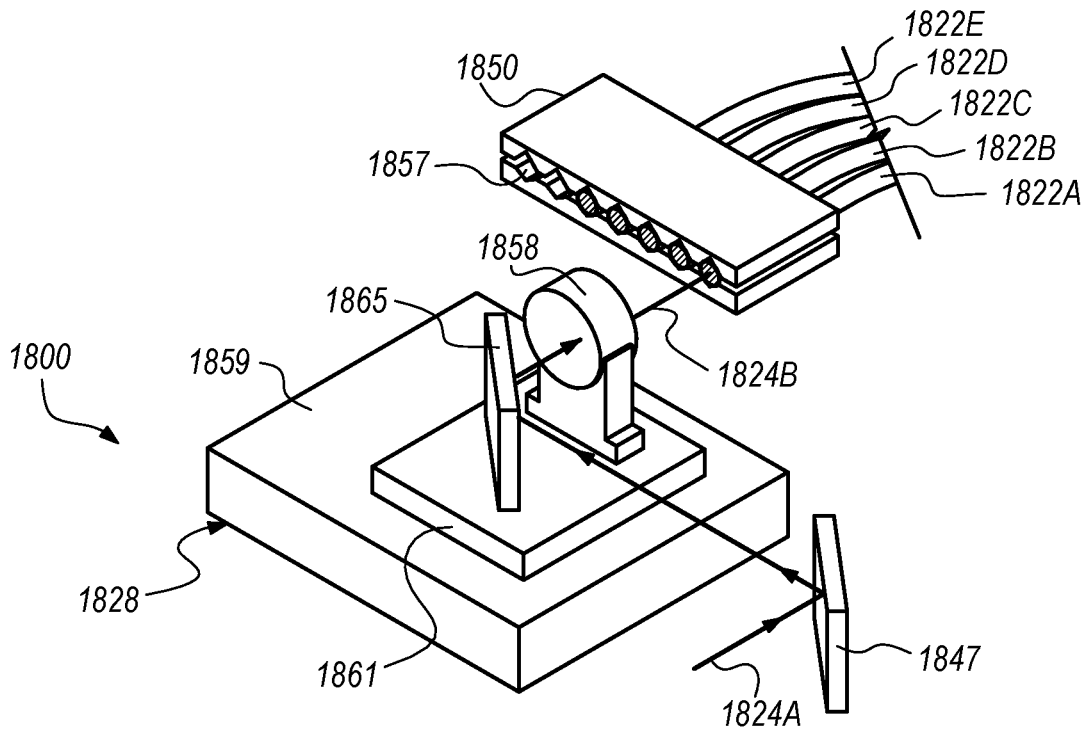
FIG. 18B is a simplified schematic perspective view illustration of a portion of the catheter system and the multiplexer illustrated in FIG. 18A.

FIG. 18B is a simplified schematic perspective view illustration of a portion of the catheter system 1800 and the multiplexer 1828 illustrated in FIG. 18A. In particular, FIG. 18B illustrates another view of the guide coupling housing 1850, with the guide coupling slots 1857, that is configured to retain a portion of each of the light guides 1822A-1822E; the optical element 1847 that initially redirects the source beam 1824A from the light source 1824 (illustrated in FIG. 18A) toward the multiplexer 1828; and the multiplexer 1828, including the multiplexer base 1859, the multiplexer stage 1861, the redirector 1865 and the coupling optics 1858, that receives the source beam 1824A and then directs and focuses individual guide beams 1824B toward each of the light guides 1822A-1822E. It is appreciated that the stage mover 1863 is not illustrated in FIG. 18B for purposes of simplicity and ease of illustration.

Figure 19A:
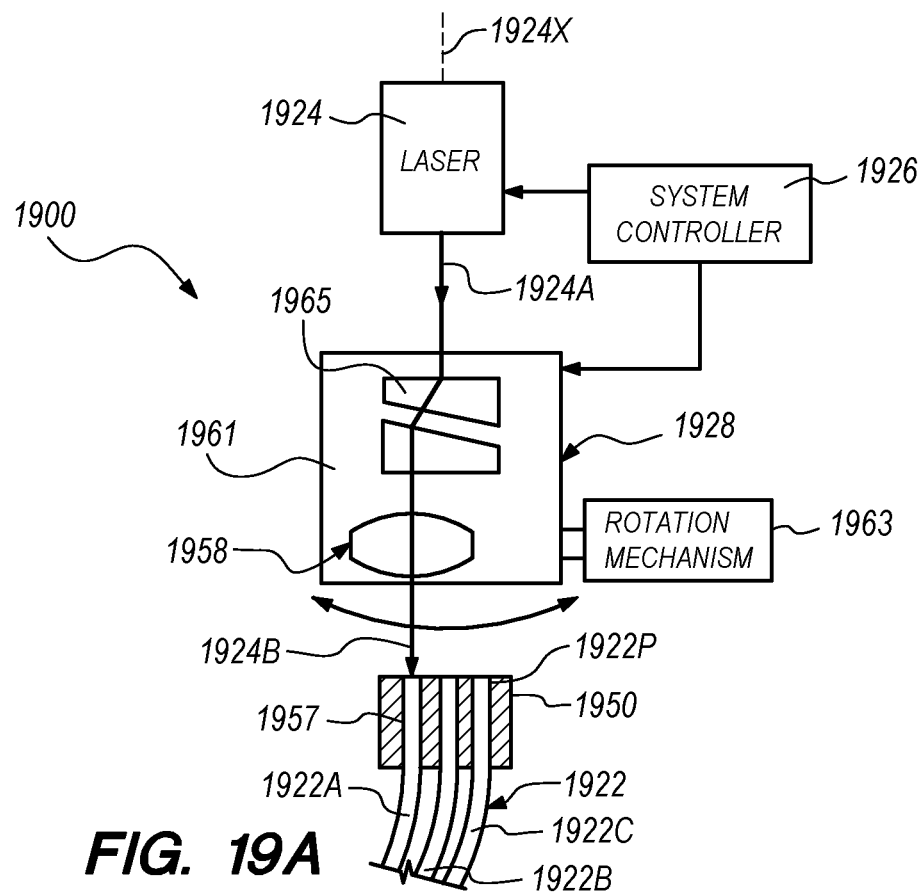
FIG. 19A is a simplified schematic top view illustration of a portion of yet another embodiment of the catheter system including yet another embodiment of the multiplexer.

FIG. 19A is a simplified schematic top view illustration of a portion of an embodiment of the catheter system 1900 including another embodiment of the multiplexer 1928. More particularly, FIG. 19A illustrates a light guide bundle 1922 including a plurality of light guides, such as a first light guide 1922A, a second light guide 1922B and a third light guide 1922C; a light source 1924; a system controller 1926; and the multiplexer 1928 that receives light energy in the form of a source beam 1924A, a pulsed source beam 1824A in various embodiments, from the light source 1924 and selectively and/or alternatively directs the light energy in the form of individual guide beams 1924B to each of the light guides 1922A-1922C. The light guide bundle 1922, the light guides 1922A-1922C, the light source 1924 and the system controller 1926 are substantially similar in design and function as described in detail herein above. Accordingly, such components will not be described in detail in relation to the embodiment illustrated in FIG. 19A. It is further appreciated that certain components of the system console 123 illustrated and described above in relation to FIG. 1, such as the power source 125 and the GUI 127, are not illustrated in FIG. 19A for purposes of simplicity and ease of illustration, but would typically be included in many embodiments.

It is appreciated that the light guide bundle 1922 can include any suitable number of light guides, which can be positioned and/or oriented relative to one another in any suitable manner to best align the plurality of light guides relative to the multiplexer 1928. For example, in the embodiment illustrated in FIG. 18A, the light guide bundle 1922 includes the first light guide 1922A, the second light guide 1922B, and the third light guide 1922C that are aligned in a linear arrangement relative to one another. Alternatively, the light guide bundle 1922 can include greater than three or less than three light guides.

As with previous embodiments, the multiplexer 1928 is configured to receive light energy in the form of the source beam 1924A from the light source 1924 and selectively and/or alternatively direct the light energy in the form of individual guide beams 1924B to each of the light guides 1922A-1922C. As such, as shown in FIG. 19A, the multiplexer 1928 is operatively and/or optically coupled in optical communication to the light guide bundle 1922 and/or to the plurality of light guides 1922A-1922C.

As illustrated, a guide proximal end 1922P of each of the plurality of light guides 1922A-1922C is retained within a guide coupling housing 1950, i.e. within guide coupling slots 1957 that are formed into the guide coupling housing 1950. In various embodiments, the guide coupling housing 1950 is configured to be selectively coupled to the system console 123 (illustrated in FIG. 1) so that the guide coupling slots 1957, and thus the light guides 1922A-1922C, are maintained in a desired fixed position relative to the multiplexer 1928 during use of the catheter system 1900.

Figure 19B:
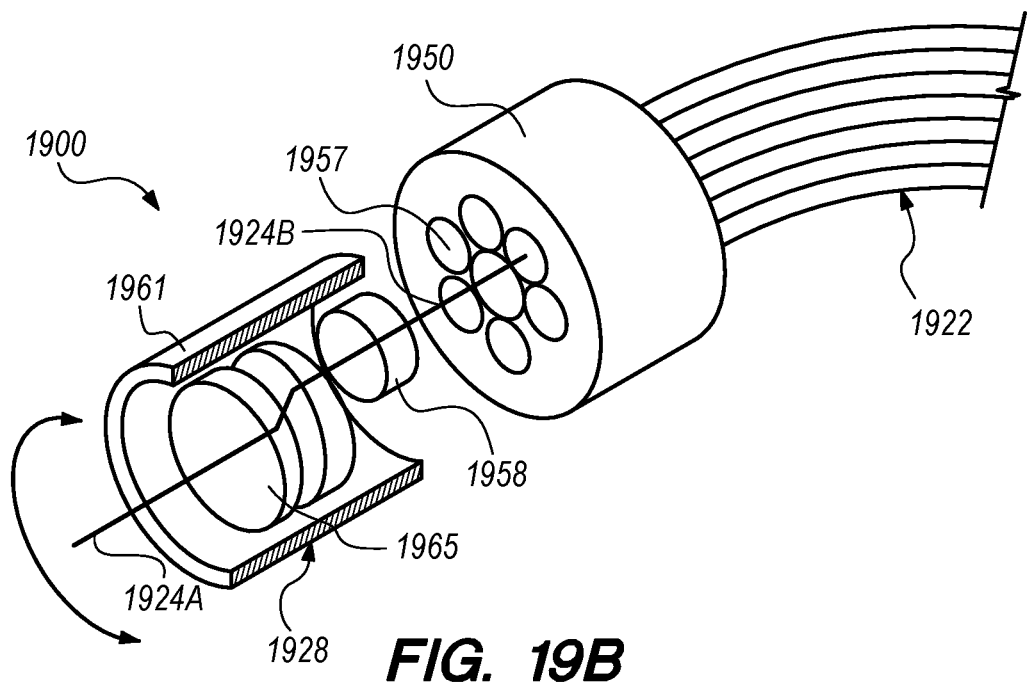
FIG. 19B is a simplified schematic perspective view illustration of a portion of the catheter system and the multiplexer illustrated in FIG. 19A.

Referring now to FIG. 19B, FIG. 19B is a simplified schematic perspective view illustration of a portion of the catheter system 1900 and the multiplexer 1928 illustrated in FIG. 19A. As shown in FIG. 19B, the guide coupling housing 1950 can be substantially cylindrical-shaped. It is appreciated that the guide coupling housing 1950 can have any suitable number of guide coupling slots 1957, which can be positioned and/or oriented relative to one another in any suitable manner to best align the guide coupling slots 1957 and thus the light guides 1922A-1922C of the light guide bundle 1922 relative to the multiplexer 1928. In the embodiment illustrated in FIG. 19B, the guide coupling housing 1950 includes seven guide coupling slots 1957 that are arranged in a circular and/or hexagonal packed pattern. Thus, in such embodiment, the guide coupling housing 1950 is capable of retaining the guide proximal end of up to seven light guides. Alternatively, the guide coupling housing 1950 can have greater than seven or less than seven guide coupling slots 1957, and/or the guide coupling slots 1957 can be arranged in a different manner relative to one another, such as in another suitable circular periodic pattern.

Returning to FIG. 19A, in this embodiment, the multiplexer 1928 includes one or more of a multiplexer stage 1961, a stage mover 1963, a redirector 1965, and coupling optics 1958. Alternatively, the multiplexer 1928 can include more components or fewer components than those specifically illustrated in FIG. 19A.

As shown in the embodiment illustrated in FIG. 19A, the stage mover 1963 is configured to move the multiplexer stage 1961 in a rotational manner. More particularly, in this embodiment, the multiplexer stage 1961 and/or the stage mover 1963 requires a single rotational degree of freedom. Additionally, as shown, the multiplexer stage 1961 and the guide coupling housing 1950 are aligned on a central axis 1924X of the light source 1924. As such, the multiplexer stage 1961 is configured to be rotated by the stage mover 1963 about the central axis 1924X.

The redirector 1965 and the coupling optics 1958 are mounted on and/or retained by the multiplexer stage 1961. During use of the catheter system 1900, the source beam 1924A is initially directed toward the multiplexer stage 1961 along the central axis 1924X of the light source 1924. Subsequently, the redirector 1965 is configured to deviate the source beam 1924A a fixed distance laterally off the central axis 1924X of the light source 1924, such that the source beam 1924A is directed in a direction that is substantially parallel to and spaced apart from the central axis 1924X. More specifically, the redirector 1965 deviates the source beam 1924A to coincide with the radius of the circular pattern of the light guides 1922A-1922C in the guide coupling housing 1950. As the multiplexer stage 1961 is rotated, the source beam 1924A that is directed through the redirector 1965 traces out a circular path.

It is appreciated that the redirector 1965 can have any suitable design. For example, in certain non-exclusive alternative embodiments, the redirector 1965 can be provided in the form of an anamorphic prism pair, a pair of wedge prisms, or a pair of close-spaced right angle mirrors or prisms. Alternatively, the redirector 1965 can include another suitable configuration of optics in order to achieve the desired lateral beam offset.

Additionally, as noted, the coupling optics 1958 are also mounted on and/or retained by the multiplexer stage 1961. As with the previous embodiments, the coupling optics 1958 are configured to focus the individual guide beams 1924B to each of the light guides 1922A-1922C in the light guide bundle 1922 retained, in part, within the guide coupling housing 1950 for optimal coupling.

The multiplexer 1928 is again configured to precisely align the coupling optics 1958 with each of the light guides 1922A-1922C such that the source beam 1924A generated by the light source 1924 can be precisely directed and focused by the multiplexer 1928 as a corresponding guide beam 1924B to each of the light guides 1922A-1922C. In certain embodiments, the stage mover 1963 and/or the multiplexer stage 1961 can be equipped with mechanical stops so that the coupling optics 1958 can be precisely aligned with the position of each of the light guides 1922A-1922C. Alternatively, the stage mover 1963 can be electronically controlled, such as by using stepper motors or a piezo-actuated rotational stage, to line the beam path of the guide beam 1924B sequentially with each individual light guide 1922A-1922C that is retained, in part, within the guide coupling housing 1950.

During use of the catheter system 1900, the stage mover 1963 drives the multiplexer stage 1961 to couple the guide beam 1924B with a selected light guide 1922A-1922C and then the system controller 1926 fires the light source 1924 in pulsed or semi-CW mode. The stage mover 1963 then steps the multiplexer stage 1961 angularly to the next stop, i.e. to the next light guide 1922A-1922C, and the system controller 1926 again fires the light source 1924. This process is repeated as desired so that light energy in the form of the guide beams 1924B is directed to each of the light guides 1922A-1922C in a desired pattern. It is appreciated that the stage mover 1963 can move the multiplexer stage 1961 so that it is aligned with any of the light guides 1922A-1922C, then the system controller 1926 fires the light source 1924. In this manner, the multiplexer 1928 can achieve sequence firing through light guides 1922A-1922C or fire in any desired pattern relative to the light guides 1922A-1922C.

In this embodiment, the stage mover 1963 can have any suitable design for purposes of moving the multiplexer stage 1961 in a rotational manner about the central axis 1924X. More particularly, the stage mover 1963 can be any suitable type of rotational mechanism.

Alternatively, although FIG. 19A illustrates that the light guides 1922A-1922C are fixed in position relative to the multiplexer stage 1961, in some embodiments, it is appreciated that the light guides 1922A-1922C can be configured to move and/or rotate relative to coupling optics 1958 that are fixed in position. In such embodiments, the guide coupling housing 1950 itself would move, with the guide coupling housing 1950 being rotated about the central axis 1924X, and the system controller 1926 can control the rotational stage to move in a stepped manner so that the light guides 1922A-1922C are each aligned, in a desired pattern, with the coupling optics 1958 and the guide beams 1924B. In such embodiment, the guide coupling housing 1950 would not be continuously rotated, but would be rotated a fixed number of degrees and then counter-rotated to avoid the winding of the light guides 1922A-1922C.

Returning again to FIG. 19B, FIG. 19B illustrates another view of the guide coupling housing 1950, with the guide coupling slots 1957, that is configured to retain a portion of each of the light guides; and the multiplexer 1928, including the multiplexer stage 1961, the redirector 1965 and the coupling optics 1958, that receives the source beam 1924A and then directs and focuses individual guide beams 1924B toward each of the light guides. It is appreciated that the stage mover 1963 is not illustrated in FIG. 19B for purposes of simplicity and ease of illustration.

Figure 20:
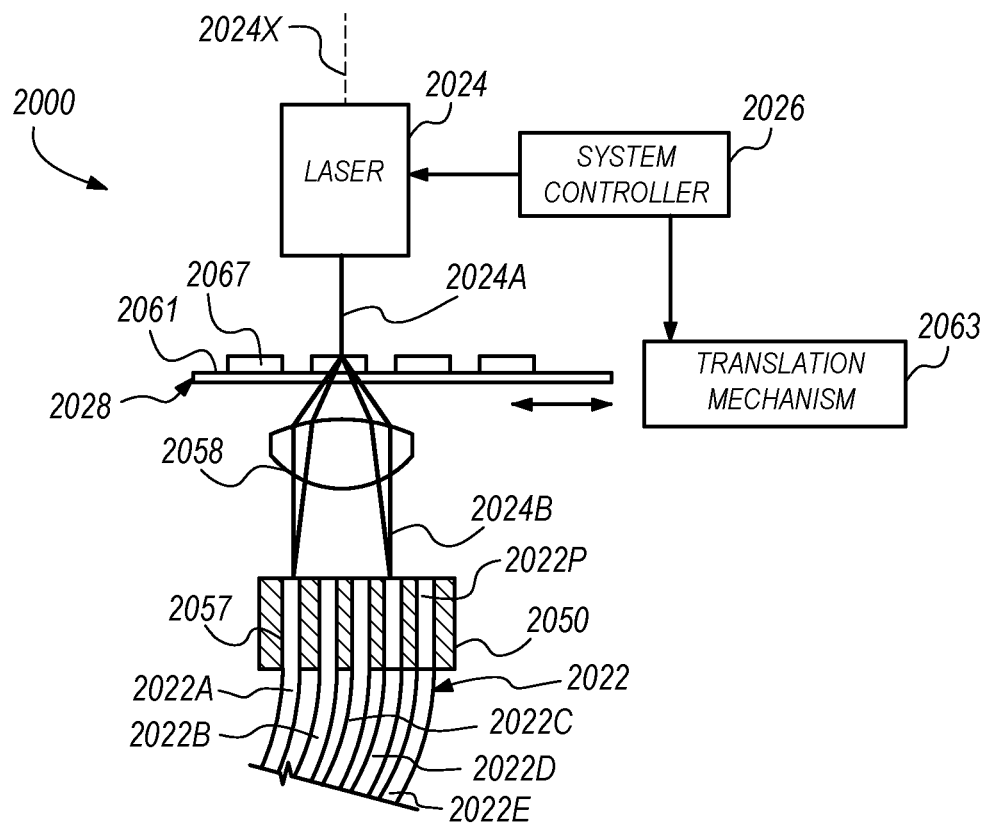
FIG. 20 is a simplified schematic illustration of a portion of another embodiment of the catheter system including another embodiment of the multiplexer.

FIG. 20 is a simplified schematic top view illustration of a portion of the catheter system 2000 and still another embodiment of the multiplexer 2028. More particularly, FIG. 20 illustrates a light guide bundle 2022 including a plurality of light guides, such as a first light guide 2022A, a second light guide 2022B, a third light guide 2022C, a fourth light guide 2022D and a fifth light guide 2022E; a light source 2024; a system controller 2026; and the multiplexer 2028 that receives light energy in the form of a source beam 2024A a pulsed source beam 2024A in various embodiments, from the light source 2024 and selectively and/or alternatively directs the light energy in the form of individual guide beams 2024B to each of the light guides 2022A-2022E. The light guide bundle 2022, the light guides 2022A-2022E, the light source 2024 and the system controller 2026 are substantially similar in design and function as described in detail herein above. Accordingly, such components will not be described in detail in relation to the embodiment illustrated in FIG. 20. It is further appreciated that certain components of the system console 123 illustrated and described above in relation to FIG. 1, such as the power source 125 and the GUI 127, are not illustrated in FIG. 20 for purposes of simplicity and ease of illustration, but would typically be included in many embodiments.

It is appreciated that the light guide bundle 2022 can include any suitable number of light guides, which can be positioned and/or oriented relative to one another in any suitable manner to best align the plurality of light guides relative to the multiplexer 2028. For example, in the embodiment illustrated in FIG. 20, the light guide bundle 2022 includes the first light guide 2022A, the second light guide 2022B, the third light guide 2022C, the fourth light guide 2022D and the fifth light guide 2022E that are aligned in a linear arrangement relative to one another. Alternatively, the light guide bundle 2022 can include greater than five or less than five light guides.

The multiplexer 2028 is again configured to receive light energy in the form of the source beam 2024A from the light source 2024 and selectively and/or alternatively direct the light energy in the form of individual guide beams 2024B to each of the light guides 2022A-2022E. As such, as shown in FIG. 20, the multiplexer 2028 is operatively and/or optically coupled in optical communication to the light guide bundle 2022 and/or to the plurality of light guides 2022A-2022E.

As illustrated, a guide proximal end 2022P of each of the plurality of light guides 2022A-2022E is retained within a guide coupling housing 2050, i.e. within guide coupling slots 2057 that are formed into the guide coupling housing 2050. In various embodiments, the guide coupling housing 2050 is configured to be selectively coupled to the system console 123 (illustrated in FIG. 1) so that the guide coupling slots 2057, and thus the light guides 2022A-2022E, are maintained in a desired fixed position relative to the multiplexer 2028 during use of the catheter system 2000. It is appreciated that the guide coupling housing 2050 can have any suitable number of guide coupling slots 2057. In the embodiment illustrated in FIG. 20, five guide coupling slots 2057 are visible within the guide coupling housing 2050. Thus, in such embodiment, the guide coupling housing 2050 is capable of retaining the guide proximal end 2022P of up to five light guides. Alternatively, the guide coupling housing 2050 can have greater than five or less than five guide coupling slots 2057.

In the embodiment illustrated in FIG. 20, the multiplexer 2028 includes one or more of a multiplexer stage 2061, a stage mover 2063, one or more diffractive optical elements 2067 (or "DOE"), and coupling optics 2058. Alternatively, the multiplexer 2028 can include more components or fewer components than those specifically illustrated in FIG. 20.

As shown, the diffractive optical elements 2067 are mounted on and/or retained by the multiplexer stage 2061. Additionally, the stage mover 2063 is configured to move the multiplexer stage 2061 such that each of the one or more diffractive optical elements 2067 are selectively and/or alternatively positioned in the beam path of the source beam 2024A from the light source 2024. In one such embodiment, the stage mover 2063 moves the multiplexer stage 2061 translationally such that each of the one or more diffractive optical elements 2067 are selectively and/or alternatively positioned in the beam path of the source beam 2024A from the light source 2024.

During use of the catheter system 2000, each of the one or more diffractive optical elements 2067 is configured to separate the source beam 2024A into one, two, three or more individual guide beams 2024B. It is appreciated that the diffractive optical elements 2067 can have any suitable design. For example, in certain non-exclusive embodiments, the diffractive optical elements 2067 can be created using arrays of micro-prisms, micro-lenses, or other patterned diffractive elements.

It is appreciated that there are many possible patterns to organize the light guides 2022A-2022E in the guide coupling housing 2050 using this approach. The simplest pattern for the light guides 2022A-2022E within the guide coupling housing 2050 would be a hexagonal, close-packed pattern, similar to what was illustrated in FIGS. 19A and 19B. Alternatively, the light guides 2022A-2022E within the guide coupling housing 2050 could also be arranged in a square, linear, circular, or other suitable pattern.

As shown in FIG. 20, the guide coupling housing 2050 can be aligned on the central axis 2024X of the light source 2024, with the diffractive optical elements 2067 mounted on the multiplexer stage 2061 being inserted along the beam path between the light source 2024 and the guide coupling housing 2050. Additionally, as illustrated, the coupling optics 2058 are also positioned along the central axis 2024X of the light source 2024, and the coupling optics 2058 are positioned between the diffractive optical elements 2067 and the guide coupling housing 2050.

During operation, the source beam 2024A impinging on one of the plurality of diffractive optical elements 2067 splits the source beam 2024A into two or more deviated beams, i.e. two or more guide beams 2024B. These guide beams 2024B are, in turn, directed and focused by the coupling optics 2058 down onto the individual light guides 2022A-2022E that are retained in the guide coupling housing 2050. In one configuration, the diffractive optical element 2067 would split the source beam 2024A into as many light guides as are present within the single-use device. In such configuration, the power in each guide beam 2024B is based on the number of guide beams 2024B that are generated from the single source beam 2024A minus scattering and absorption losses. Alternatively, the diffractive optical element 2067 can be configured to split the source beam 2024A so that guide beams 2024B are directed into any single light guide or any selected multiple light guides. Thus, the multiplexer stage 2061 can be configured to retain a plurality of diffractive optical elements 2067, with multiple diffractive optical element patterns etched on a single plate, to provide options for the user or operator for coupling the guide beams 2024B to the desired number and pattern of light guides. In such embodiments, pattern selection can be achieved by moving the multiplexer stage 2061 with the stage mover 2063 translationally so that the desired diffractive optical element 2067 is positioned in the beam path of the source beam 2024A between the light source 2024 and the coupling optics 2058.

As with the previous embodiments, the coupling optics 2058 can have any suitable design for purposes of focusing the individual guide beams 2024B, or multiple guide beams 2024B simultaneously, to the desired light guides 2022A-2022E.

Figure 21:
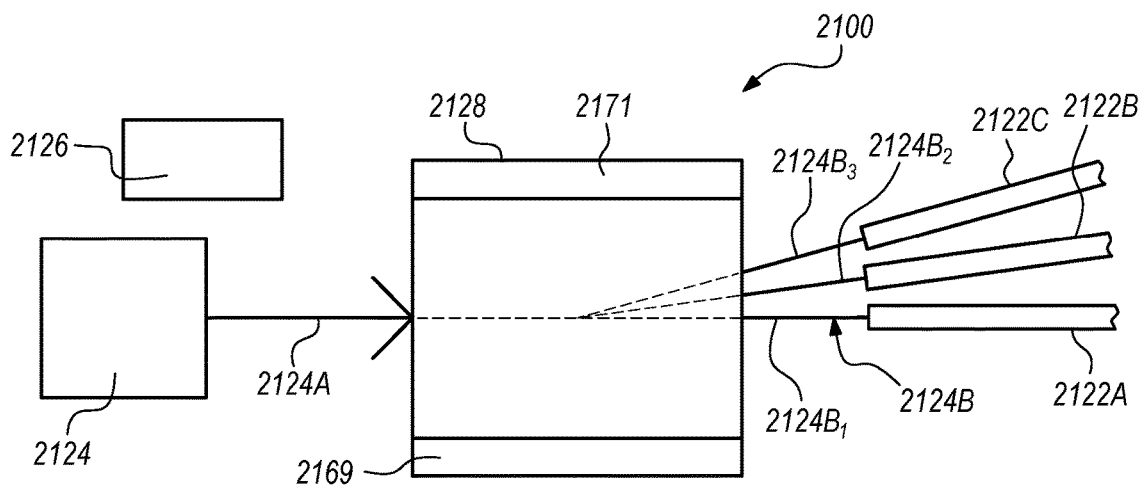
FIG. 21 is a simplified schematic illustration of a portion of still another embodiment of the catheter system including still another embodiment of the multiplexer.

FIG. 21 is a simplified schematic top view illustration of a portion of the catheter system 2100 and yet another embodiment of the multiplexer 2128. More particularly, FIG. 21 illustrates a plurality of light guides, such as a first light guide 2122A, a second light guide 2122B and a third light guide 2122C; a light source 2124; a system controller 2126; and the multiplexer 2128 that receives light energy in the form of a source beam 2124A, a pulsed source beam 1824A in various embodiments, from the light source 2124 and selectively and/or alternatively directs the light energy in the form of individual guide beams 2124B to each of the light guides 2122A-2122C. The light guides 2122A-2122C, the light source 2124 and the system controller 2126 are substantially similar in design and function as described in detail herein above. Accordingly, such components will not be described in detail in relation to the embodiment illustrated in FIG. 21. It is further appreciated that certain components of the system console 123 illustrated and described above in relation to FIG. 1, such as the power source 125 and the GUI 127, are not illustrated in FIG. 21 for purposes of simplicity and ease of illustration, but would typically be included in many embodiments.

It is appreciated that the catheter system 2100 can include any suitable number of light guides, which can be positioned and/or oriented relative to one another in any suitable manner to best align the plurality of light guides relative to the multiplexer 2128. For example, in the embodiment illustrated in FIG. 21, the catheter system 2100 includes the first light guide 2122A, the second light guide 2122B and the third light guide 2122C. Alternatively, the catheter system 2100 can include greater than three or less than three light guides.

The multiplexer 2128 is again configured to receive light energy in the form of the source beam 2124A from the light source 2124 and selectively and/or alternatively direct the light energy in the form of individual guide beams 2124B to each of the light guides 2122A-2122C. As such, as shown in FIG. 21, the multiplexer 2128 is operatively and/or optically coupled in optical communication to the plurality of light guides 2122A-2122C.

However, as illustrated in FIG. 21, the multiplexer 2128 has a different design than any of the previous embodiments. In some embodiments, it may be desirable to design the multiplexer 2128 to receive the source beam 2124A from a single light source 2124 and selectively and/or alternatively direct the light energy in the form of individual guide beams 2124B to each of the light guides 2122A-2122C in a manner that is easily reconfigurable and that does not involve moving parts. For example, using an acousto-optic deflector (AOD) as the multiplexer 2128 can allow the entire output of a single light source 2124, such as a single laser, to be directed into a plurality of individual light guides 2122A-2122C. The guide beam 2124B can be re-targeted to a different light guide 2122A-2122C within microseconds by simply changing the driving frequency input into the multiplexer 2128 (the AOD), and with a pulsed laser such as a Nd:YAG, this switching can easily occur between pulses. In such embodiments, the deflection angle ($\Theta$) of the multiplexer 2128 can be defined as follows:

Deflection angle ($\Theta$)=$\Lambda f/v$ where $\Lambda$=Optical Wavelength f=acoustic drive frequency v=speed of sound in modulator As shown in FIG. 21, the source beam 2124A is directed from the light source 2124 toward the multiplexer 2128, and is subsequently redirected due to the generated deflection angle as a desired guide beam 2124B to each of the light guides 2122A-2122C. More specifically, as illustrated, when the multiplexer 2128 generates a first deflection angle for the source beam 2124A, a first guide beam $2124B_1$ is directed to the first light guide 2122A; when the multiplexer 2128 generates a second deflection angle for the source beam 2124A, a second guide beam $2124B_2$ is directed to the second light guide 2122B; and when the multiplexer 2128 generates a third deflection angle for the source beam 2124A, a third guide beam $2124B_3$ is directed to the third light guide 2122C. It is appreciated that, as illustrated, any desired deflection angle can include effectively no deflection angle at all, i.e. the guide beam 2124B can be directed to continue along the same axial beam path as the source beam 2124A.

In this embodiment, the multiplexer 2128 (AOD) includes a transducer 2169 and an absorber 2171 that cooperate to generate the desired driving frequency that can, in turn, generate the desired deflection angle so that the source beam 2124A is redirected as the desired guide beam 2124B toward the desired light guide 2122A-2122C. More particularly, the multiplexer 2128 is configured to spatially control the source beam 2124A. In the operation of the multiplexer 2128, the power driving the acoustic transducer 2169 is kept on, at a constant level, while the acoustic frequency is varied to deflect the source beam 2124A to different angular positions that define the guide beams $2124B_1$-$2124B_3$. Thus, the multiplexer 2128 makes use of the acoustic frequency-dependent diffraction angle, such as described above.

Figure 22:
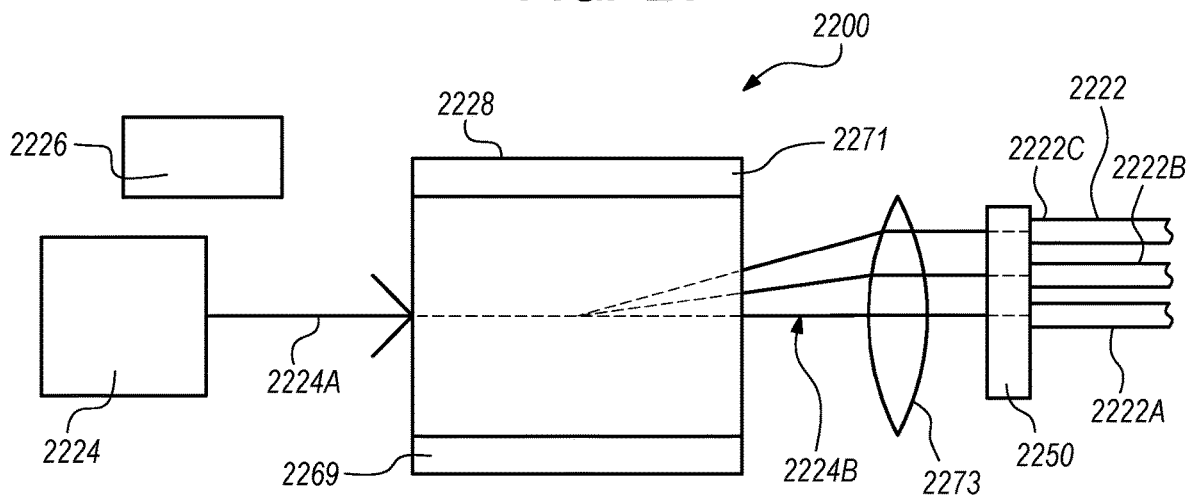
FIG. 22 is a simplified schematic illustration of a portion of another embodiment of the catheter system including another embodiment of the multiplexer.

FIG. 22 is a simplified schematic top view illustration of a portion of the catheter system 2200 and still another embodiment of the multiplexer 2228. More particularly, FIG. 22 illustrates a light guide bundle 2222 including a plurality of light guides, such as a first light guide 2222A, a second light guide 2222B and a third light guide 2222C; a light source 2224; a system controller 2226; and the multiplexer 2228 that receives light energy in the form of a source beam 2224A, a pulsed source beam 2224A in various embodiments, from the light source 2224 and selectively and/or alternatively directs the light energy in the form of individual guide beams 2224B to each of the light guides 2222A-2222C. The light guide bundle 2222, the light guides 2222A-2222C, the light source 2224 and the system controller 2226 are substantially similar in design and function as described in detail herein above. Accordingly, such components will not be described in detail in relation to the embodiment illustrated in FIG. 22. It is further appreciated that certain components of the system console 123 illustrated and described above in relation to FIG. 1, such as the power source 125 and the GUI 127, are not illustrated in FIG. 22 for purposes of simplicity and ease of illustration, but would typically be included in many embodiments.

It is appreciated that the light guide bundle 2222 can include any suitable number of light guides, which can be positioned and/or oriented relative to one another in any suitable manner to best align the plurality of light guides relative to the multiplexer 2228. For example, in the embodiment illustrated in FIG. 22, the light guide bundle 2222 includes the first light guide 2222A, the second light guide 2222B and the third light guide 2222C that are aligned in a linear arrangement relative to one another. Alternatively, the light guide bundle 2222 can include greater than three or less than three light guides.

The multiplexer 2228 illustrated in FIG. 22 is substantially similar to the multiplexer 2128 illustrated and described in relation to FIG. 21. For example, as shown in FIG. 22, the multiplexer 2228 again includes a transducer 2269 and an absorber 2271 that cooperate to generate the desired driving frequency that can, in turn, generate the desired deflection angle so that the source beam 2224A is redirected as the desired guide beam 2224B toward the desired light guide 2222A-2222C. However, in this embodiment, the multiplexer 2228 further includes an optical element 2273 that is usable to transform the angular separation between the guide beams 2224B into a linear offset.

In some embodiments, in order to improve the angular resolution and the efficiency of the catheter system 2200, the input laser 2224 should be collimated with a diameter close to filling the aperture of the multiplexer 2228 (the AOD). The smaller the divergence of the input, the greater number of discrete outputs can be generated. The angular resolution of such a device is quite good, but the total angular deflection is limited. To allow a sufficient number of light guides 2222A-2222C of finite size to be accessed by a single light source 2224 and a single source beam 2224A, there are a number of means to improve the separation of the different output. For example, as shown in FIG. 22, after the individual guide beams 2224B separate, the optical element 2273, such as a lens, can be used to transform the angular separation between the guide beams 2224B into a linear offset, and can be used to direct the guide beams 2224B into closely spaced light guides 2222A-2222C, such as when the light guides 2222A-2222C are held in close proximity to one another within a guide coupling housing 2250. Additionally, folding mirrors can be used to allow adequate propagation distance to separate the different beam paths of the guide beams 2224B within a limited volume.

Figure 23:
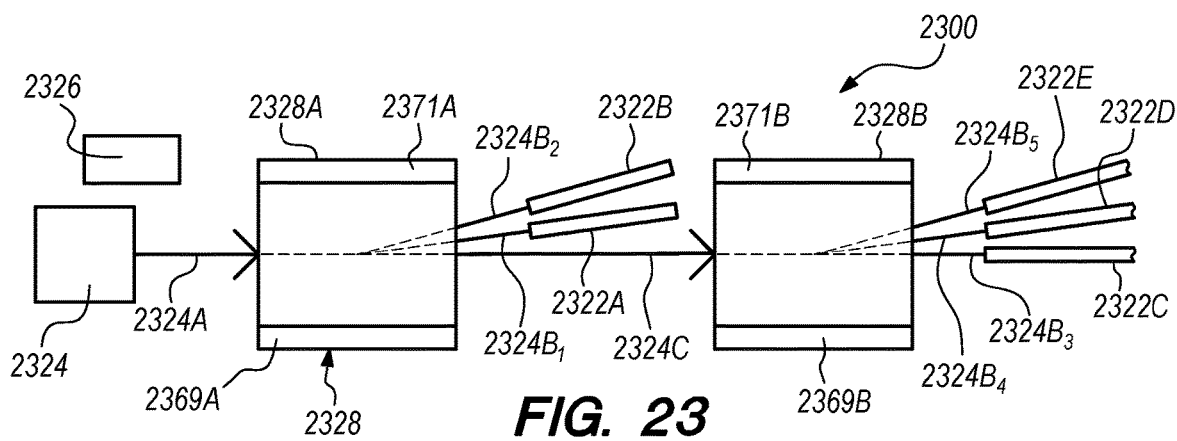
FIG. 23 is a simplified schematic illustration of a portion of still yet another embodiment of the catheter system including still yet another embodiment of the multiplexer.

FIG. 23 is a simplified schematic top view illustration of a portion of the catheter system 2300 and still yet another embodiment of the multiplexer 2328. More particularly, FIG. 23 illustrates a plurality of light guides, such as a first light guide 2322A, a second light guide 2322B, a third light guide 2322C, a fourth light guide 2322D and a fifth light guide 2322E; alight source 2324; a system controller 2326; and the multiplexer 2328 that receives light energy in the form of a source beam 2324A, a pulsed source beam 2324A in various embodiments, from the light source 2324 and selectively and/or alternatively directs the light energy in the form of individual guide beams 2324B to each of the light guides 2322A-2322E. The light guides 2322A-2322E, the light source 2324 and the system controller 2326 are substantially similar in design and function as described in detail herein above. Accordingly, such components will not be described in detail in relation to the embodiment illustrated in FIG. 23. It is further appreciated that certain components of the system console 123 illustrated and described above in relation to FIG. 1, such as the power source 125 and the GUI 127, are not illustrated in FIG. 23 for purposes of simplicity and ease of illustration, but would typically be included in many embodiments.

It is appreciated that the catheter system 2300 can include any suitable number of light guides, which can be positioned and/or oriented relative to one another in any suitable manner to best align the plurality of light guides relative to the multiplexer 2328. For example, in the embodiment illustrated in FIG. 23, the catheter system 2300 includes the first light guide 2322A, the second light guide 2322B, the third light guide 2322C, the fourth light guide 2322D and the fifth light guide 2322E. Alternatively, the catheter system 2100 can include greater than five or less than five light guides.

The manner for multiplexing the source beam 2324A into multiple guide beams 2324B illustrated in FIG. 23 is somewhat similar to how the source beam 2124A was multiplexed into multiple guide beams 2124B as illustrated and described in relation to FIG. 21. However, in this embodiment, the multiplexer 2328 includes a pair of acousto-optic deflectors (AODs), i.e. a first acousto-optic deflector 2328A and a second acousto-optic deflector 2328B, that are positioned in series with one another. With such design, the multiplexer 2328 may be able to access additional light guides. Additionally, it is further appreciated that the multiplexer 2328 can include more than two acousto-optic deflectors, if desired, to be able to access even more light guides.

In the embodiment shown in FIG. 23, the source beam 2324A is initially directed toward the first AOD 2328A. The first AOD 2328A is utilized to deflect the source beam 2324A to generate a first guide beam $2324B_1$ that is directed toward the first light guide 2322A, and a second guide beam $2324B_2$ that is directed toward the second light guide 2322B2. Additionally, the first AOD 2328A also allows an undeviated beam to be transmitted through the first AOD 2328A as a transmitted beam 2324C that is directed toward the second AOD 2328B. Subsequently, the second AOD 2328B is utilized to deflect the transmitted beam 2324C, as desired, to generate a third guide beam $2324B_3$ that is directed toward the third light guide 2322C, a fourth guide beam $2324B_4$ that is directed toward the fourth light guide 2322D, and a fifth guide beam $2324B_5$ that is directed toward the fifth light guide 2322E.

Additionally, each AOD 2328A, 2328B can be designed in a similar manner to those described in greater detail above. For example, the first AOD 2328A can include a first transducer 2369A and a first absorber 2371A that cooperate to generate the desired driving frequency that can, in turn, generate the desired deflection angle so that the source beam 2324A is redirected as desired; and the second AOD 2328B can include a second transducer 2369B and a second absorber 2371B that cooperate to generate the desired driving frequency that can, in turn, generate the desired deflection angle so that the transmitted beam 2324C is redirected as desired. Alternatively, the first AOD 2328A and/or the second AOD 2328B can have another suitable design.

As described in detail herein, in various embodiments, the multiplexer can be utilized to solve many problems that exist in more traditional catheter systems. For example:

1) Use of a multiplexer such as described herein allows use of one light source, e.g., laser source, to power multiple fiber optic channels in a single-use device. In more traditional catheter systems, it would require a powerful and potentially large laser to power all channels of a multi-channel device simultaneously. Conversely, the approach as described in detail herein allows the use of a smaller, lower-power laser with a high repetition rate to achieve similar clinical effectiveness as a much larger laser operated at a lower repetition rate.

2) Use of a multiplexer such as described herein supports multiple single-use device configurations with a single console. The number of channels in the single-use device could be programmed, allowing varied configurations for different clinical application. Additionally, the channels, e.g., light guides, can be positioned in any suitable manner relative to one another, and/or relative to the catheter shaft, the guidewire lumen and/or the balloon to provide the desired treatments at the desired locations. Importantly, all devices could still be operated by a single laser console or system.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a vessel wall within a body of a patient, the catheter system including a single light source that generates light energy, the catheter system comprising:
    a first light guide and a second light guide that are each configured to selectively receive light energy from the light source;
    a multiplexer that receives the light energy from the light source in the form of a source beam and selectively directs the light energy from the light source in the form of individual guide beams to each of the first light guide and the second light guide, the multiplexer including (i) a multiplexer base that is fixed in position relative to the first light guide and the second light guide, (ii) a multiplexer stage that is movably supported on the multiplexer base, (iii) a stage mover that is configured to move the multiplexer stage in a single linear degree of freedom relative to the multiplexer base, (iv) a redirector that is mounted on the multiplexer stage, and (v) coupling optics that are mounted on the multiplexer stage;
    a catheter shaft;
    a balloon that is coupled to the catheter shaft, the balloon including a balloon wall that defines a balloon interior, the balloon being configured to retain a balloon fluid within the balloon interior, the balloon being selectively inflatable with the balloon fluid to expand to an inflated state such that when the balloon is in the inflated state the balloon wall is configured to be positioned adjacent to the treatment site, the first light guide and the second light guide being positioned at least partially within the balloon interior; and
    a system controller including a processor that is configured to control operation of the light source to generate a single source beam in the form of pulses of light energy that are directed to the multiplexer;
    wherein the source beam being directed toward the multiplexer initially impinges on the redirector, the redirector being configured to redirect the source beam toward the coupling optics, the coupling optics being configured to focus the individual guide beams received from the redirector to each of the first light guide and the second light guide;
    wherein movement of the multiplexer stage relative to the multiplexer base results in corresponding movement of the redirector and the coupling optics relative to the first light guide and the second light guide;
    wherein the stage mover moves the multiplexer stage to align a first beam path of a first guide beam with the first light guide before the system controller fires the light source to generate the first guide beam that is directed to the first light guide;
    wherein the stage mover subsequently moves the multiplexer stage to align a second beam path of a second guide beam with the second light guide before the system controller fires the light source to generate the second guide beam that is directed to the second light guide; and
    wherein the first light guide and the second light guide receive the light energy from the light source and guide the light energy from the light source into the balloon interior to generate plasma in the balloon fluid within the balloon interior, the plasma generation causing rapid bubble formation and imparting pressure waves upon the balloon wall adjacent to the treatment site.

2. The catheter system of claim 1 wherein the multiplexer receives the light energy from the light source and simultaneously directs the light energy from the light source in the form of individual guide beams to each of the first light guide and the second light guide.

3. The catheter system of claim 1 wherein the multiplexer receives the light energy from the light source and sequentially directs the light energy from the light source in the form of individual guide beams to each of the first light guide and the second light guide.

4. The catheter system of claim 1 wherein the light source includes a laser.

5. A catheter system for treating a treatment site within or adjacent to a vessel wall within a body of a patient, the catheter system including a single light source that generates light energy, the catheter system comprising:
- a first light guide and a second light guide that are each configured to selectively receive light energy from the light source; and
- a multiplexer that receives the light energy from the light source in the form of a source beam and selectively directs the light energy from the light source in the form of individual guide beams to each of the first light guide and the second light guide, the multiplexer including (i) an optical element that splits the source beam into a first guide beam and a second guide beam, and (ii) coupling optics that are configured to focus the first guide beam onto the first light guide and the second guide beam onto the second light guide;
- wherein the optical element includes an input surface that is partially reflective, a rear surface, and an exit surface that is anti-reflective; and
- wherein the source beam impinging on the input surface splits the source beam into the first guide beam that is directed toward the coupling optics, and the second guide beam that is transmitted through the input surface toward the rear surface, reflects off of the rear surface and is directed through the exit surface and toward the coupling optics.

6. The catheter system of claim 5 wherein the optical element is an imperfect parallelogram.

7. The catheter system of claim 1 wherein the balloon includes a drug eluting coating.

8. The catheter system of claim 1 further comprising a power source that is configured to provide power to each of the light source, the system controller and the multiplexer.

9. The catheter system of claim 1 wherein the redirector redirects the source beam by approximately 90 degrees toward the coupling optics.

10. The catheter system of claim 1 further comprising an optical element that is positioned in a beam path of the source beam and that redirects the source beam from the light source so that the source beam is directed toward the multiplexer.

11. The catheter system of claim 10 wherein the optical element redirects the source beam from the light source by approximately 90 degrees so that the source beam is directed toward the multiplexer.

12. The catheter system of claim 5 further comprising a catheter shaft and a balloon that is coupled to the catheter shaft, the balloon including a balloon wall that defines a balloon interior, the balloon being configured to retain a balloon fluid within the balloon interior, the balloon being selectively inflatable with the balloon fluid to expand to an inflated state such that when the balloon is in the inflated state the balloon wall is configured to be positioned adjacent to the treatment site, the first light guide and the second light guide being positioned at least partially within the balloon interior.

13. The catheter system of claim 12 wherein the first light guide and the second light guide receive the light energy from the light source and guide the light energy from the light source into the balloon interior to generate plasma in the balloon fluid within the balloon interior, the plasma generation causing rapid bubble formation and imparting pressure waves upon the balloon wall adjacent to the treatment site.

* * * * *